(12) United States Patent
Contessa et al.

(10) Patent No.: US 11,219,625 B2
(45) Date of Patent: Jan. 11, 2022

(54) INHIBITORS OF N-LINKED GLYCOSYLATION AND METHODS USING SAME

(71) Applicants: YALE UNIVERSITY, New Haven, CT (US); THE UNIVERSITY OF KANSAS, Lawrence, KS (US)

(72) Inventors: Joseph N. Contessa, Guilford, CT (US); Jennifer E. Golden, Madison, WI (US); Daniel P. Flaherty, West Lafayette, IN (US)

(73) Assignees: YALE UNIVERSITY, New Haven, CT (US); THE UNIVERSITY OF KANSAS, Lawrence, KS (US)

( * ) Notice: Subject to any disclaimer, the term of this patent is extended or adjusted under 35 U.S.C. 154(b) by 180 days.

(21) Appl. No.: 15/746,043

(22) PCT Filed: Jul. 22, 2016

(86) PCT No.: PCT/US2016/043664
§ 371 (c)(1),
(2) Date: Jan. 19, 2018

(87) PCT Pub. No.: WO2017/019540
PCT Pub. Date: Feb. 2, 2017

(65) Prior Publication Data
US 2019/0000858 A1   Jan. 3, 2019

Related U.S. Application Data

(60) Provisional application No. 62/306,326, filed on Mar. 10, 2016, provisional application No. 62/196,744, filed on Jul. 24, 2015.

(51) Int. Cl.
| | | |
|---|---|---|
| A61K 31/5377 | (2006.01) |
| A61K 31/402 | (2006.01) |
| A61K 31/426 | (2006.01) |
| A61K 31/427 | (2006.01) |
| A61K 31/454 | (2006.01) |
| C07D 295/192 | (2006.01) |
| C07D 213/75 | (2006.01) |
| A61P 35/00 | (2006.01) |
| A61K 45/06 | (2006.01) |
| C07D 277/46 | (2006.01) |
| C07D 277/82 | (2006.01) |
| C07D 295/155 | (2006.01) |
| C07D 417/12 | (2006.01) |

(52) U.S. Cl.
CPC ........ *A61K 31/5377* (2013.01); *A61K 31/402* (2013.01); *A61K 31/426* (2013.01); *A61K 31/427* (2013.01); *A61K 31/454* (2013.01); *A61K 45/06* (2013.01); *A61P 35/00* (2018.01); *C07D 213/75* (2013.01); *C07D 277/46* (2013.01); *C07D 277/82* (2013.01); *C07D 295/155* (2013.01); *C07D 295/192* (2013.01); *C07D 417/12* (2013.01)

(58) Field of Classification Search
None
See application file for complete search history.

(56) References Cited

U.S. PATENT DOCUMENTS

| | | | |
|---|---|---|---|
| 7,544,676 B2* | 6/2009 | Dolle | C07D 207/12 514/210.01 |
| 9,504,676 B2* | 11/2016 | Dariavach | A61K 31/4155 |
| 10,213,433 B2* | 2/2019 | Catron | A61K 31/496 |
| 2006/0079557 A1 | 4/2006 | Dolle et al. | |
| 2006/0135773 A1 | 6/2006 | Semple et al. | |
| 2010/0016310 A1 | 1/2010 | Ingraham et al. | |

OTHER PUBLICATIONS

Luangdilok, Sutima. Syk Tyrosine Kinase Is Linked to Cell Motility and Progression in Squamous Cell Carcinomas of the Head and Neck. Cancer Res. 2007, 67 (16), 7907-7916.*
International Search Report and Written Opinion for PCT International Application No. PCT/US2016/043664 dated Feb. 15, 2017.
PubChem: Substance Record for SID 111590126. Retrieved on Sep. 16, 2016. Retrieved from the Internet. <URL: https://pubchem.ncbi.nlm.nih.gov/substance/111590123>, Mar. 7, 2011.
Weerapana , et al., "Peptides to peptidomimetics: towards the design and synthesis of bioavailable inhibitors of oligosaccharyl transferase", Org. Biomol. Chem. 1, 2003, 93-99.

* cited by examiner

*Primary Examiner* — Samantha L Shterengarts
(74) *Attorney, Agent, or Firm* — Saul Ewing Arnstein & Lehr LLP; Domingos J. Silva

(57) ABSTRACT

The present invention includes novel compounds and methods for preventing or treating diseases associated with N-linked glycosylation in a subject in need thereof. The methods comprise administering to the subject an effective amount of at least one compound of the invention.

12 Claims, 28 Drawing Sheets

Specification includes a Sequence Listing.

FIG. 1D
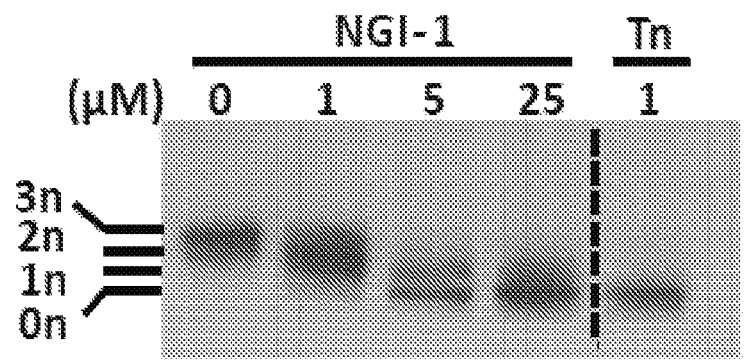
FIG. 2A
FIG. 2B
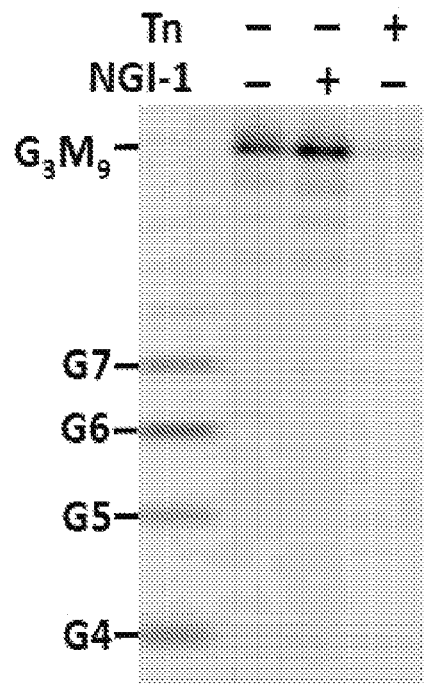

H1581

H2444

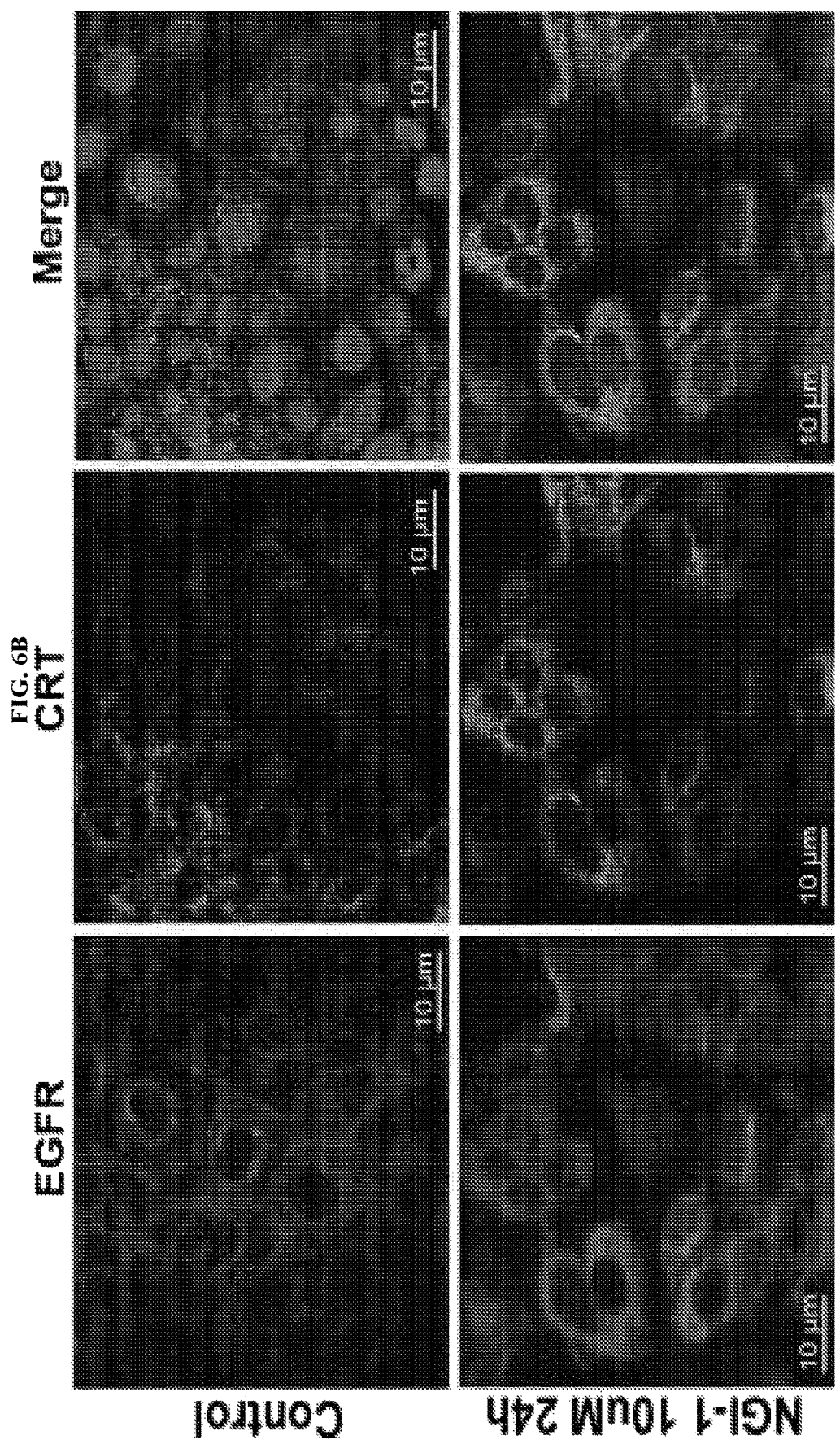

H3255

HCC827

NGI-1 10μM

NGI-1 10μM

INHIBITORS OF N-LINKED GLYCOSYLATION AND METHODS USING SAME

CROSS-REFERENCE TO RELATED APPLICATIONS

This application is a 35 U.S.C. § 371 national phase application from, and claims priority to, International Application No. PCT/US2016/043664, filed Jul. 22, 2016, and published under PCT Article 21(2) in English, which claims priority under 35 U.S.C. § 119(e) to U.S. Provisional Application No. 62/196,744, filed Jul. 24, 2015, and U.S. Provisional Application No. 62/306,326, filed Mar. 10, 2016, all of which are incorporated herein by reference in their entireties.

STATEMENT REGARDING FEDERALLY SPONSORED RESEARCH OR DEVELOPMENT

This invention was made with government support under DA033178, HG005031 and HG005032 awarded by National Institutes of Health. The government has certain rights in the invention.

BACKGROUND OF THE INVENTION

Asparagine (N)-linked glycosylation is a co- and post-translational modification common to proteins of the endoplasmic reticulum (ER) and secretory pathway. This process requires the biosynthesis of a glycan precursor, or lipid linked oligosaccharide (LLO), and involves the coordinated function of at least 30 gene products and 17 enzymatic activities. LLO synthesis is initiated in the cytoplasm through addition of N-acetyl glucosamine to phosphorylated dolichol lipids, an enzymatic step that is blocked by the natural product tunicamycin (Tn). Sequential carbohydrate addition by glycosyltransferases associated with the cytoplasmic ER membrane elongates the LLO, and the $Man_5GlcNac_2$ intermediate is then transferred into the lumen of the ER by an unknown mechanism involving RFT1. Proteins that synthesize and transport carbohydrate precursors along with glycosyltransferases of the ER lumen add mannoses or glucose and form the $Glc_3Man_9GlcNac_2$ LLO. This mature LLO is then transferred to NXT/S (where X cannot be W) consensus sequences of nascent proteins by the oligosaccharyltransferase (OST).

Although the biochemical basis for synthesis and transfer of N-linked glycans to recipient proteins has been elucidated, control of this process by mammalian cells is not well understood. N-linked glycosylation was initially considered to be constitutive without sites of regulation. This belief was based on two fundamental observations: (1) many of the N-linked glycosylation genes are essential and (2) the prevalent use of tunicamycin that induces cell death. This concept, however, was incongruent with discoveries about the oligosaccharyltransferase biology. Yeast genetics demonstrated that several of the OST subunits were in fact non-essential, requiring synthetic lethal strategies for identification. Furthermore in mammals the OST catalytic subunit (STT3 in yeast) is encoded by two separate genes, STT3A and STT3B, suggesting a mechanism for genetic regulation of LLO transfer. The seven subunits that compose the OST complex were also found to exist in at least 4 combinations that vary with respect to inclusion of either STT3A or STT3B and either TUSC3 or MAGT1. Thus, the OST represents at least one enzymatic node for control of N-linked glycosylation and provides molecular evidence for a model where N-linked glycosylation itself can be actively regulated.

However, attributing the consequences of abnormal N-linked glycosylation to the altered function of specific glycoproteins is difficult. The evolving experience with human congenital disorders of glycosylation, and their disparate clinical presentations, has made it difficult to identify both the specific proteins and cellular contexts that are most sensitive to disruption.

Receptor tyrosine kinase (RTK) glycoproteins such as EGFR and FGFR family members are sensitive to perturbations in glycosylation, and RTKs may represent a protein class that mediates the effects of abnormal N-linked glycosylation. RTK extracellular domains are highly modified with N-linked glycans which contribute to stable conformations that facilitate ligand binding and regulate downstream signal transduction. The EGFR and FGFR1, for example, have eleven and eight consensus glycosylation sites respectively, whereas the average number of N-linked sites per glycoprotein is estimated to be only 1.9. However the interplay between N-linked glycosylation and RTK function has remained unknown.

Thus, there is a need in the art for novel compositions and methods that can be used to treat diseases or disorders associated with N-linked glycosylation in a mammal. The present invention addresses this unmet need.

BRIEF SUMMARY OF THE INVENTION

The invention provides a compound of formula (I), or a salt, solvate, enantiomer, diastereoisomer or tautomer thereof:

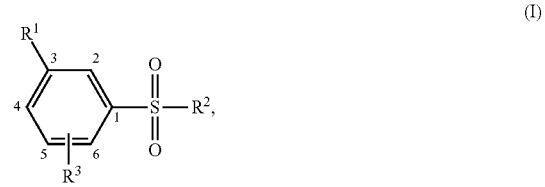

wherein in (I):

$R^1$ is selected from the group consisting of

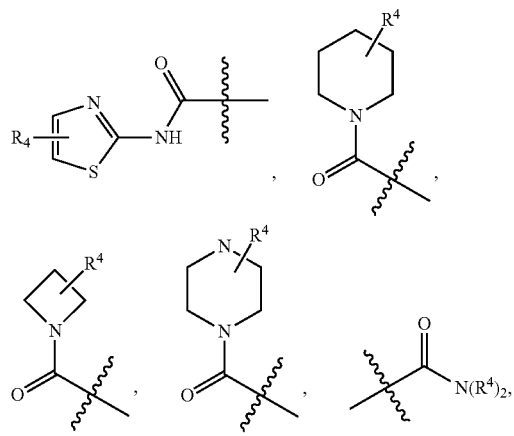

-continued

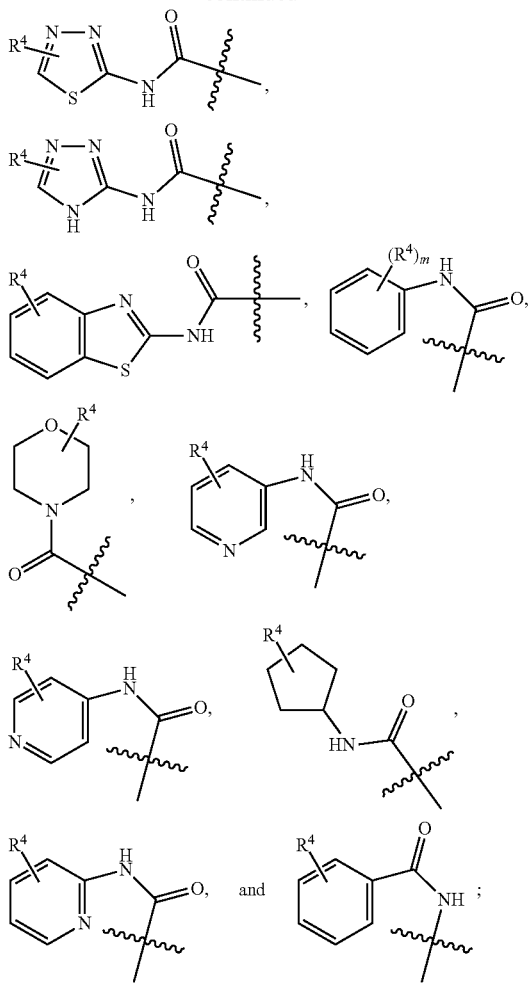

m=1 or 2;

R² is selected from the group consisting of

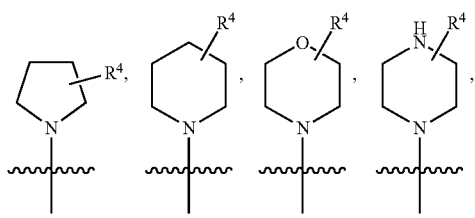

and —N(R⁴)₂;

R³ is selected from the group consisting of

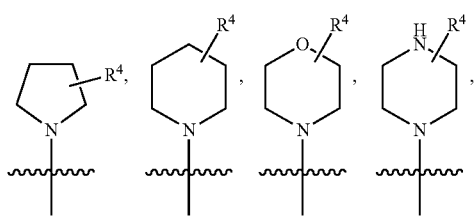

-continued

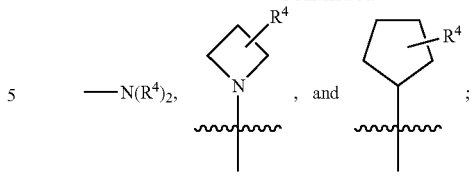

each occurrence of R⁴ is independently selected from the group consisting of H, —(C₁-C₆)alkyl, —(C₃-C₆)cycloalkyl, —(C₁-C₆)haloalkyl, —(C₁-C₆)alkoxy, —(C₃-C₁₀)heterocyclyl, —(C₁-C₆)heteroalkyl, —F, —Cl, —Br, —I, —CN, —NO₂, —OR⁵, —SR⁵, —S(=O)R⁵, —S(=O)₂R⁵, —C(=O)R⁵, —OC(=O)R⁵, —C(=O)OR⁵, aryl, —CH₂-aryl, and —(C₅-C₁₀)heteroaryl, wherein the alkyl, heteroalkyl cycloalkyl, heterocyclyl, aryl, or heteroaryl group is optionally substituted; and, each occurrence of R⁵ is independently selected from the group consisting of H, —(C₁-C₆)alkyl, —(C₁-C₆)heteroalkyl, —(C₃-C₆)cycloalkyl, —(C₃-C₁₀)heterocyclyl, aryl, and —(C₅-C₁₀)heteroaryl, wherein the alkyl, heteroalkyl, cycloalkyl, heterocyclyl, aryl, or heteroaryl group is optionally substituted;

with the proviso that the compound is not selected from the group consisting of 5-(N,N-Dimethylsulfamoyl)-N-(5-methyl-1,3-thiazol-2-yl)-2-(pyrrolidin-1-yl)benzamide, 5-(dimethylsulfamoyl)-N-(4-methyl-1,3-thiazol-2-yl)-2-pyrrolidin-1-ylbenzamide, 5-(dimethylsulfamoyl)-2-pyrrolidin-1-yl-N-(1,3-thiazol-2-yl)benzamide, 5-(dimethylsulfamoyl)-N-(5-methyl-1,3,4-thiadiazol-2-yl)-2-pyrrolidin-1-ylbenzamide, 5-(dimethylsulfamoyl)-N-(5-methyl-1H-1,2,4-triazol-3-yl)-2-pyrrolidin-1-ylbenzamide, N-(1,3-benzothiazol-2-yl)-5-(dimethylsulfamoyl)-2-pyrrolidin-1-ylbenzamide, 5-(dimethylsulfamoyl)-N-(4-methoxy-1,3-benzothiazol-2-yl)-2-pyrrolidin-1-ylbenzamide, 5-(dimethylsulfamoyl)-N-(5-methoxy-1,3-benzothiazol-2-yl)-2-pyrrolidin-1-ylbenzamide, 5-(dimethylsulfamoyl)-N-(6-methoxy-1,3-benzothiazol-2-yl)-2-pyrrolidin-1-ylbenzamide, 5-(dimethylsulfamoyl)-N-pyridin-3-yl-2-pyrrolidin-1-ylbenzamide, 5-(dimethylsulfamoyl)-N-pyridin-4-yl-2-pyrrolidin-1-ylbenzamide, 5-(dimethylsulfamoyl)-N-phenyl-2-pyrrolidin-1-ylbenzamide, 5-(dimethylsulfamoyl)-N-(2-meth)ylphenyl)-2-pyrrolidin-1-ylbenzamide, 5-(dimethylsulfamoyl)-N-(4-methylphenyl)-2-pyrrolidin-1-ylbenzamide, 5-(dimethylsulfamoyl)-N-(2-methoxyphenyl)-2-pyrrolidin-1-ylbenzamide, 5-(dimethylsulfamoyl)-N-(4-methoxyphenyl)-2-pyrrolidin-1-ylbenzamide, 5-(dimethylsulfamoyl)-N-(2-fluorophenyl)-2-pyrrolidin-1-ylbenzamide, 5-(dimethylsulfamoyl)-N-(3-fluorophenyl)-2-pyrrolidin-1-ylbenzamide, 5-(dimethylsulfamoyl)-N-(2-chlorophenyl)-2-pyrrolidin-1-ylbenzamide, 5-(dimethylsulfamoyl)-N-(4-bromophenyl)-2-pyrrolidin-1-ylbenzamide, N,N-dimethyl-3-(morpholine-4-carbonyl)-4-pyrrolidin-1-ylbenzenesulfonamide, N-cyclohexyl-5-(dimethylsulfamoyl)-2-pyrrolidin-1-ylbenzamide, 5-(dimethylsulfamoyl)-N,N-dimethyl-2-pyrrolidin-1-ylbenzamide, 5-(diisobutylsulfamoyl)-N-(5-methyl-1,3-thiazol-2-yl)-2-pyrrolidin-1-ylbenzamide, 5-(diethylsulfamoyl)-N-(5-methyl-1,3-thiazol-2-yl)-2-pyrrolidin-1-ylbenzamide, N-(5-methyl-1,3-thiazol-2-yl)-2-pyrrolidin-1-yl-5-pyrrolidin-1-ylsulfonyl benzamide, N-(5-methyl-1,3-thiazol-2-yl)-5-piperidin-1-ylsulfonyl-2-pyrrolidin-1-ylbenzamide, N-(5-methyl-1,3-thiazol-2-yl)-5-morpholin-4-ylsulfonyl-2-pyrrolidin-1-ylbenzamide, N-(5-methyl-1,3-thiazol-2-yl)-5-piperazin-1-ylsulfonyl-2-pyrrolidin-1-ylbenzamide, 5-[methyl(phenyl)sulfamoyl]-N-(5-methyl-1,3-thiazol-2- yl)-2-pyrrolidin-1-ylbenzamide, 5-(benzylsulfamoyl)-N-(5-methyl-1,3-thiazol-2-yl)-2-pyrrolidin-1-ylbenzamide, 5-(dimethylsulfamoyl)-N-(5-methyl-1,3-thiazol-2-yl)-2-piperidin-1-ylbenzamide, 2-(azetidin-1-yl)-5-(dimethylsulfamoyl)-N-(5-methyl-1,3-thiazol-2-yl)benzamide, 5-(dimethylsulfamoyl)-N-(5-methyl-1,3-thiazol-2-yl)-2-piperazin-1-ylbenzamide, 2-(dimethylamino)-5-(dimethylsulfamoyl)-N-(5-methyl-1,3-thiazol-2-yl)benzamide, 2-(diethylamino)-5-(dimethylsulfamoyl)-N-(5-methyl-1,3-thiazol-2-yl)benzamide, 2-cyclopentyl-5-(dimethylsulfamoyl)-N-(5-methyl-1,3-thiazol-2-yl)benzamide, and 3-(dimethylsulfamoyl)-N-(5-methyl-1,3-thiazol-2-yl)benzamide.

In certain embodiments, the compound of formula (I) is a compound of formula (II), or a salt solvate enantiomer, diastereoisomer or tautomer thereof:

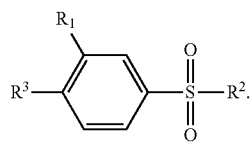

In certain embodiments of formula (I) or formula (II), $R^1$ is selected from the group consisting of

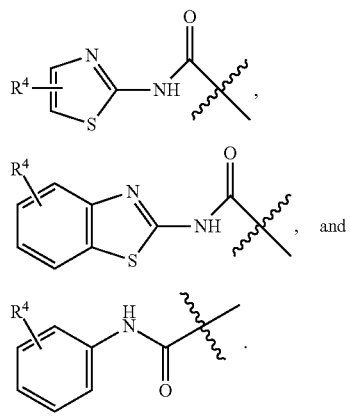

In other embodiments of formula (I) or formula (II), $R^2$ is selected from the group consisting of

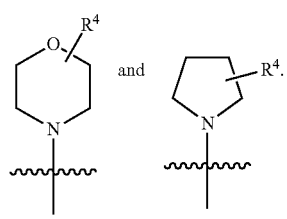

In yet other embodiments of formula (I) or formula (II), $R^3$ is selected from the group consisting of:

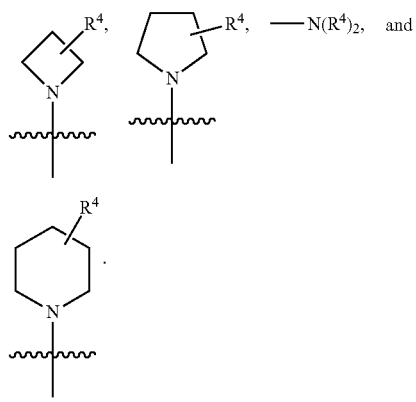

In yet other embodiments of formula (I) or formula (II), $R^1$ is selected from the group consisting of

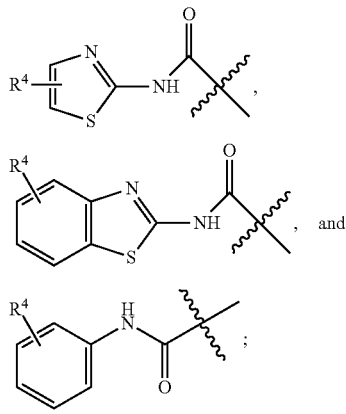

and $R^2$ is selected from the group consisting of

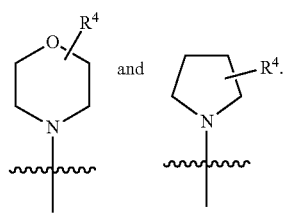

In yet other embodiments of formula (I) or formula (II), $R^1$ is selected from the group consisting of

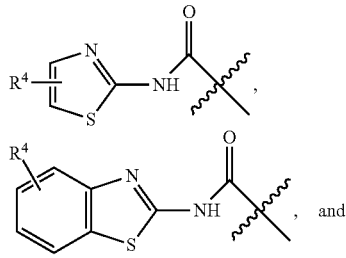

-continued
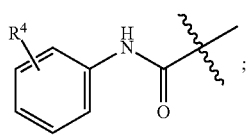
and R³ is selected from the group consisting of
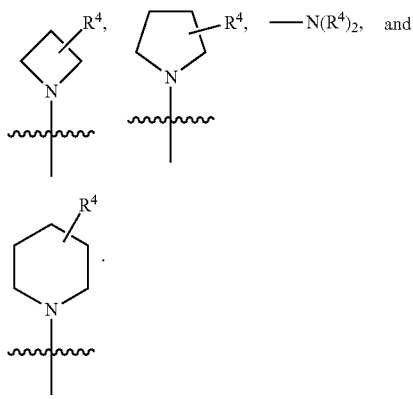
In yet other embodiments of formula (I) or formula (II), R¹ is
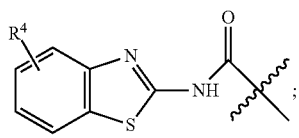
R² is
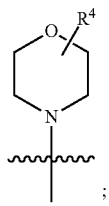
and R³ is
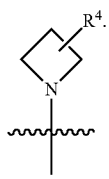
In yet other embodiments of formula (I) or formula (II), R¹ is
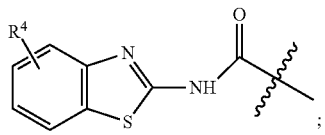
R² is
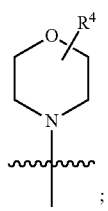
and R³ is
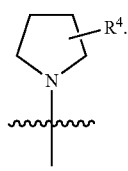
In yet other embodiments of formula (I) or formula (II), R¹ is
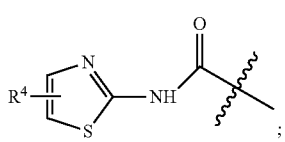
R² is
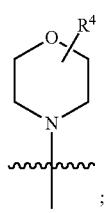
and R³ is
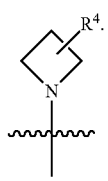

In yet other embodiments of formula (I) or formula (II), R¹ is

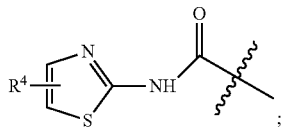
;

R² is

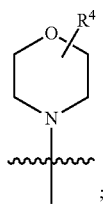
;

and R³ is

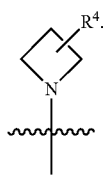
.

In yet other embodiments of formula (I) or formula (II), R¹ is

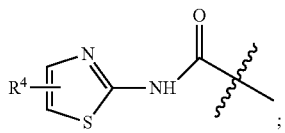
;

R² is —N(R⁴)₂; and R³ is

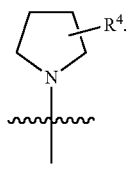
.

The invention further provides a pharmaceutical composition comprising at least one pharmaceutically acceptable carrier and at least one agent selected from the group consisting of a compound of formula (I):

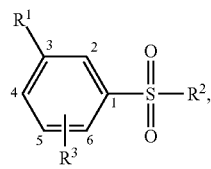

(I)

wherein in (I):

R¹ is selected from the group consisting of

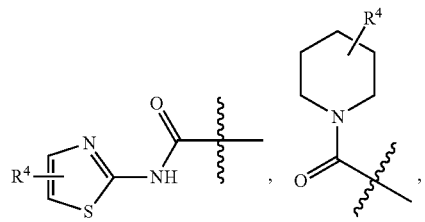

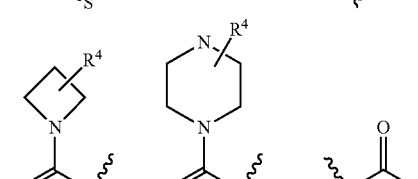

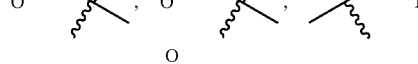

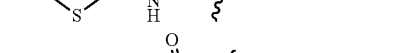

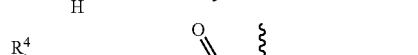

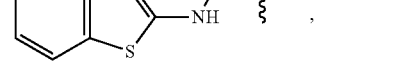

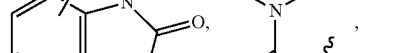

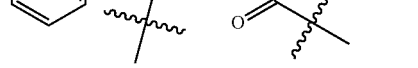

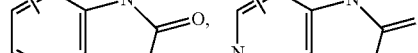

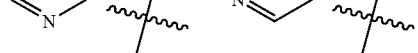

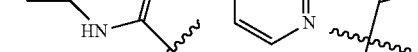

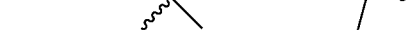

and

-continued

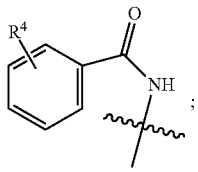

m=1 or 2;
R² is selected from the group consisting of

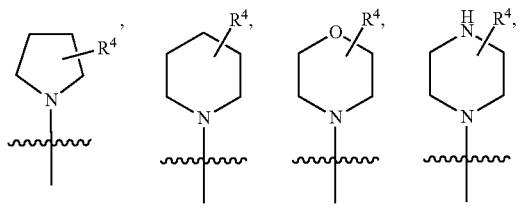

and —N(R⁴)₂;
R³ is selected from the group consisting of

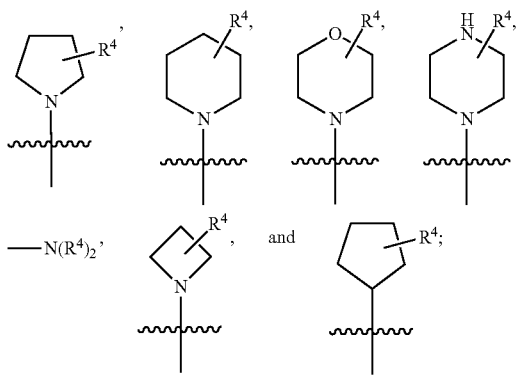

each occurrence of R⁴ is independently selected from the group consisting of H, —(C₁-C₆)alkyl, —(C₃-C₆)cycloalkyl, —(C₁-C₆)haloalkyl, —(C₁-C₆)alkoxy, —(C₃-C₁₀)heterocyclyl, —(C₁-C₆)heteroalkyl, —F, —Cl, —Br, —I, —CN, —NO₂, —OR⁵, —SR⁵, —S(=O)R⁵, —S(=O)₂R⁵, —C(=O)R⁵, —OC(=O)R⁵, —C(=O)OR⁵, aryl, —CH₂-aryl, and —(C₅-C₁₀)heteroaryl, wherein the alkyl, heteroalkyl, cycloalkyl, heterocyclyl, aryl, or heteroaryl group is optionally substituted; and, each occurrence of R¹ is independently selected from the group consisting of H, —(C₁-C₆)alkyl, —(C₁-C₆)heteroalkyl, —(C₃-C₆)cycloalkyl, —(C₃-C₁₀)heterocyclyl, aryl, and —(C₅-C₁₀)heteroaryl, wherein the alkyl, heteroalkyl, cycloalkyl, heterocyclyl, aryl, or heteroaryl group is optionally substituted:

3-benzyl-1-(3-(dimethylamino)propyl)-1-((2-oxo-1,2-dihydroquinolin-3-yl)methyl)urea;
1-(3-(dimethylamino)propyl)-1-((2-oxo-1,2-dihydroquinolin-3-yl)methyl)-3-phenylurea;
3-benzyl-1-((7,8-dimethyl-2-oxo-1,2-dihydroquinolin-3-yl)methyl)-1-(3-(dimethylamino)propyl) urea; and
1-((7,8-dimethyl-2-oxo-1,2-dihydroquinolin-3-yl)methyl)-1-(3-(dimethylamino)propyl)-3-phenylurea.

In certain embodiments, the pharmaceutical composition further comprises at least one additional therapeutic compound that treats or prevents cancer.

The invention further provides a method of inhibiting or disrupting N-linked glycosylation in a cell, the method comprising contacting the cell with an effective amount of at least one agent contemplated within the invention.

The invention further provides a method of preventing or treating a cancer in a subject in need thereof, the method comprising administering to the subject a therapeutically effective amount of at least one agent contemplated within the invention.

In certain embodiments, the at least one agent is selected from the group consisting of 3-benzyl-1-(3-(dimethylamino)propyl)-1-((2-oxo-1,2-dihydroquinolin-3-yl)methyl)urea; 1-(3-(dimethylamino)propyl)-1-((2-oxo-1,2-dihydroquinolin-3-yl)methyl)-3-phenylurea; 3-benzyl-1-((7,8-dimethyl-2-oxo-1,2-dihydroquinolin-3-yl)methyl)-1-(3-(dimethylamino)propyl) urea; 1-((7,8-dimethyl-2-oxo-1,2-dihydroquinolin-3-yl)methyl)-1-(3-(dimethylamino)propyl)-3-phenylurea and a compound of formula (I):

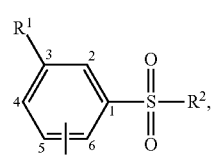

(I)

wherein in (I):

R¹ is selected from the group consisting of

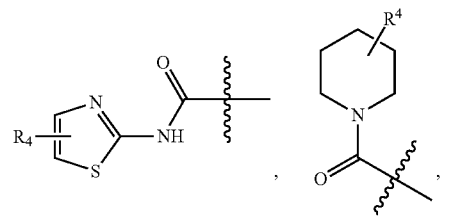

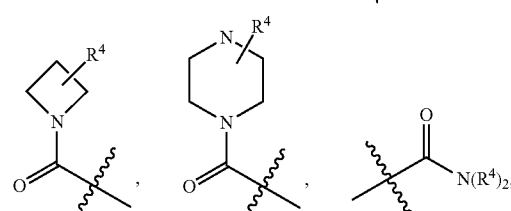

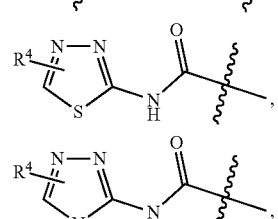

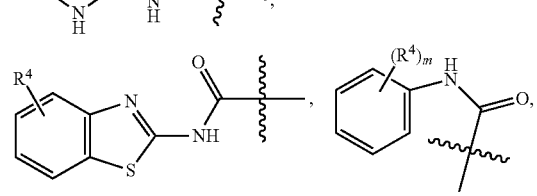

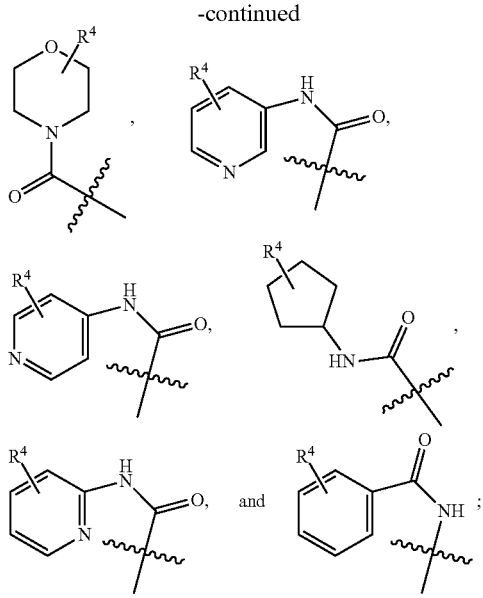

m=1 or 2;
R² is selected from the group consisting of

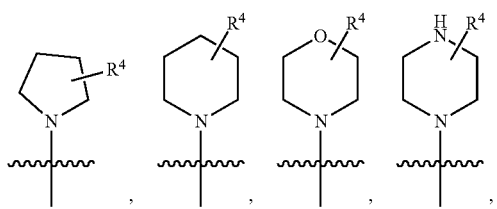

and —N(R⁴)₂;
R³ is selected from the group consisting of

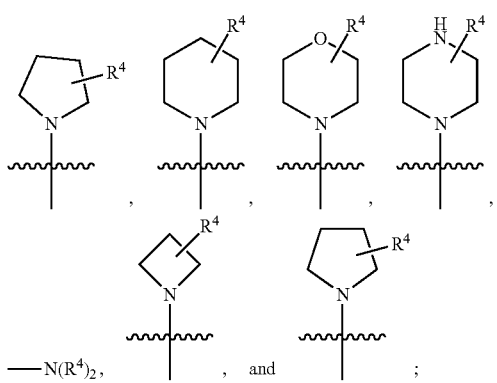

each occurrence of R⁴ is independently selected from the group consisting of H, —($C_1$-$C_6$)alkyl, —($C_3$-$C_6$)cycloalkyl, —($C_1$-$C_6$)haloalkyl, —($C_1$-$C_6$)alkoxy, —($C_3$-$C_{10}$)heterocyclyl, —($C_1$-$C_6$)heteroalkyl, —F, —Cl, —Br, —I, —CN, —NO₂, —OR⁵, —SR⁵, —S(=O)R⁵, —S(=O)₂R⁵, —C(=O)R⁵, —OC(=O)R⁵, —C(=O)OR⁵, aryl, —CH₂-aryl, and —($C_5$-$C_{10}$)heteroaryl, wherein the alkyl, heteroalkyl, cycloalkyl, heterocyclyl, aryl, or heteroaryl group is optionally substituted; and,
each occurrence of R⁵ is independently selected from the group consisting of H, —($C_1$-$C_6$)alkyl, —($C_1$-$C_6$)heteroalkyl, —($C_3$-$C_6$)cycloalkyl, —($C_3$-$C_{10}$)heterocyclyl, aryl, and —($C_5$-$C_{10}$)heteroaryl, wherein the alkyl, heteroalkyl, cycloalkyl, heterocyclyl, aryl, or heteroaryl group is optionally substituted.

In certain embodiments, the agent inhibits or disrupts oligosaccharyltransferase function in the cell. In other embodiments, the agent inhibits or disrupts N-linked glycosylation in a cell from the cancer. In yet other embodiments, the cell is a receptor tyrosine kinase-dependent cancer cell. In yet other embodiments, the cancer is receptor tyrosine kinase-dependent. In yet other embodiments, the agent blocks or inhibits cell surface expression of the receptor tyrosine kinase. In yet other embodiments, the cell comprises a cancer cell selected from the group consisting of non-small cell lung cancer, small cell lung cancer, head and neck squamous cell carcinoma, breast cancer, gastric cancer, cervical cancer, colon cancer, and glioma. In yet other embodiments, the agent causes cell cycle arrest and/or senescence in the cell. In yet other embodiments, the agent blocks or inhibits proliferation of the cell. In yet other embodiments, the cell is in vivo in a mammal. In yet other embodiments, the agent is administered to the mammal. In yet other embodiments, the subject is a human.

In certain embodiments, the subject is further administered at least one additional therapeutic compound that treats or prevents cancer. In other embodiments, the agent and the at least one additional therapeutic compound are co-administered to the subject. In yet other embodiments, the agent and the at least one additional therapeutic compound are coformulated.

In certain embodiments, the cancer is selected from the group consisting of squamous cell cancer, small cell lung cancer, non-small cell lung cancer, vulval cancer, thyroid cancer, adenocarcinoma of the lung and squamous carcinoma of the lung, cancer of the peritoneum, hepatocellular cancer, gastric or stomach cancer, pancreatic cancer, glioma, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney cancer, renal cancer, prostate cancer, hepatic carcinoma, anal carcinoma, penile carcinoma, and head and neck cancer. In other embodiments, the cancer comprises non-small cell lung cancer, small cell lung cancer, head and neck squamous cell carcinoma, breast cancer, gastric cancer, cervical cancer, colon cancer, and glioma.

In certain embodiments, the agent is administered to the subject by at least one route selected from the group consisting of nasal, inhalational, topical, oral, buccal, rectal, pleural, peritoneal, vaginal, intramuscular, subcutaneous, transdermal, epidural, intrathecal and intravenous routes.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIGS. 1A-1D provide a non-limiting overview for the high-throughput screen for inhibitors of N-linked glycosylation. FIG. 1A is a flow diagram illustrating triage strategies and screening results for compound triage. Positive screens are indicated in blue, negative screens are indicated in white, and virtual screens are indicated in light blue. Thresholds for compound advancement are indicated on the right. SD=standard deviation, AC50=50% activating concentration, SAR=structure activity relationships. FIG. 1B illustrates structural activity relationship (SAR) for the aminobenzamidosulfonamide series. The AC40 for each analog is reported for comparison. FIG. 1C is a graph illustrating dose response inhibition of NLG by 5-(N,N-Dimethylsulfamoyl)-N-(5-methylthiazol-2-yl)-2-(pyrrolidin-1-yl)benzamide (NGI-1) as measured by luminescent activity in D54 ERLucT cells. Results are the average of 4 independent experiments. FIG. 1D is a western blot illustrating dose response inhibition of luciferase glycosylation. Glycoforms are identified as 0n-3n.

FIGS. 2A-2I illustrate the finding that NGI-1 blocks OST function. FIG. 2A illustrates the western blots of glycosylated luciferase (Luc) after treatment with 1 µM tunicmaycin (Tn) and 10 µM NGI-1 in CHO-Lec15 and CHO-Lec35 cells with stable expression of ER-LucT. FIG. 2B is a western blot illustrating FACE analysis of lipid linked oligosaccharides (LLOs). FIG. 2C is a series of western blots illustrating the effects of NGI-1 (5 µM) on free oligosaccharides (left panel) and N-linked glycans cleaved from peptides with Peptide-N-Glycosidase F (right panel). Carbohydrate size is indicated with glucose markers (G4-G7). FIG. 2D is a western blot illustrating cell free inhibition of the OST using a rabbit reticulocyte lysate translation system supplemented with canine pancreas rough microsomes (cRM). Saposin-DDK-His6 mRNA was translated for 60 min in the presence of $^{35}S$ methionine and the indicated concentration of NGI-1 or Tn. FIGS. 2E-2F illustrate $^{35}S$ labeling of glycoproteins prosaposin (pSAP) and steroid hormone binding globulin (SHBG) in Hela cells to demonstrate the effect of 10 µM NGI-1 on N-linked glycosylation. FIG. 2E comprises a series of western blots illustrating results from NGI-1 compared to siRNA knockdown of STT3A or STT3B. Glycoforms are represented by 0-5n and 0-2n respectively and average number of glycans per sample is reported for each condition. NC=non-coding siRNA, EH=endoglycosidase H treated. FIG. 2F comprises a series of western blots illustrating Hela cells treated with NGI-1 for 24 hrs prior to addition of the $^{35}S$ label, during labeling, or both to demonstrate reversibility of the inhibitor. FIGS. 2G-2H: Dose response and quantitation of NGI-1 effect on pSAP (squares) and SHBG glycosylation (circles). FIG. 2I: CETSA for subunits of the OST in 293T cells treated with and without 100 µM NGL-1 for 30 min. The 0 denotes no thermal treatment. Each panel is representative of 2 independent experiments.

FIG. 3A illustrates EGFR western blots from H3255 treated with or without 10 µM NGI-1 for 24 h. Molecular weight size shifts are compared to PNGase digestion and tunicamycin treatment alone. FIG. 3B illustrates EGFR localization in H3255 cells after 24 h 10 µM NGI-1 treatment analyzed by western blot. Plasma membrane proteins present on the surface of H3255 cells were biotinylated using a non-permeable form of biotin, sulfo-NHS—SS-biotin, and precipitated by streptavidin agarose beads. Biotin-labeled plasma membrane proteins and the fraction of non-biotinylated proteins were subjected to SDS-PAGE and analyzed by western blot against EGFR. FIG. 3C illustrates EGFR localization in H3255 cells after 24 h 10 µM NGI-1 treatment analyzed by confocal microscopy. H3255 cells were subjected to immunofluorescence for EGFR protein (red) counterstained with (CRT; green) and colocalization was determined by confocal microscopy. Nuclei were counterstained with ToPro3 (cyan). Representative confocal central sections are displayed. Bar, 10 µm. FIG. 3D illustrates quantification of colocalization using Image J Colormap Software. Color scale displays either a positive (red and yellow) or negative (blue and green) correlation. The bar graphs indicate the overlap coefficient between EGFR and CRT for each condition and average results from three independent experiments are presented. ITB1 localization after 10 µM NGI-1 for 48 h analyzed by (FIG. 3E) surface biotinylation (FIG. 3F) confocal microscopy (green). Results for each panel are representative of at least three independent experiments. Asterisk indicates a significant difference p<0.05.

FIG. 4A illustrates western blot analysis of EGFR phosphorylation (Y1173) and gel mobility in PC9 (EGFR-mutant) and A549 (k-ras mutant) NSCLC cells after 10 µM NGI-1 treatment for 24 h. The filled arrow indicate the fully glycosylated EGFR while the open arrow shows the deglycosylated form. Actin expression was used as a control for protein loading. FIG. 4B illustrates MTT assays results of PC9 following treatment with 10 µM NGI-1 or 1 µM tunicamycin for a total of 5 d. Relative proliferation id reported in fold increase from day 0. FIG. 4C illustrates MTT assays results of A549 following treatment with 10 µM NGI-1 or 1 µM tunicamycin for a total of 5 d. Relative proliferation id reported in fold increase from day 0. FIG. 4D illustrates protein phosphorylation profiles of PC9 cells analyzed by phospho-protein array to assess the response of PC9 to 10 µM NGI-1 for 24 h. FIG. 4E illustrates protein phosphorylation profiles of A549 cells analyzed by phospho-protein array to assess the response of A549 to 10 µM NGI-1 for 24 h. FIG. 4F illustrates western blot analysis of FGFR phosphorylation (Y653/654) and gel mobility for H1581 (TKI sensitive) and H2444 (TKI insensitive) NSCLC cell lines. The filled arrow indicate the fully glycosylated FGFR while the open arrow shows the deglycosylated form. FIG. 4G illustrates MTT assays for H1581 cells treated with 10 µM NGI-1 for 5 d. Asterisk (***) indicates a significant difference p<0.001 for MTT. FIG. 4H illustrates MTT assays for H2444 cells treated with 10 µM NGI-1 for 5 d.

FIG. 5A illustrates cell cycle distribution of PC9 cells after 24 h NGI-1 treatment for 24 h determined by flow cytometry. PC9 cells undergo G1 arrest in response to NGI-1. FIG. 5B illustrates cell cycle distribution of A549 cells after 24 h NGI-1 treatment for 24 h determined by flow cytometry. FIG. 5C illustrates western blot time course of cyclin D1 expression in PC9 and A549 cells after NGI-1 treatment. FIG. 5D illustrates quantitative real-time PCR analysis of PC9 and A549 cells. A time course of cyclin D1 expression levels relative to GAPDH is represented. FIG. 5E illustrates western blots of p21 induction over 24 h after NGI-1 treatment in PC9 and A549 cells. FIG. 5F illustrates senescence of PC9 cells explored by: cell autofluorescence, measured by flow cytometry using a detector for PE/YFP; lipofuscin accumulation, detected by confocal laser scanning microscopy using an excitation laser of 405 nm with acquired signals from spectrums of yellow 575-620 nm; and morphology changes, enlarged vs. flattened. Error bars represent standard deviation (SD). Significance was calculated using a T test (*p<0.05. **p<0.01). FIG. 5G illustrates senescence of A549 cells explored by: cell autofluorescence, measured by flow cytometry using a detector for PE/YFP; lipofuscin accumulation, detected by confocal laser scanning microscopy using an excitation laser of 405 nm with acquired signals from spectrums of yellow 575-620 nm; and morphology changes, enlarged vs. flattened. Error bars represent standard deviation (SD). Significance was calculated using an ANOVA test (*p<0.05, **p <0.01).

FIGS. 6A-6C illustrate the finding that NGI-1 disrupts EGFR glycosylation and cell surface expression. FIG. 6A illustrates the finding that plasma membrane proteins present on the surface of HCC827 cells were biotinylated using a non-permeable form of biotin, sulfo-NHS—SS-biotin, and precipitated by streptavidin agarose beads. Biotin-labeled plasma membrane proteins and the fraction of non-biotinylated proteins were subjected to SDSPAGE and analyzed by WB against EGFR. FIG. 6B illustrates the finding that HCC827 cells were subjected to immunofluorescence for EGFR protein (red) counterstained with (CRT; green) and co-localization was determined by confocal microscopy. Nuclei were counterstained with ToPro3 (cyan). Representative confocal central sections are displayed. Bar, 10 μm. FIG. 6C illustrates quantification of colocalization using Image J Colormap Software; the color scale displays either a positive (red and yellow) or negative (blue and green) correlation. The bar graphs indicate the overlap coefficient between EGFR and CRT for each condition and average results from three independent experiments are presented p<0.05.

FIG. 7A illustrates MTT assays to determine the effects of NGI-1 on growth of H3255 cells. FIG. 7B illustrates MIT assays to determine the effects of NGI-1 on growth of HCC827 cells. EGFR kinase domain mutant cell lines H3255 and HCC827 cells were untreated or treated with 10 μM NGI-1 for 5 d. NGI-1 treatment reduced proliferation of H3255 by >45% (p<0.05) and HCC827 by >45% (p<0.05). FIG. 7C illustrates cell cycle distribution of H3255 after 24 h NGI-1 treatment for 24 h determined by flow cytometry. FIG. 7D illustrates cell cycle distribution of HCC827 after 24 h NGI-1 treatment for 24 h determined by flow cytometry. Both cell lines undergo G1 arrest in response to NGI-1, H3255 p<0.05 and HCC827 p<0.01.

DETAILED DESCRIPTION OF THE INVENTION

Figure 1A:
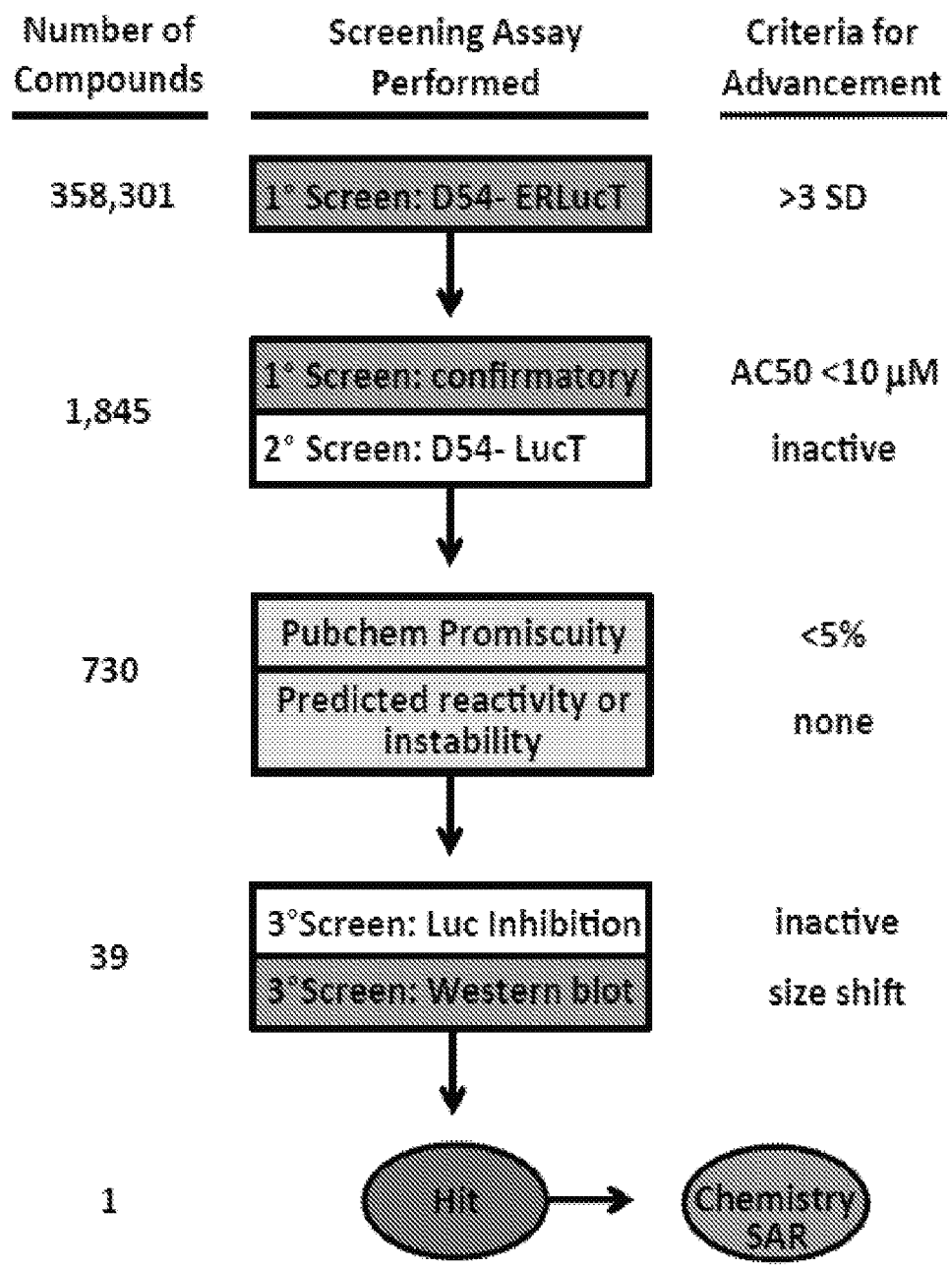

The present invention relates to the unexpected discovery of novel small-molecule inhibitors of N-linked glycosylation and methods of using same.

In certain embodiments, the compounds of the present invention inhibit N-linked glycosylation. In other embodiments, the compounds of the invention inhibit oligosaccharyltransferase (OST). In yet other embodiments, the compounds of the present invention binds the multisubunit OST complex, reducing or inhibiting its activity. In yet other embodiments, the compounds of the present invention induces G1 arrest and senescence in RTK-dependent cell lines. In yet other embodiments, the compounds of the present invention inhibit N-linked glycosylation of proteins synthesized in vitro and/or in cell culture.

The present invention also relates to a method for treating or preventing a disease associated with N-linked glycosylation in a mammal by administering to the mammal a therapeutically effective amount of a N-linked glycosylation inhibitor. In certain embodiments, the disease is a cancer. In other embodiments, the diseases is non-small cell lung cancer, small cell lung cancer, head and neck squamous cell carcinoma, breast cancer, gastric cancer, cervical cancer, colon cancer, and glioma.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, specific methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal", when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type might be abnormal for a different cell or tissue type.

A disease or disorder is "alleviated" if the severity of a symptom of the disease or disorder, the frequency with which such a symptom is experienced by a patient, or both, is reduced.

The terms "cancer" refers to the physiological condition in a subject typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small cell lung cancer, non-small cell lung cancer ("NSCLC"), vulval cancer, thyroid cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, hepatic carcinoma, anal carcinoma, penile carcinoma, as well as head and neck cancer.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount", "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "efficacy" refers to the maximal effect ($E_{max}$) achieved within an assay.

As used herein, the term "OST" refers to oligosaccharyltransferase.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids or bases, including inorganic acids or bases, organic acids or bases, solvates, hydrates, or clathrates thereof.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate).

Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985. Easton, Pa.), which is incorporated herein by reference.

The terms "patient", "subject", or "individual" are used interchangeably herein, and refer to any animal, or cells thereof whether in vitro or in situ, amenable to the methods described herein. In a non-limiting embodiment, the patient, subject or individual is a human.

As used herein, the term "potency" refers to the dose needed to produce half the maximal response ($ED_{50}$).

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

A "therapeutic" treatment is a treatment administered to a subject who exhibits signs of pathology, for the purpose of diminishing or eliminating those signs.

As used herein, the term "alkyl", by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "substituted alkyl" means alkyl as defined above, substituted by one, two or three substituents selected from the group consisting of halogen, —OH, alkoxy, —$NH_2$, —$N(CH_3)_2$, —C(=O)OH, trifluoromethyl, —C≡N, —C(=O)O($C_1$-$C_4$)alkyl, —C(=O)$NH_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "haloalkyl" means alkyl as defined above, substituted by one, two or three substituents selected from the group consisting of F, Cl, Br, and I.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized or substituted. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, —NH—($CH_2$)$_m$—OH (m=1-6), —N($CH_3$)—($CH_2$)$_m$—OH (m=1-6), —NH—($CH_2$)$_m$—$OCH_3$ (m=1-6), and —$CH_2CH_2$—S(=O)—$CH_3$. Up to two heteroatoms may be consecutive, such as, for example, —$CH_2$—NH—$OCH_3$, or —$CH_1$—$CH_2$—S—S—$CH_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e. skeletal atoms) is a carbon atom. In certain embodiments, the cycloalkyl group is saturated or partially unsaturated. In other embodiments, the cycloalkyl group is fused with an aromatic ring. Cycloalkyl groups include groups having from 3 to 10 ring atoms. Illustrative examples of cycloalkyl groups include, but are not limited to, the following moieties:

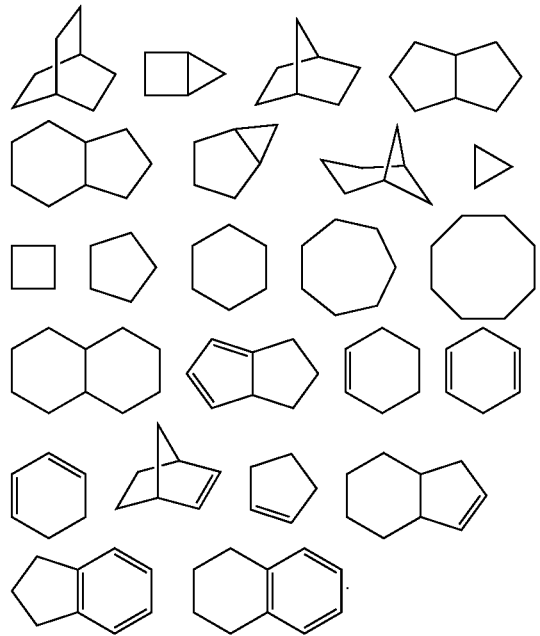

Monocyclic cycloalkyls include, but are not limited to, cyclopropyl, cyclobutvl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbomane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In certain embodiments, each heterocycloalkyl group has from 4 to 10 atoms in its ring system, with the proviso that the ring of said group does not contain two adjacent O or S atoms. In other embodiments, the heterocycloalkyl group is fused with an aromatic ring. In certain embodiments, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

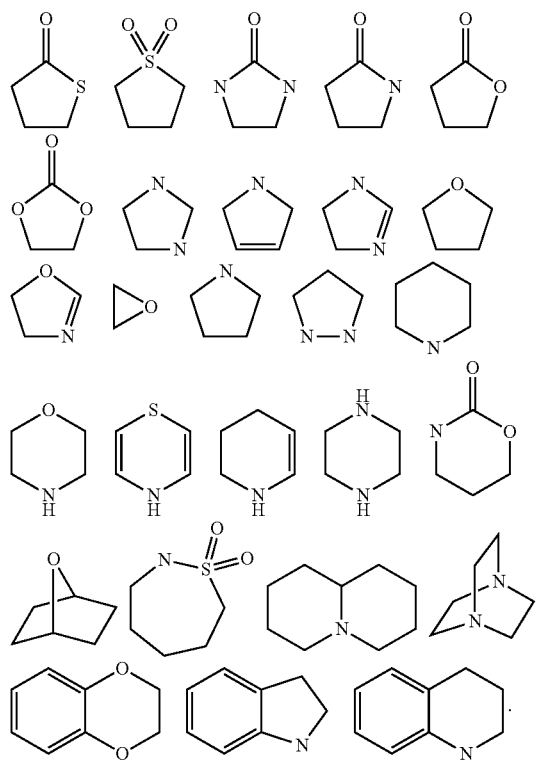

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl", employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "aryl-($C_1$-$C_3$)alkyl" means a functional group wherein a one- to three-carbon alkylene chain is attached to an aryl group, e.g., —CH$_2$CH$_2$-phenyl. Preferred is aryl-CH— and aryl-CH(CH$_3$)—. The term "substituted aryl-($C_1$-$C_3$)alkyl" means an aryl-($C_1$-$C_3$)alkyl functional group in which the aryl group is substituted. Preferred is substituted aryl(CH$_2$)—. Similarly, the term "heteroaryl-($C_1$-$C_3$)alkyl" means a functional group wherein a one to three carbon alkylene chain is attached to a heteroaryl group, e.g., —CH$_2$CH$_2$-pyridyl. Preferred is heteroaryl-(CH$_2$)—. The term "substituted heteroaryl-($C_1$-$C_3$) alkyl" means a heteroaryl-($C_1$-$C_3$)alkyl functional group in which the heteroaryl group is substituted. Preferred is substituted heteroaryl-(CH$_2$)—.

As used herein, the term "heteroaryl" or "heteroaromatic" refers to a heterocycle having aromatic character. A polycyclic heteroaryl may include one or more rings that are partially saturated. Examples include the following moieties:

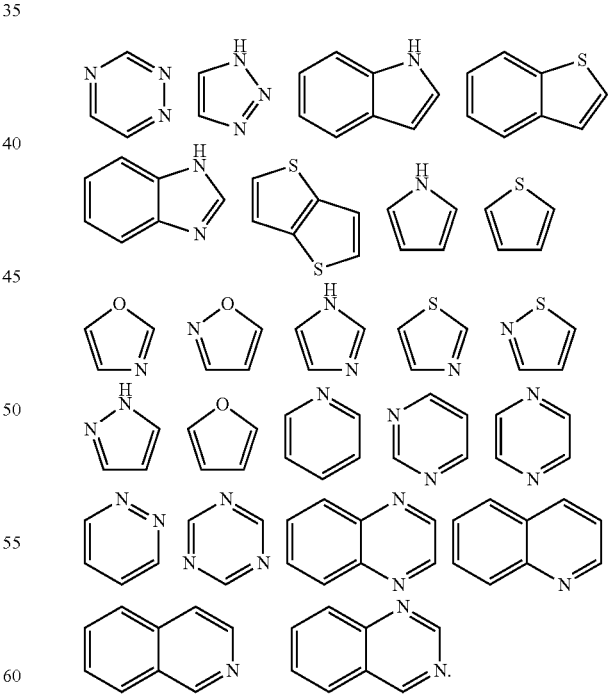

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two.

As used herein, the term "optionally substituted" means that the referenced group may be substituted or unsubstituted. In certain embodiments, the referenced group is optionally substituted with zero substituents, i.e., the referenced group is unsubstituted. In other embodiments, the referenced group is optionally substituted with one or more additional group(s) individually and independently selected from groups described herein.

In certain embodiments, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH[substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In other embodiments, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet other embodiments, the substituents are independently selected from the group consisting of C$_{1-6}$alkyl, C$_{1-6}$ alkoxy, halo, acetamido, and nitro. As used herein, where a substituent is an alkyl or alkoxy group, the carbon chain may be branched, straight or cyclic, with straight being preferred.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds

The compounds of the present invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of formula (I), or a salt, solvate or N-oxide thereof:

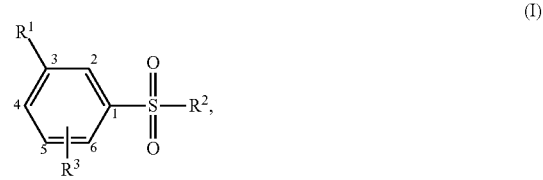

wherein in (I):

R$^1$ is selected from the group consisting of

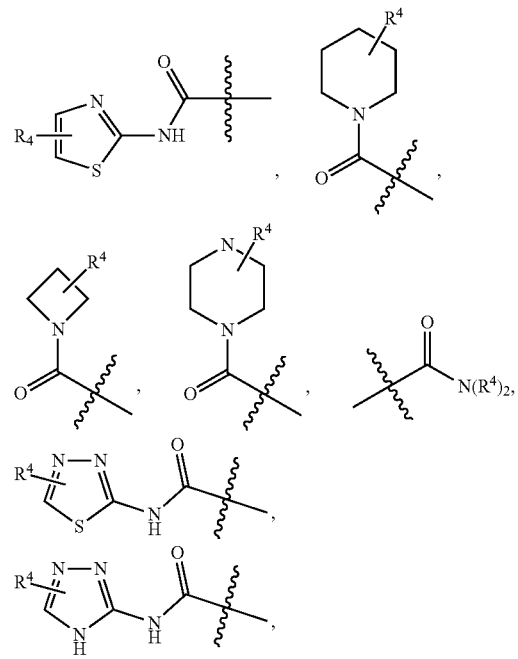

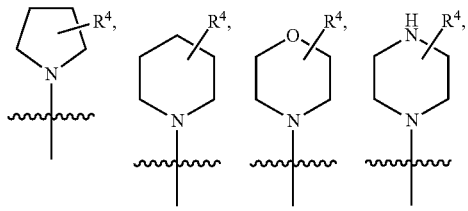

m=1 or 2;
R² is selected from the group consisting of

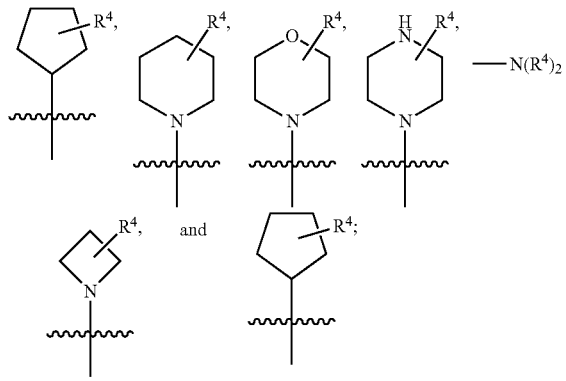

and —N(R⁴)₂;
R³ is selected from the group consisting of each occurrence of R⁴ is independently selected from the group consisting of H, —(C₁-C₆)alkyl, —(C₃-C₆)cycloalkyl, —(C₁-C₆)haloalkyl, —(C₁-C₆)alkoxy, —(C₃-C₁₀)heterocyclyl, —(C₁-C₆)heteroalkyl, —F, —Cl, —Br, —I, —CN, —NO₂, —OR⁵, —SR⁵, —S(=O)R⁵, —S(=O)₂R⁵, —C(=O)R⁵, —OC(=O)R⁵, —C(=O)OR⁵, aryl, —CH₂-aryl, and —(C₅-C₁₀)heteroaryl, wherein the alkyl, heteroalkyl, cycloalkyl, heterocyclyl, aryl, or heteroaryl group is optionally substituted; and, each occurrence of R⁵ is independently selected from the group consisting of H, —(C₁-C₆)alkyl, —(C₁-C₆)heteroalkyl, —(C₃-C₆)cycloalkyl, —(C₃-C₁₀)heterocyclyl, aryl, and —(C₅-C₁₀)heteroaryl, wherein the alkyl, heteroalkyl, cycloalkyl, heterocyclyl, aryl, or heteroaryl group is optionally substituted.

In certain embodiments, the compound of the invention is 5-(N,N-Dimethylsulfamoyl)-N-(5-methyl-1,3-thiazol-2-yl)-2-(pyrrolidin-1-yl)benzamide, or a salt, solvate or N-oxide thereof. In other embodiments, the compound of the invention is 5-(dimethylsulfamoyl)-N-(4-methyl-1,3-thiazol-2-yl)-2-pyrrolidin-1-ylbenzamide, or a salt, solvate or N-oxide thereof. In yet other embodiments, the compound of the invention is 5-(dimethylsulfamoyl)-2-pyrrolidin-1-yl-N-(1,3-thiazol-2-yl)benzamide, or a salt, solvate or N-oxide thereof. In yet other embodiments, the compound of the invention is 5-(dimethylsulfamoyl)-N-(5-methyl-1,3,4-thiadiazol-2-yl)-2-pyrrolidin-1-ylbenzamide, or a salt, solvate or N-oxide thereof. In yet other embodiments, the compound of the invention is 5-(dimethylsulfamoyl)-N-(5-methyl-1H-1,2,4-triazol-3-yl)-2-pyrrolidin-1-ylbenzamide, or a salt, solvate or N-oxide thereof. In yet other embodiments, the compound of the invention is N-(1,3-benzothiazol-2-yl)-5-(dimethylsulfamoyl)-2-pyrrolidin-1-ylbenzamide, or a salt, solvate or N-oxide thereof. In yet other embodiments, the compound of the invention is 5-(dimethylsulfamoyl)-N-(4-methoxy-1,3-benzothiazol-2-yl)-2-pyrrolidin-1-ylbenzamide, or a salt, solvate or N-oxide thereof. In yet other embodiments, the compound of the invention is 5-(dimethylsulfamoyl)-N-(5-methoxy-1,3-benzothiazol-2-yl)-2-pyrrolidin-1-ylbenzamide, or a salt, solvate or N-oxide thereof. In yet other embodiments, the compound of the invention is 5-(dimethylsulfamoyl)-N-(6-methoxy-1,3-benzothiazol-2-yl)-2-pyrrolidin-1-ylbenzamide, or a salt, solvate or N-oxide thereof. In yet other embodiments, the compound of the invention is 5-(dimethylsulfamoyl)-N-pyridin-3-yl-2-pyrrolidin-1-ylbenzamide, or a salt, solvate or N-oxide thereof. In yet other embodiments, the compound of the invention is 5-(dimethylsulfamoyl)-N-pyridin-4-yl-2-pyrrolidin-1-ylbenzamide, or a salt, solvate or N-oxide thereof. In yet other embodiments, the compound of the invention is 5-(dimethylsulfamoyl)-N-phenyl-2-pyrrolidin-1-ylbenzamide, or a salt, solvate or N-oxide thereof. In yet other embodiments, the compound of the invention is 5-(dimethylsulfamoyl)-N-(2-methylphenyl)-2-pyrrolidin-1-ylbenzamide, or a salt, solvate or N-oxide thereof. In yet other embodiments, the compound of the invention is 5-(dimethylsulfamoyl)-N-(4-methylphenyl)-2-pyrrolidin-1-ylbenzamide, or a salt, solvate or N-oxide thereof. In yet other embodiments, the compound of the invention is 5-(dimethylsulfamoyl)-N-(2-methoxyphenyl)-2-pyrrolidin-1-ylbenzamide, or a salt, solvate or N-oxide thereof. In yet other embodiments, the compound of the invention is 5-(dimethylsulfamoyl)-N-(4-methoxyphenyl)-2-pyrrolidin-1-ylbenzamide, or a salt, solvate or N-oxide thereof. In yet other embodiments, the compound of the invention is 5-(dimethylsulfamoyl)-N-(2-fluorophenyl)-2-pyrrolidin-1-ylbenzamide, or a salt, solvate or N-oxide thereof. In yet other embodiments, the compound of the invention is 5-(dimethylsulfamoyl)-N-(3-fluorophenyl)-2-pyrrolidin-1-ylbenzamide, or a salt, solvate or N-oxide thereof. In yet other embodiments, the compound of the invention is 5-(dimethylsulfamoyl)-N-(2-chlorophenyl)-2- pyrrolidin-1-ylbenzamide, or a salt, solvate or N-oxide thereof. In yet other embodiments, the compound of the invention is 5-(dimethylsulfamoyl)-N-(4-bromophenyl)-2-pyrrolidin-1-ylbenzamide, or a salt, solvate or N-oxide thereof. In yet other embodiments, the compound of the invention is N, N-dimethyl-3-(morpholine-4-carbonyl)-4-pyrrolidin-1-ylbenzenesulfonamide, or a salt, solvate or N-oxide thereof. In yet other embodiments, the compound of the invention is N-cyclohexyl-5-(dimethylsulfamoyl)-2-pyrrolidin-1-ylbenzamide, or a salt, solvate or N-oxide thereof. In yet other embodiments, the compound of the invention is 5-(dimethylsulfamoyl)-N, N-dimethyl-2-pyrrolidin-1-ylbenzamide, or a salt, solvate or N-oxide thereof. In yet other embodiments, the compound of the invention is 5-(diisobutylsulfamoyl)-N-(5-methyl-1,3-thiazol-2-yl)-2-pyrrolidin-1-ylbenzamide, or a salt, solvate or N-oxide thereof. In yet other embodiments, the compound of the invention is 5-(diethylsulfamoyl)-N-(5-methyl-1,3-thiazol-2-yl)-2-pyrrolidin-1-ylbenzamide, or a salt, solvate or N-oxide thereof. In yet other embodiments, the compound of the invention is N-(5-methyl-1,3-thiazol-2-yl)-2-pyrrolidin-1-yl-5-pyrrolidin-1-ylsulfonyl benzamide, or a salt, solvate or N-oxide thereof. In yet other embodiments, the compound of the invention is N-(5-methyl-1,3-thiazol-2-yl)-5-piperidin-1-ylsulfonyl-2-pyrrolidin-1-ylbenzamide, or a salt, solvate or N-oxide thereof. In yet other embodiments, the compound of the invention is N-(5-methyl-1,3-thiazol-2-yl)-5-morpholin-4-ylsulfonyl-2-pyrrolidin-1-ylbenzamide, or a salt, solvate or N-oxide thereof. In yet other embodiments, the compound of the invention is N-(5-methyl-1,3-thiazol-2-yl)-5-piperazin-1-ylsulfonyl-2-pyrrolidin-1-ylbenzamide, or a salt, solvate or N-oxide thereof. In yet other embodiments, the compound of the invention is 5-[methyl(phenyl)sulfamoyl]-N-(5-methyl-1,3-thiazol-2-yl)-2-pyrrolidin-1-ylbenzamide, or a salt, solvate or N-oxide thereof. In yet other embodiments, the compound of the invention is 5-(benzylsulfamoyl)-N-(5-methyl-1,3-thiazol-2-yl)-2-pyrrolidin-1-ylbenzamide, or a salt, solvate or N-oxide thereof. In yet other embodiments, the compound of the invention is 5-(dimethylsulfamoyl)-N-(5-methyl-1,3-thiazol-2-yl)-2-piperidin-1-ylbenzamide, or a salt, solvate or N-oxide thereof. In yet other embodiments, the compound of the invention is 2-(azetidin-1-yl)-5-(dimethylsulfamoyl)-N-(5-methyl-1,3-thiazol-2-yl)benzamide, or a salt, solvate or N-oxide thereof. In yet other embodiments, the compound of the invention is 5-(dimethylsulfamoyl)-N-(5-methyl-1,3-thiazol-2-yl)-2-piperazin-1-ylbenzamide, or a salt, solvate or N-oxide thereof. In yet other embodiments, the compound of the invention is 2-(dimethylamino)-5-(dimethylsulfamoyl)-N-(5-methyl-1,3-thiazol-2-yl)benzamide, or a salt, solvate or N-oxide thereof. In yet other embodiments, the compound of the invention is 2-(diethylamino)-5-(dimethylsulfamoyl)-N-(5-methyl-1,3-thiazol-2-yl)benzamide, or a salt, solvate or N-oxide thereof. In yet other embodiments, the compound of the invention is 2-cyclopentyl-5-(dimethylsulfamoyl)-N-(5-methyl-1,3-thiazol-2-yl)benzamide, or a salt, solvate or N-oxide thereof. In yet other embodiments, the compound of the invention is 3-(dimethylsulfamoyl)-N-(5-methyl-1,3-thiazol-2-yl)benzamide, or a salt, solvate or N-oxide thereof. In yet other embodiments, the compound of the invention is 4-methyl-N-(5-(morpholinosulfonyl)-2-(pyrrolidin-1-yl)phenyl)benzamide, or a salt, solvate or N-oxide thereof. In yet other embodiments, the compound of the invention is 3-methyl-N-(5-(morpholinosulfonyl)-2-(pyrrolidin-1-yl)phenyl)benzamide, or a salt, solvate or N-oxide thereof. In yet other embodiments, the compound of the invention is 5-(N,N-dimethylsulfamoyl)-N-(3-(N,N-dimethylsulfamoyl)-4-methylphenyl)-2-(pyrrolidin-1-yl)benzamide, or a salt, solvate or N-oxide thereof. In yet other embodiments, the compound of the invention is 5-(N,N-dimethylsulfamoyl)-N-(3-fluoro-4-methylphenyl)-2-(pyrrolidin-1-yl)benzamide, or a salt, solvate or N-oxide thereof.

In certain embodiments, the compound of the invention is not 5-(N,N-Dimethylsulfamoyl)-N-(5-methyl-1,3-thiazol-2-yl)-2-(pyrrolidin-1-yl)benzamide, or a salt, solvate or N-oxide thereof. In other embodiments, the compound of the invention is not 5-(dimethylsulfamoyl)-N-(4-methyl-1,3-thiazol-2-yl)-2-pyrrolidin-1-ylbenzamide, or a salt, solvate or N-oxide thereof. In yet other embodiments, the compound of the invention is not 5-(dimethylsulfamoyl)-2-pyrrolidin-1-yl-N-(1,3-thiazol-2-yl)benzamide, or a salt, solvate or N-oxide thereof. In yet other embodiments, the compound of the invention is not 5-(dimethylsulfamoyl)-N-(5-methyl-1,3,4-thiadiazol-2-yl)-2-pyrrolidin-1-ylbenzamide, or a salt, solvate or N-oxide thereof. In yet other embodiments, the compound of the invention is not 5-(dimethylsulfamoyl)-N-(5-methyl-1H-1,2,4-triazol-3-yl)-2-pyrrolidin-1-ylbenzamide, or a salt, solvate or N-oxide thereof. In yet other embodiments, the compound of the invention is not N-(1,3-benzothiazol-2-yl)-5-(dimethylsulfamoyl)-2-pyrrolidin-1-ylbenzamide, or a salt, solvate or N-oxide thereof. In yet other embodiments, the compound of the invention is not 5-(dimethylsulfamoyl)-N-(4-methoxy-1,3-benzothiazol-2-yl)-2-pyrrolidin-1-ylbenzamide, or a salt, solvate or N-oxide thereof. In yet other embodiments, the compound of the invention is not 5-(dimethylsulfamoyl)-N-(5-methoxy-1,3-benzothiazol-2-yl)-2-pyrrolidin-1-ylbenzamide, or a salt, solvate or N-oxide thereof. In yet other embodiments, the compound of the invention is not 5-(dimethylsulfamoyl)-N-(6-methoxy-1,3-benzothiazol-2-yl)-2-pyrrolidin-1-ylbenzamide, or a salt, solvate or N-oxide thereof. In yet other embodiments, the compound of the invention is not 5-(dimethylsulfamoyl)-N-pyridin-3-yl-2-pyrrolidin-1-ylbenzamide, or a salt, solvate or N-oxide thereof. In yet other embodiments, the compound of the invention is not 5-(dimethylsulfamoyl)-N-pyridin-4-yl-2-pyrrolidin-1-ylbenzamide, or a salt, solvate or N-oxide thereof. In yet other embodiments, the compound of the invention is not 5-(dimethylsulfamoyl)-N-phenyl-2-pyrrolidin-1-ylbenzamide, or a salt, solvate or N-oxide thereof. In yet other embodiments, the compound of the invention is not 5-(dimethylsulfamoyl)-N-(2-methylphenyl)-2-pyrrolidin-1-ylbenzamide, or a salt, solvate or N-oxide thereof. In yet other embodiments, the compound of the invention is not 5-(dimethylsulfamoyl)-N-(4-methylphenyl)-2-pyrrolidin-1-ylbenzamide, or a salt, solvate or N-oxide thereof. In yet other embodiments, the compound of the invention is not 5-(dimethylsulfamoyl)-N-(2-methoxyphenyl)-2-pyrrolidin-1-ylbenzamide, or a salt, solvate or N-oxide thereof. In yet other embodiments, the compound of the invention is not 5-(dimethylsulfamoyl)-N-(4-methoxyphenyl)-2-pyrrolidin-1-ylbenzamide, or a salt, solvate or N-oxide thereof. In yet other embodiments, the compound of the invention is not 5-(dimethylsulfamoyl)-N-(2-fluorophenyl)-2-pyrrolidin-1-ylbenzamide, or a salt, solvate or N-oxide thereof. In yet other embodiments, the compound of the invention is not 5-(dimethylsulfamoyl)-N-(3-fluorophenyl)-2-pyrrolidin-1-ylbenzamide, or a salt, solvate or N-oxide thereof. In yet other embodiments, the compound of the invention is not 5-(dimethylsulfamoyl)-N-(2-chlorophenyl)-2-pyrrolidin-1-ylbenzamide, or a salt, solvate or N-oxide thereof. In yet other embodiments, the compound of the invention is not 5-(dimethylsulfamoyl)-N-(4-bromophenyl)-2-pyrrolidin-1-ylbenzamide, or a salt, solvate or N-oxide thereof. In yet other embodiments, the compound of the invention is not N,N-dimethyl-3-(morpholine-4-carbonyl)-4-pyrrolidin-1-ylbenzenesulfonamide, or a salt, solvate or N-oxide thereof. In yet other embodiments, the compound of the invention is not N-cyclohexyl-5-(dimethylsulfamoyl)-2-pyrrolidin-1-ylbenzamide, or a salt, solvate or N-oxide thereof. In yet other embodiments, the compound of the invention is not 5-(dimethylsulfamoyl)-N,N-dimethyl-2-pyrrolidin-1-ylbenzamide, or a salt, solvate or N-oxide thereof. In yet other embodiments, the compound of the invention is not 5-(diisobutylsulfamoyl)-N-(5-methyl-1,3-thiazol-2-yl)-2-pyrrolidin-1-ylbenzamide, or a salt, solvate or N-oxide thereof. In yet other embodiments, the compound of the invention is not 5-(diethylsulfamoyl)-N-(5-methyl-1,3-thiazol-2-yl)-2-pyrrolidin-1-ylbenzamide, or a salt, solvate or N-oxide thereof. In yet other embodiments, the compound of the invention is not N-(5-methyl-1,3-thiazol-2-yl)-2-pyrrolidin-1-yl-5-pyrrolidin-1-ylsulfonyl benzamide, or a salt, solvate or N-oxide thereof. In yet other embodiments, the compound of the invention is not N-(5-methyl-1,3-thiazol-2-yl)-5-piperidin-1-ylsulfonyl-2-pyrrolidin-1-ylbenzamide, or a salt, solvate or N-oxide thereof. In yet other embodiments, the compound of the invention is not N-(5-methyl-1,3-thiazol-2-yl)-5-morpholin-4-ylsulfonyl-2-pyrrolidin-1-ylbenzamide, or a salt, solvate or N-oxide thereof. In yet other embodiments, the compound of the invention is not N-(5-methyl-1,3-thiazol-2-yl)-5-piperazin-1-ylsulfonyl-2-pyrrolidin-1-ylbenzamide, or a salt, solvate or N-oxide thereof. In yet other embodiments, the compound of the invention is not 5-[methyl(phenyl)sulfamoyl]-N-(5-methyl-1,3-thiazol-2-yl)-2-pyrrolidin-1-ylbenzamide, or a salt, solvate or N-oxide thereof. In yet other embodiments, the compound of the invention is not 5-(benzylsulfamoyl)-N-(5-methyl-1,3-thiazol-2-yl)-2-pyrrolidin-1-ylbenzamide, or a salt, solvate or N-oxide thereof. In yet other embodiments, the compound of the invention is not 5-(dimethylsulfamoyl)-N-(5-methyl-1,3-thiazol-2-yl)-2-piperidin-1-ylbenzamide, or a salt, solvate or N-oxide thereof. In yet other embodiments, the compound of the invention is not 2-(azetidin-1-yl)-5-(dimethylsulfamoyl)-N-(5-methyl-1,3-thiazol-2-yl)benzamide, or a salt, solvate or N-oxide thereof. In yet other embodiments, the compound of the invention is not 5-(dimethylsulfamoyl)-N-(5-methyl-1,3-thiazol-2-yl)-2-piperazin-1-ylbenzamide, or a salt, solvate or N-oxide thereof. In yet other embodiments, the compound of the invention is not 2-(dimethylamino)-5-(dimethylsulfamoyl)-N-(5-methyl-1,3-thiazol-2-yl)benzamide, or a salt, solvate or N-oxide thereof. In yet other embodiments, the compound of the invention is not 2-(diethylamino)-5-(dimethylsulfamoyl)-N-(5-methyl-1,3-thiazol-2-yl)benzamide, or a salt, solvate or N-oxide thereof. In yet other embodiments, the compound of the invention is not 2-cyclopentyl-5-(dimethylsulfamoyl)-N-(5-methyl-1,3-thiazol-2-yl)benzamide, or a salt, solvate or N-oxide thereof. In yet other embodiments, the compound of the invention is not 3-(dimethylsulfamoyl)-N-(5-methyl-1,3-thiazol-2-yl)benzamide, or a salt, solvate or N-oxide thereof. In yet other embodiments, the compound of the invention is not 4-methyl-N-(5-(morpholinosulfonyl)-2-(pyrrolidin-1-yl)phenyl)benzamide, or a salt, solvate or N-oxide thereof. In yet other embodiments, the compound of the invention is not 3-methyl-N-(5-(morpholinosulfonyl)-2-(pyrrolidin-1-yl)phenyl)benzamide, or a salt, solvate or N-oxide thereof. In yet other embodiments, the compound of the invention is not 5-(N,N-dimethylsulfamoyl)-N-(3-(N,N-dimethylsulfamoyl)-4-methylphenyl)-2-(pyrrolidin-1-yl)benzamide, or a salt, solvate or N-oxide thereof. In yet other embodiments, the compound of the invention is not 5-(N,N-dimethylsulfamoyl)-N-(3-fluoro-4-methylphenyl)-2-(pyrrolidin-1-yl)benzamide, or a salt, solvate or N-oxide thereof.

In certain embodiments, the compound is selected from the group consisting of 5-(N,N-Dimethylsulfamoyl)-N-(5-methyl-1,3-thiazol-2-yl)-2-(pyrrolidin-1-yl)benzamide, 5-(dimethylsulfamoyl)-N-(4-methyl-1,3-thiazol-2-yl)-2-pyrrolidin-1-ylbenzamide, 5-(dimethylsulfamoyl)-2-pyrrolidin-1-yl-N-(1,3-thiazol-2-yl)benzamide, 5-(dimethylsulfamoyl)-N-(5-methyl-1,3,4-thiadiazol-2-yl)-2-pyrrolidin-1-ylbenzamide, 5-(dimethylsulfamoyl)-N-(5-methyl-1H-1,2,4-triazol-3-yl)-2-pyrrolidin-1-ylbenzamide. N-(1,3-benzothiazol-2-yl)-5-(dimethylsulfamoyl)-2-pyrrolidin-1-ylbenzamide, 5-(dimethylsulfamoyl)-N-(4-methoxy-1,3-benzothiazol-2-yl)-2-pyrrolidin-1-ylbenzamide, 5-(dimethylsulfamoyl)-N-(5-methoxy-1,3-benzothiazol-2-yl)-2-pyrrolidin-1-ylbenzamide, 5-(dimethylsulfamoyl)-N-(6-methoxy-1,3-benzothiazol-2-yl)-2-pyrrolidin-1-ylbenzamide, 5-(dimethylsulfamoyl)-N-pyridin-3-yl-2-pyrrolidin-1-ylbenzamide, 5-(dimethylsulfamoyl)-N-pyridin-4-yl-2-pyrrolidin-1-ylbenzamide, 5-(dimethylsulfamoyl)-N-phenyl-2-pyrrolidin-1-ylbenzamide, 5-(dimethylsulfamoyl)-N-(2-methylphenyl)-2-pyrrolidin-1-ylbenzamide, 5-(dimethylsulfamoyl)-N-(4-methylphenyl)-2-pyrrolidin-1-ylbenzamide, 5-(dimethylsulfamoyl)-N-(2-methoxyphenyl)-2-pyrrolidin-1-ylbenzamide, 5-(dimethylsulfamoyl)-N-(4-methoxyphenyl)-2-pyrrolidin-1-ylbenzamide, 5-(dimethylsulfamoyl)-N-(2-fluorophenyl)-2-pyrrolidin-1-ylbenzamide, 5-(dimethylsulfamoyl)-N-(3-fluorophenyl)-2-pyrrolidin-1-ylbenzamide, 5-(dimethylsulfamoyl)-N-(2-chlorophenyl)-2-pyrrolidin-1-ylbenzamide, 5-(dimethylsulfamoyl)-N-(4-bromophenyl)-2-pyrrolidin-1-ylbenzamide, N,N-dimethyl-3-(morpholine-4-carbonyl)-4-pyrrolidin-1-ylbenzenesulfonamide, N-cyclohexyl-5-(dimethylsulfamoyl)-2-pyrrolidin-1-ylbenzamide, 5-(dimethylsulfamoyl)-N,N-dimethyl-2-pyrrolidin-1-ylbenzamide, 5-(diisobutylsulfamoyl)-N-(5-methyl-1,3-thiazol-2-yl)-2-pyrrolidin-1-ylbenzamide, 5-(diethylsulfamoyl)-N-(5-methyl-1,3-thiazol-2-yl)-2-pyrrolidin-1-ylbenzamide, N-(5-methyl-1,3-thiazol-2-yl)-2-pyrrolidin-1-yl-5-pyrrolidin-1-ylsulfonyl benzamide, N-(5-methyl-1,3-thiazol-2-yl)-5-piperidin-1-ylsulfonyl-2-pyrrolidin-1-ylbenzamide, N-(5-methyl-1,3-thiazol-2-yl)-5-morpholin-4-ylsulfonyl-2-pyrrolidin-1-ylbenzamide, N-(5-methyl-1,3-thiazol-2-yl)-5-piperazin-1-ylsulfonyl-2-pyrrolidin-1-ylbenzamide, 5-[methyl(phenyl)sulfamoyl]-N-(5-methyl-1,3-thiazol-2-yl)-2-pyrrolidin-1-ylbenzamide, 5-(benzylsulfamoyl)-N-(5-methyl-1,3-thiazol-2-yl)-2-pyrrolidin-1-ylbenzamide, 5-(dimethylsulfamoyl)-N-(5-methyl-1,3-thiazol-2-yl)-2-piperidin-1-ylbenzamide, 2-(azetidin-1-yl)-5-(dimethylsulfamoyl)-N-(5-methyl-1,3-thiazol-2-yl)benzamide, 5-(dimethylsulfamoyl)-N-(5-methyl-1,3-thiazol-2-yl)-2-piperazin-1-ylbenzamide, 2-(dimethylamino) 5-(dimethylsulfamoyl)-N-(5-methyl-1,3-thiazol-2-yl)benzamide, 2-(diethylamino)-5-(dimethylsulfamoyl)-N-(5-methyl-1,3-thiazol-2-yl) benzamide, 2-cyclopentyl-5-(dimethylsulfamoyl)-N-(5-methyl-1,3-thiazol-2-yl)benzamide, 3-(dimethylsulfamoyl)-N-(5-methyl-1,3-thiazol-2-yl)benzamide, 4-methyl-N-(5-(morpholinosulfonyl)-2-(pyrrolidin-1-yl)phenyl) benzamide, 3-methyl-N-(5-(morpholinosulfonyl)-2-(pyrrolidin-1-yl)phenylbenzamide, 5-(N,N-dimethylsulfamoyl)-N-(3-(N,N-dimethylsulfamoyl)-4-methylphenyl)-2-(pyrrolidin-1-yl)benzamide, and 5-(N,N-dimethylsulfamoyl)-N-(3-fluoro-4-methylphenyl)-2-(pyrrolidin-1-yl)benzamide.

In certain embodiments, the compound is not selected from the group consisting of 5-(N,N-Dimethylsulfamoyl)-N-(5-methyl-1,3-thiazol-2-yl)-2-(pyrrolidin-1-yl)benzamide, 5-(dimethylsulfamoyl)-N-(4-methyl-1,3-thiazol-2-yl)-2-pyrrolidin-1-ylbenzamide, 5-(dimethylsulfamoyl)-2-pyrrolidin-1-yl-N-(1,3-thiazol-2-yl)benzamide, 5-(dimethylsulfamoyl)-N-(5-methyl-1,3,4-thiadiazol-2-yl)-2-pyrrolidin-1-ylbenzamide, 5-(dimethylsulfamoyl)-N-(5-methyl-1H-1,2,4-triazol-3-yl)-2-pyrrolidin-1-ylbenzamide, N-(1,3-benzothiazol-2-yl)-5-(dimethylsulfamoyl)-2-pyrrolidin-1-ylbenzamide, 5-(dimethylsulfamoyl)-N-(4-methoxy-1,3-benzothiazol-2-yl)-2-pyrrolidin-1-ylbenzamide, 5-(dimethylsulfamoyl)-N-(5-methoxy-1,3-benzothiazol-2-yl)-2-pyrrolidin-1-ylbenzamide, 5-(dimethylsulfamoyl)-N-(6-methoxy-1,3-benzothiazol-2-yl)-2-pyrrolidin-1-ylbenzamide, 5-(dimethylsulfamoyl)-N-pyridin-3-yl-2-pyrrolidin-1-ylbenzamide, 5-(dimethylsulfamoyl)-N-pyridin-4-yl-2-pyrrolidin-1-ylbenzamide, 5-(dimethylsulfamoyl)-N-phenyl-2-pyrrolidin-1-ylbenzamide, 5-(dimethylsulfamoyl)-N-(2-methylphenyl)-2-pyrrolidin-1-ylbenzamide, 5-(dimethylsulfamoyl)-N-(4-methylphenyl)-2-pyrrolidin-1-ylbenzamide, (dimethylsulfamoyl)-N-(2-methoxyphenyl)-2-pyrrolidin-1-ylbenzamide, 5-(dimethylsulfamoyl)-N-(4-methoxyphenyl)-2-pyrrolidin-1-ylbenzamide, 5-(dimethylsulfamoyl)-N-(2-fluorophenyl)-2-pyrrolidin-1-ylbenzamide, 5-(dimethylsulfamoyl)-N-(3-fluorophenyl)-2-pyrrolidin-1-ylbenzamide, 5-(dimethylsulfamoyl)-N-(2-chlorophenyl)-2-pyrrolidin-1-ylbenzamide, 5-(dimethylsulfamoyl)-N-(4-bromophenyl)-2-pyrrolidin-1-ylbenzamide, N,N-dimethyl-3-(morpholine-4-carbonyl)-4-pyrrolidin-1-ylbenzenesulfonamide, N-cyclohexyl-5-(dimethylsulfamoyl)-2-pyrrolidin-1-ylbenzamide, 5-(dimethylsulfamoyl)-N, N-dimethyl-2-pyrrolidin-1-ylbenzamide, 5-(diisobutylsulfamoyl)-N-(5-methyl-1,3-thiazol-2-yl)-2-pyrrolidin-1-ylbenzamide, 5-(diethylsulfamoyl)-N-(5-methyl-1,3-thiazol-2-yl)-2-pyrrolidin-1-ylbenzamide, N-(5-methyl-1,3-thiazol-2-yl)-2-pyrrolidin-1-yl-5-pyrrolidin-1-ylsulfonyl benzamide, N-(5-methyl-1,3-thiazol-2-yl)-5-piperidin-1-ylsulfonyl-2-pyrrolidin-1-ylbenzamide, N-(5-methyl-1,3-thiazol-2-yl)-5-morpholin-4-ylsulfonyl-2-pyrrolidin-1-ylbenzamide, N-(5-methyl-1,3-thiazol-2-yl)-5-piperazin-1-ylsulfonyl-2-pyrrolidin-1-ylbenzamide, 5-[methyl(phenyl)sulfamoyl]-N-(5-methyl-1,3-thiazol-2-yl)-2-pyrrolidin-1-ylbenzamide, 5-(benzyl sulfamoyl)-N-(5-methyl-1,3-thiazol-2-yl)-2-pyrrolidin-1-ylbenzamide, 5-(dimethylsulfamoyl)-N-(5-methyl-1,3-thiazol-2-yl)-2-piperidin-1-ylbenzamide, 2-(azetidin-1-yl)-5-(dimethylsulfamoyl)-N-(5-methyl-1,3-thiazol-2-yl) benzamide, 5-(dimethylsulfamoyl)-N-(5-methyl-1,3-thiazol-2-yl)-2-piperazin-1-ylbenzamide, 2-(dimethylamino)-5-(dimethylsulfamoyl)-N-(5-methyl-1,3-thiazol-2-yl)benzamide, 2-(diethylamino)-5-(dimethylsulfamoyl)-N-(5-methyl-1,3-thiazol-2-yl)benzamide, 2-cyclopentyl-5-(dimethylsulfamoyl)-N-(5-methyl-1,3-thiazol-2-yl)benzamide, 3-(dimethylsulfamoyl)-N-(5-methyl-1,3-thiazol-2-yl)benzamide, 4-methyl-N-(5-(morpholinosulfonyl)-2-(pyrrolidin-1-yl)phenyl)benzamide, 3-methyl-N-(5-(morpholinosulfonyl)-2-(pyrrolidin-1-yl)phenyl)benzamide, 5-(N,N-dimethylsulfamoyl)-N-(3-(N,N-dimethylsulfamoyl)-4-methylphenyl)-2-(pyrrolidin-1-yl)benzamide, and 5-(N,N-dimethyl sulfamoyl)-N-(3-fluoro-4-methylphenyl)-2-(pyrrolidin-1-yl)benzamide.

In certain embodiments, the compound is not selected from the group consisting of 5-(N,N-Dimethylsulfamoyl)-N-(5-methyl-1,3-thiazol-2-yl)-2-(pyrrolidin-1-yl)benzamide, 5-(dimethylsulfamoyl)-N-(5-methyl-1,3,4-thiadiazol-2-yl)-2-pyrrolidin-1-ylbenzamide, N-(1,3-benzothiazol-2-yl)-5-(dimethylsulfamoyl)-2-pyrrolidin-1-ylbenzamide, 5-(dimethylsulfamoyl)-N-pyridin-3-yl-2-pyrrolidin-1-ylbenzamide, 5-(dimethylsulfamoyl)-N-pyridin-4-yl-2-pyrrolidin-1-ylbenzamide, 5-(dimethylsulfamoyl)-N-phenyl-2-pyrrolidin-1-ylbenzamide, 5-(dimethylsulfamoyl)-N-(2-methylphenyl)-2-pyrrolidin-1-ylbenzamide, 5-(dimethylsulfamoyl)-N-(4-methylphenyl)-2-pyrrolidin-1-ylbenzamide, 5-(dimethylsulfamoyl)-N-(4-methoxyphenyl)-2-pyrrolidin-1-ylbenzamide, 5-(dimethylsulfamoyl)-N-(2-fluorophenyl)-2-pyrrolidin-1-ylbenzamide, 5-(dimethylsulfamoyl)-N-(3-fluorophenyl)-2-pyrrolidin-1-ylbenzamide, 5-(dimethylsulfamoyl)-N-(2-chlorophenyl)-2-pyrrolidin-1-ylbenzamide, 5-(dimethylsulfamoyl)-N-(4-bromophenyl)-2-pyrrolidin-1-ylbenzamide, N, N-dimethyl-3-(morpholine-4-carbonyl)-4-pyrrolidin-1-N-cyclohexyl-5-(dimethylsulfamoyl)-2-pyrrolidin-1-ylbenzamide, 5-(diethylsulfamoyl)-N-(5-methyl-1,3-thiazol-2-yl)-2-pyrrolidin-1-ylbenzamide, N-(5-methyl-1,3-thiazol-2-yl)-5-piperidin-1-ylsulfonyl-2-pyrrolidin-1-ylbenzamide, N-(5-methyl-1,3-thiazol-2-yl)-5-morpholin-4-ylsulfonyl-2-pyrrolidin-1-ylbenzamide, or 5-(dimethylsulfamoyl)-N-(5-methyl-1,3-thiazol-2-yl)-2-piperidin-1-ylbenzamide.

In certain embodiments, the compound of the invention is selected from the group consisting of: 5-(dimethylsulfamoyl)-N-(4-methyl-1,3-thiazol-2-yl)-2-pyrrolidin-1-ylbenzamide, 5-(dimethylsulfamoyl)-N-(5-methyl-1H-1,2,4-triazol-3-yl)-2-pyrrolidin-1-ylbenzamide, 5-(dimethylsulfamoyl)-N-(4-methoxy-1,3-benzothiazol-2-yl)-2-pyrrolidin-1-ylbenzamide, 5-(dimethylsulfamoyl)-N-(5-methoxy-1,3-benzothiazol-2-yl)-2-pyrrolidin-1-ylbenzamide, 5-(dimethylsulfamoyl)-N-(6-methoxy-1,3-benzothiazol-2-yl)-2-pyrrolidin-1-ylbenzamide, 5-(dimethylsulfamoyl)-N-(2-methoxyphenyl)-2-pyrrolidin-1-ylbenzamide, 5-(dimethylsulfamoyl)-N, N-dimethyl-2-pyrrolidin-1-ylbenzamide, 5-(diisobutylsulfamoyl)-N-(5-methyl-1,3-thiazol-2-yl)-2-pyrrolidin-1-ylbenzamide, N-(5-methyl-1,3-thiazol-2-yl)-2-pyrrolidin-1-yl-5-pyrrolidin-1-ylsulfonyl benzamide, N-(5-methyl-1,3-thiazol-2-yl)-5-piperazin-1-ylsulfonyl-2-pyrrolidin-1-ylbenzamide, 5-[methyl(phenyl)sulfamoyl]-N-(5-methyl-1,3-thiazol-2-yl)-2-pyrrolidin-1-ylbenzamide, 5-(benzylsulfamoyl)-N-(5-methyl-1,3-thiazol-2-yl)-2-pyrrolidin-1-ylbenzamide, 2-(azetidin-1-yl)-5-(dimethylsulfamoyl)-N-(5-methyl-1,3-thiazol-2-yl)benzamide, 5-(dimethylsulfamoyl)-N-(5-methyl-1,3-thiazol-2-yl)-2-piperazin-1-ylbenzamide, 2-(dimethylamino)-5-(dimethylsulfamoyl)-N-(5-methyl-1,3-thiazol-2-yl)benzamide, 2-(diethylamino)-5-(dimethylsulfamoyl)-N-(5-methyl-1,3-thiazol-2-yl) benzamide, 2-cyclopentyl-5-(dimethylsulfamoyl)-N-(5-methyl-1,3-thiazol-2-yl)benzamide, and 3-(dimethylsulfamoyl)-N-(5-methyl-1,3-thiazol-2-yl)benzamide.

In certain embodiments, the compound of the invention is a compound of formula (II):

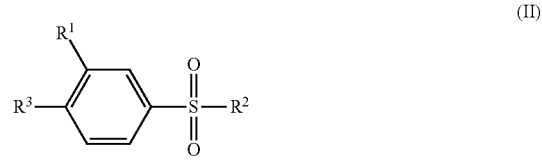

(II)

In certain embodiments, in (I) or (II), R¹ is selected from the group consisting of

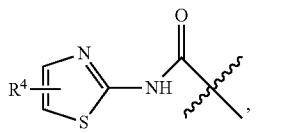

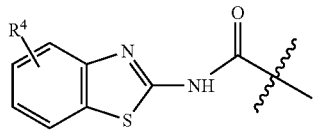, and

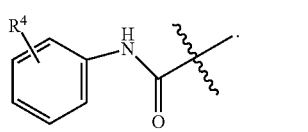.

In other embodiments, in (I) or (II), R² is selected from the group consisting of:

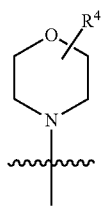 and 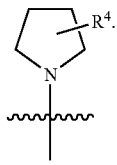.

In yet other embodiments, in (I) or (II). R³ is selected from the group consisting of

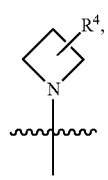, 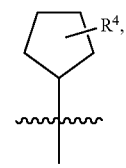, —N(R⁴)₂, and 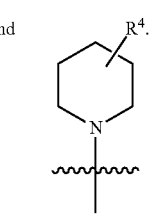.

In yet other embodiments, in (I) or (II), R¹ is selected from the group consisting of

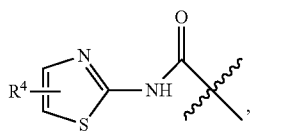,

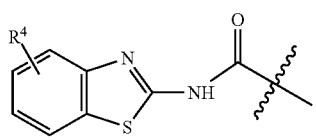, and

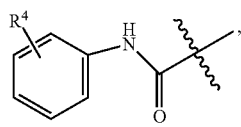, and R² is selected from the group consisting of

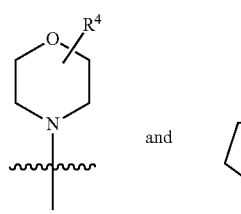 and 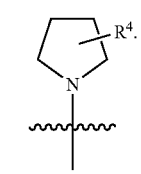.

In yet other embodiments, in (I) or (II), R¹ is selected from the group consisting of

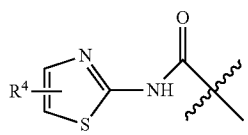,

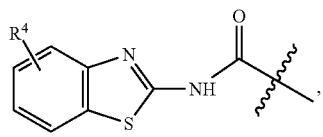, and

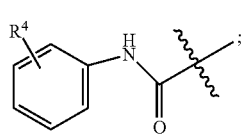;

and R³ is selected from the group consisting of

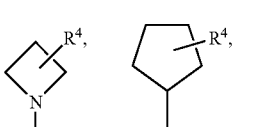, 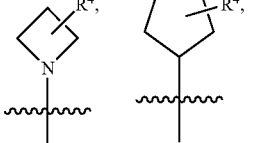, -N(R⁴)₂, and 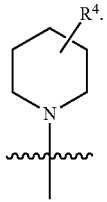.

In yet other embodiments, in (I) or (II), R² is selected from the group consisting of

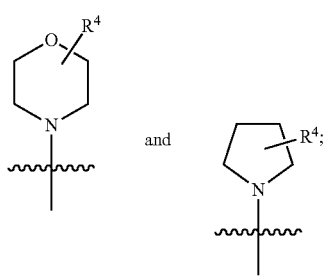 and 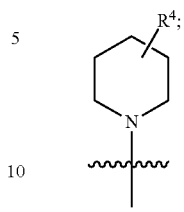
and $R^3$ is selected from the group consisting of
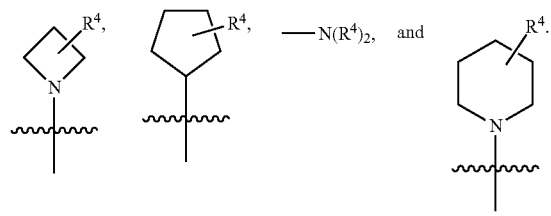
In yet other embodiments, in (I) or (II), $R^1$ is
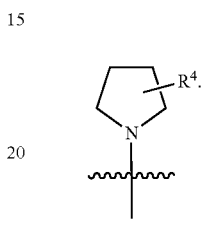
$R^2$ is
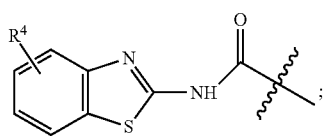
and $R^3$ is
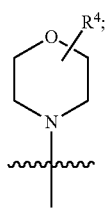
In yet other embodiments, in (I) or (II), $R^1$ is
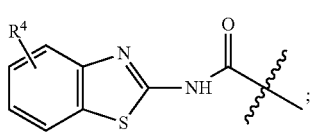
$R^2$ is
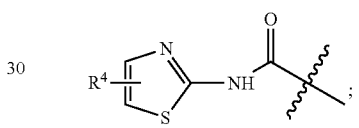
and $R^3$ is
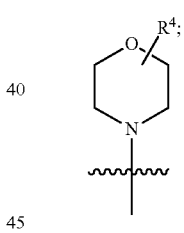
In yet other embodiments, in (I) or (II). $R^1$ is
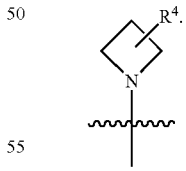
$R^2$ is
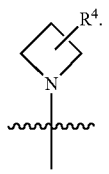
and $R^3$ is
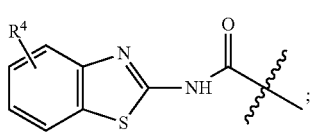
In yet other embodiments, in (I) or (II), $R^1$ is
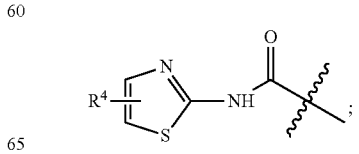

R² is

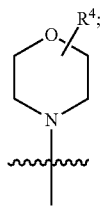

and R³ is

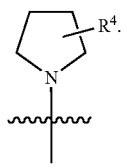

In yet other embodiments, in (I) or (II), R¹ is

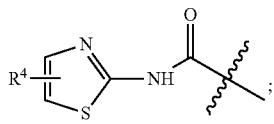

R² is —N(R⁴)₂; and R³ is

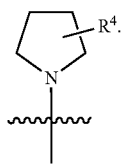

In another aspect, the compound of the invention, or a salt, solvate or N-oxide thereof, is selected from the group consisting of:
3-benzyl-1-(3-(dimethylamino)propyl)-1-((2-oxo-1,2-dihydroquinolin-3-yl)methyl)urea

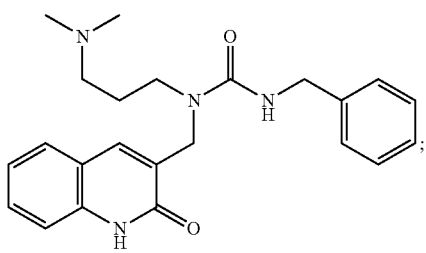 [SMILES: CN(C)CCCN(Cc1cc2ccccc2[nH]c1=O)C(=O)NCc1ccccc1]

1-(3-(dimethylamino)propyl)-1-((2-oxo-1,2-dihydroquinolin-3-yl)methyl)-3-phenylurea

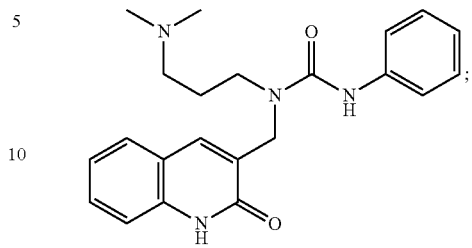

3-benzyl-1-((7,8-dimethyl-2-oxo-1,2-dihydroquinolin-3-yl)methyl)-1-(3-(dimethylamino)propyl) urea

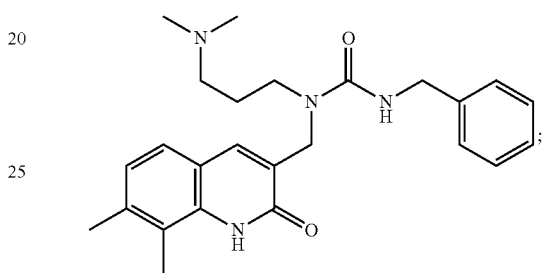

1-((7,8-dimethyl-2-oxo-1,2-dihydroquinolin-3-yl)methyl)-1-(3-(dimethylamino)propyl)-3-phenylurea

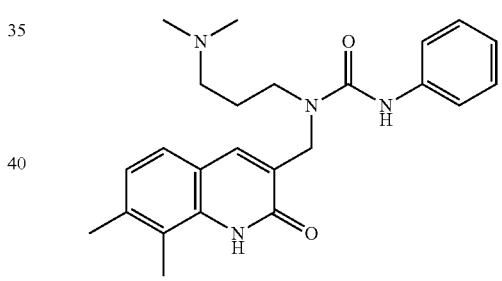

In certain embodiments, the compound of the invention, or a salt, solvate or N-oxide thereof, is selected from the group consisting of: 3-benzyl-1-(3-(dimethylamino) propyl)-1-((2-oxo-1,2-dihydroquinolin-3-yl)methyl)urea and 1-(3-(dimethylamino)propyl)-1-((2-oxo-1,2-dihydroquinolin-3-yl)methyl)-3-phenylurea. In other embodiments, the compound of the invention, or a salt, solvate or N-oxide thereof, is not selected from the group consisting of: 3-benzyl-1-((7,8-dimethyl-2-oxo-1,2-dihydroquinolin-3-yl) methyl)-1-(3-(dimethylamino)propyl) urea and 1-((7,8-dimethyl-2-oxo-1,2-dihydroquinolin-3-yl)methyl)-1-(3-(dimethylamino) propyl)-3-phenylurea.

Preparation of Compounds of the Invention

Compounds of formulas (I)-(II) may be prepared by the general schemes described herein, using the synthetic method known by those skilled in the art. The following examples illustrate non-limiting embodiments of the invention.

The compounds of the invention may possess one or more stereocenters, and each stereocenter may exist independently in either the (R) or (S) configuration. In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention may exist as tautomers. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

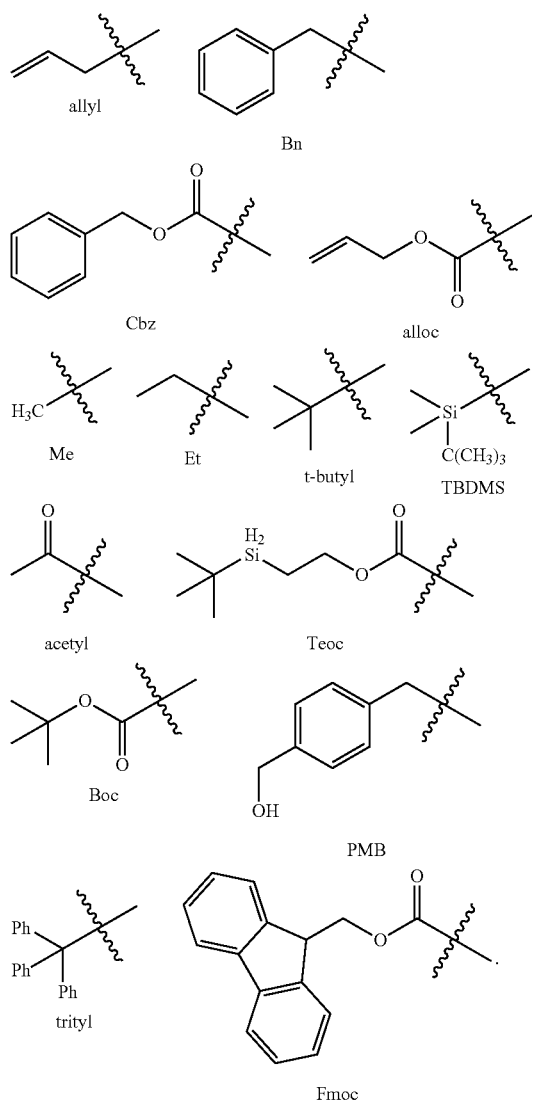

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Compositions

The invention includes a pharmaceutical composition comprising at least one compound of the invention and at least one pharmaceutically acceptable carrier. In certain embodiments, the composition is formulated for an administration route such as oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Methods

The invention includes a method of treating or preventing a disease associated with N-linked glycosylation in a subject in need thereof. In certain embodiments, the disease comprises a cancer.

As demonstrated herein, the compounds of the present invention inhibit N-linked glycosylation. In certain embodiments, such inhibition comprises OST inhibition. In other embodiments, the compounds of the present invention inhibit growth and/or kill cancer cells that are dependent on RTKs for proliferation.

Examples of cancers that can be treated or prevented by the present invention include but are not limited to: squamous cell cancer, lung cancer including small cell lung cancer, non-small cell lung cancer, vulval cancer, thyroid cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, hepatic carcinoma, anal carcinoma, penile carcinoma, and head and neck cancer. In certain embodiments, the cancer comprises small cell lung cancer, non-small cell lung cancer, head and neck squamous cell carcinoma, breast cancer, gastric cancer, cervical cancer, colon cancer, and glioma.

The methods of the invention comprise administering to the subject a therapeutically effective amount of at least one compound of the invention, which is optionally formulated in a pharmaceutical composition. In certain embodiments, the method further comprises administering to the subject an additional therapeutic agent that treats or prevents cancer.

In certain embodiments, administering the compound of the invention to the subject allows for administering a lower dose of the additional therapeutic agent as compared to the dose of the additional therapeutic agent alone that is required to achieve similar results in treating or preventing a cancer in the subject. For example, in certain embodiments, the compound of the invention enhances the anti-cancer activity of the additional therapeutic compound, thereby allowing for a lower dose of the additional therapeutic compound to provide the same effect.

In certain embodiments, the compound of the invention and the therapeutic agent are co-administered to the subject. In other embodiments, the compound of the invention and the therapeutic agent are coformulated and co-administered to the subject.

In certain embodiments, the subject is a mammal. In other embodiments, the mammal is a human.

Combination Therapies

The compounds useful within the methods of the invention may be used in combination with one or more additional therapeutic agents useful for treating a cancer. These additional therapeutic agents may comprise compounds that are commercially available or synthetically accessible to those skilled in the art. These additional therapeutic agents are known to treat, prevent, or reduce the symptoms, of a cancer.

In non-limiting examples, the compounds useful within the invention may be used in combination with one or more of the following therapeutic agents: Erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), pemetrexed (ALIMTA®, Eli Lilly), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl) phenoxy]-N,N-dimethylethanamine, NOLVADEXV®, ISTUBAL®, VALODEX®), and doxorubicin (ADRIAMYCIN®), Akti-1/2, HPPD, rapamycin, oxaliplatin (ELOXATIN®, Sanofi), bortezomib (VELCADE®, Millennium Pharm.), sutent (SUNITINIB®, SU11248, Pfizer), letrozole (FEMARA, Novartis), imatinib mesylate (GLEEVEC®, Novartis), XL-518 (Mek inhibitor, Exelixis, WO 2007/044515), ARRY-886 (Mek inhibitor, AZD6244, Array Bio-Pharma, Astra Zeneca). SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafamib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Ill.), vandetanib (rINN, ZD6474. ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®), ALK TKI inhibitors, antibodies such as avastin and cetuximab that target VEGFR and EGFR respectively, other RTK TKIs for PDGFR or RET, immunotherapies such as ipiliumimab and nivolumab, and radiation therapy.

In certain embodiments, the compounds of the present invention are used in combination with radiation therapy. In other embodiments, the combination of administration of the compounds of the present invention and application of radiation therapy is more effective in treating or preventing cancer than application of radiation therapy by itself. In yet other embodiments, the combination of administration of the compounds of the present invention and application of radiation therapy allows for use of lower amount of radiation therapy in treating the subject.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek. 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a cancer. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a cancer in the patient. An effective amount of the therapeutic compound necessary to achieve a therapeutic effect may vary according to factors such as the state of the disease or disorder in the patient; the age, sex, and weight of the patient; and the ability of the therapeutic compound to treat a cancer in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a cancer in a patient.

In certain embodiments, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 350 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a cancer in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropyl methylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRYT™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g, almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of G-protein receptor-related diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a cancer in the patient being treated. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Methods and Materials

Cell Lines and Culture Conditions:

The H3255, H1581, H4222, HEK293T, and HepG2 cell lines were purchased from the ATCC (Rockville, Md.). The PC9 cell line was a gift from Katie Politi (Yale University. New Haven Conn.), the A549 and H1975 cell lines were gifts from Abhi Patel (Yale University, New Haven Conn.), and the HCC827 line was a gift from Jeff Engelman (MGH, Boston Mass.). Cells were maintained in RPMI media supplemented with 10% FBS and pen/strep at 37° C. in a humidified incubator with 5% $CO_2$.

High Throughput Screening:

The HTS approach using the bioluminescent N-linked glycosylation reporter (CCR 2011) in D54-ERLucT and D54-LucT cells has been previously described (Bennett, et al., Transl Oncol 2013, 6, 382-391). Briefly, the primary cell-based screen detects site occupancy of NLG sequons using a modified luciferase protein translated into the ER. Inhibition of NLG in D45-ERLucT increases luciferase activity whereas it does not increase activity in the D54-LucT cell line. The methodology for the primary (D54-ERlucT), secondary (D54-LucT), and tertiary (luciferase inhibition) screens as well and toxicity assays with Celltitre-Glo are deposited in Pubchem (AID 588693).

LLO, Protein, and RNA Detection:

Fluorophore assisted carbohydrate electrophoresis (FACE) was performed as previously described (Gao, et al., Glycobiology 2002, 12, 353-360; Gao, et al., J Biol Chem 2005, 280, 17901-17909). Control (Ac-Gln-Tyr-Thr-$CONH_2$) and acceptor (Ac-Asn-Tyr-Thr-$CONH_2$) peptides were used for permeabilized cell experiments. Metabolic labeling of Hela cells, transfection of prosaposin (pSAP) and steroid hormone binding globulin (SHBG) vectors, and knockdown of SIT3A and STT3B to monitor N-linked glycosylation knockdown were performed as described (Shrimal, et al., J Cell Biol 2013, 201, 81-95). Western blot analysis was performed as previously described (Bennett, et al., Transl Oncol 2013, 6, 382-391). The following primary antibodies were used: rabbit anti-EGFR (sc-03; Santa Cruz Biotechnology; 1:1000), rabbit anti-phospho (Tyr1173) EGF Receptor (Cell Signaling; 1:1000), rabbit anti-p21 Waf1/Cip1 (12D1; Cell Signaling; 1:1000), rabbit anti-Cyclin D1 (Cell Signaling; 1:1000), mouse anti-β-Actin (8H10D10; Cell Signaling; 1:1000). For phospho-protein array analysis, PC9 and A549 cells were cultured in 6-well plates in serum-containing medium and treated with or without 10 µM NGI-1 for 24 hours. The human Phospho-protein array kit (R&D Systems) was used to simultaneously detect the relative site-specific phosphorylation of 43 kinases and 2 related total proteins according to the manufacturer's protocol.

Biotinylation and recovery of cell surface proteins were performed on intact H3255 cell monolayers using EZ-link Sulfo-NHS—SS Biotin (Pierce) and isolated using streptavidin-agarose beads (Sigma-Aldrich). Control or cells treated with 10 um NGI-1 for 24 h were placed on ice and washed three times with PBS. The cells were incubated with EZ-link Sulfo-NHS—SS-Biotin at a final concentration of 0.5 mg/ml in PBS for 60 min at 4° C., followed by 100 mM glycine/PBS wash, and two washes with PBS. Biotinylated cells were scraped into lysis buffer (25 mM Tris-HCl pH 7.4, 10 mM EDTA, 15% glycerol, 0.1% Triton X-100, protease inhibitor tablet (Roche Diagnostics; Indianapolis, Ind., USA) and phosphatase inhibitor cocktails 2 and 3 (Sigma-Aldrich)) and agitated on a shaker for 60 min at 4° C. The cell lysate was centrifuged for 10 min at 14,000×g, and the resulting supernatant was incubated with streptavidin-agarose beads, suspended in lysis buffer, and mixed at 4° C. overnight. The beads were recovered by centrifugation (5,000×g for 15 s) and aliquots of supernatants were taken to represent the unbound, intracellular pool of proteins. Biotinylated proteins were eluted from the beads by heating to 100° C. for 5 min in SDS-PAGE sample buffer before loading onto a 7.5% SDS-PAGE gel for WB analysis against EGFR.

For PNGase digestion 10 µg lysate were digested with peptide N-glycosidase F (PNGase-F, New England Biolabs, Beverly, Mass.). Specifically, samples were incubated in denaturing buffer (0.5% SDS and 1% β-mercaptoethanol) for 10 min at 100° C. and brought to 50 mM sodium phosphate (pH 7.5) with 1% Nonidet P-40. Then, 1 µl (500 units) of PNGase-F was added and incubated 1 h at 37° C. After glycosidase digestion, SDS-PAGE sample buffer was added and incubated at 100° C. for 5 min. Equal amounts of non-digested and digested PNGase-F proteins were subjected to SDS-PAGE and WB analysis for EGFR.

For Quantitative RT-PCR A549 and PC-9 cells were seeded in 6 $cm^2$ dishes, after NGI-1 treatment total mRNA purification was performed using the RNeasy Mini Kit (QIAGEN) and reverse transcribed into cDNA using ISCRIPT® cDNA Synthesis Kit (BIO-RAD) according to the manufacturer's protocol. The newly synthesized cDNA was amplified using IQ® SYBR® Green QPCR Master Mix Supermix (Agilent Technologies) and expression levels of human Cyclin D1 and human GAPDH mRNA were determined using these specific primers: Cyclin D1 forward: (SEQ ID NO: 1) 5'-ACCTGAGGAGCCCCAACAA-3'; reverse: (SEQ ID NO:2) 5'-TCTGCTCCTGGCAGGCC-3'. GAPDH forward: (SEQ ID NO:3) 5'-GCTCTCTGCTCCTCCTGTC-3'; reverse: (SEQ ID NO:4) 5'-ACGACCAAATCCGTTGACTC-3'. The incubation conditions were as follows: 1 cycle at 95° C. for 10 min, followed by 40 cycles of 30 sec at 95° C., annealing for 15 sec at 55° C., and extension for 30 sec at 72° C. PCRs for each sample were done in triplicate for all the genes.

Microscopy:

For immunofluorescence. H3255 cell lines were grown on glass coverslips to 60% confluence. Cell cultures were washed with PBS and fixed with 4% (w/v) formaldehyde in PBS for 30 min at 37° C. After washing with PBS, cells were permeabilized with 0.1% v/v Triton X-100 in PBS for 10 min, rinsed three times in PBS and treated with 5% w/v bovine serum albumin for 1 h. Cells were then incubated overnight at 4° C. with either Rabbit anti-EGFR pAb (1:2.000) or mouse anti-CRT mAb (1:1000) primary antibodies and for 1 h at room temperature with the either Alexa Fluor 543-conjugated goat anti-rabbit IgG (1:1,000) or Alexa Fluor 488-conjugated goat anti-mouse IgG (1:1,000) secondary antibodies. All antibodies were diluted in PBS containing 5% w/v bovine serum albumin. Nuclei was stained using ToPro3 (Invitrogen). Confocal cellular images were captured with an inverted Zeiss LSM 510 Pascal laser confocal microscope (Carl Zeiss, Jenna. Germany), using a 63/1.4 Plan-Apochromat objective.

Glycomics:

Cells were surface biotinylated as described elsewhere herein, and the lysate was mixed with 2× sample loading buffer containing 50 mM of DTT and boiled for 5 min. The boiled samples were separated by SDS-PAGE (BioRad TGX MiniProtean) for 10 min at 200 V. Each lane of the gel was cut and denatured by incubating with 10 mM of DTT at 56° C. for an hour, alkylated by 55 mM of iodoacetamide for 45 minutes in the dark, and then digested with trypsin at 37° C. overnight. The resulting peptides were extracted, dried and deglycosylated by PNGasF (ProZyme) at 37° C. overnight in the presence of $H2^{18}O$ (Cambridge Isotope Laboratories, Inc.). The deglycosylated peptides were then dried and reconstituted in 0.1% formic acid. The peptides were separated on a 75 µm (I.D.)×15 cm C18 capillary column (packed in house, YMC GEL ODS-AQ 120AS-5, Waters) and 703 eluted into the nano-electrospray ion source of an Orbitrap Fusion™ Tribrid™ mass spectrometer (Thermo Fisher Scientific) with a 180-min linear gradient consisting of 0.5-100% solvent B over 150 min at a flow rate of 200 nL/min. The spray voltage was set to 2.2 kV and the temperature of the heated capillary was set to 280° C. Full MS scans were acquired from m/z 300 to 2000 at 120 k resolution, and MS2 scans following collision induced fragmentation were collected in the ion trap for the most intense ions in the Top-Speed mode within a 3-sec cycle using Fusion instrument software (v1.1, Thermo Fisher Scientific). The raw spectra were searched against the human protein database (UniProt, October 2014) using SEQUEST (Proteome Discoverer 1.4, Thermo Fisher Scientific) with full MS peptide tolerance of 20 ppm and MS2 peptide fragment tolerance of 0.5 Da, and filtered using ProteoIQ (v2.7, Premier Biosoft) to generate a false discovery rate of 1% at protein level and 5% at peptide level for any protein/peptide assignments.

Proliferation Assays:

Growth rates were determined by CellTiter 96 NonRadioactive Cell Proliferation Assay (Promega; Madison, Wis. USA) according to the manufacturer's directions. Briefly, NSCLC cells ($2\times10^3$) untreated or treated with 101M NGI-1 or 1 µM Tn, were seeded in triplicates in 96-wells plates and grown in culture medium containing 10%. Cell numbers were estimated after 0, 3, and 5 days by adding MTT [(3-(4,5-Dimethylthiazol-2-yl)-2,5-diphenyltetrazolium bromide] reagent to the wells 4 hours before taking the spectrophotometric reading (absorbance at 570 nm).

Cell Cycle Distribution:

For the assessment of cell cycle distribution, $1\times10^6$ cells were collected, washed once with ice-cold PBS and fixed in ice-cold 70% ethanol overnight at −20° C. Thereafter, cells were washed twice with PBS and incubated for 30 min at room temperature in 200 µL of Guava Cell Cycle Reagent (Guava Technologies). Cytofluorometric acquisitions were performed on a LSRII cytometer (BD Biosciences). First-line analysis was performed with Flow Jo software, upon gating on the events characterized by normal forward and side scatter parameters and discrimination of doublets in a FSC-A vs. FSC-H bivariate plot. Approximately 30,000 cells were analyzed per experiment, and the mean value was obtained from 3 independent assays.

Assessment of Senescence:

Auto-fluorescence of PC9 and A549 cells untreated or treated with 10 µM NGI-1 for 24 hrs was characterized by flow cytometry after fixing the cells with 70% ethanol, staining with 4,6-diamino-2-phenyl indole (DAPI) for 30 min. Acquisition was done on a LRSII flow cytometer (BD Biosciences) equipped with green (488 nM) and UV (350 nM) lasers and measured using a detector for PE after gating with DAPI. Lipofuscin accumulation was detected by confocal laser scanning microscopy using an excitation laser of 405 nm with acquired signals from spectrums of yellow 575-620 nm. Morphology changes were explored by differential interference contrast (DIC). Fluorescence and DIC images were captured with a Leica SP5 confocal microscope.

Statistics:

Data points are reported as experimental averages and error bars represent standard deviation or standard error as indicated. Statistical significance was determined using a two-sided Student's t test. A p value <0.05 was considered to be statistically significant.

Example 1: Synthesis of NGI-1

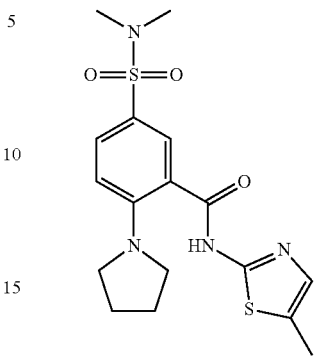

Methyl 5-(chlorosulfonyl)-2-hydroxybenzoate

To a round-bottom flask was added the chlorosulfonic acid (30 mL, 450 mmol). The flask was cooled to 0° C. and the methyl 2-hydroxybenzoate (6.4 mL, 50.0 mmol) was added dropwise over 30 min. The reaction was allowed to warm to rt and was then heated to 40° C. After 2 h the reaction was cooled to rt and poured into ice water (200 mL). The solid precipitate was filtered to produce methyl 5-(chlorosulfonyl)-2-hydroxybenzoate (11.2 g, 44.7 mmol, 90% yield) as a white solid. $^1$H NMR (400 MHz, CDCl$_3$) δ 11.55 (s, 1H), 8.57 (d, J=2.6 Hz, 1H), 8.09 (dd, J=9.0, 2.6 Hz, 1H), 7.18 (d, J=9.0 Hz, 1H), 4.04 (s, 3H).

Methyl 5-(N,N-dimethylsulfamoyl)-2-hydrozybenzoate

To a vial was added dimethylamine hydrochloride (1.46 g, 18.0 mmol) and DIPEA (4.2 mL, 23.9 mmol) in acetonitrile (4 mL) and the reaction stirred at rt for 30 min. Methyl 5-(chlorosulfonyl)-2-hydroxybenzoate (1.50 g, 6.0 mmol) was then added portionwise over 10 minutes and after addition the reaction stirred at rt for 2 h. At this time the reaction was concentrated and the residue was diluted with saturated NaHCO$_3$ (20 mL) and extracted with EtOAc (3×20 mL). The organic layers were combined and dried over MgSO$_4$, filtered and concentrated. The crude product was dissolved in 50% EtOAc:hexanes (20 mL) and filtered through a silica plug. The eluent was collected and concentrated to provide methyl 5-(N,N-dimethylsulfamoyl)-2-hydroxybenzoate (1.36 g, 5.25 mmol, 88% yield) as a white solid. $^1$H NMR (400 MHz, CDCl$_3$) δ 11.24 (s, 1H), 8.30 (d, J=2.3 Hz, 1H), 7.84 (dd, J=8.8, 2.4 Hz, 1H), 7.12 (d, J=8.8 Hz, 1H), 4.00 (s, 3H), 2.71 (s, 6H).

Methyl 5-(N,N-dimethylsulfamoyl)-2-(((trifluoromethyl)sulfonyl)oxy)benzoate

To a vial was added methyl 5-(N,N-dimethylsulfamoyl)-2-hydroxybenzoate (0.36 g, 1.40 mmol) and CH$_2$Cl$_2$ (4 mL) followed by pyridine (0.23 mL, 2.79 mmol). The reaction was then cooled to 0° C. and the 1.0 M solution of trifluoromethanesulfonic anhydride in CH$_2$Cl$_2$ (1.68 mL, 1.68 mmol) was added dropwise over 10 minutes. The reaction was then allowed to warm to rt and stirred for 3 h at which point it was washed with saturated NaHCO$_3$ (10 mL) and the CH$_2$Cl$_2$ was extracted. The remaining aqueous layer was extracted further with CH$_2$Cl$_2$ (2×10 mL). The organic layers were combined and dried over MgSO$_4$, filtered and concentrated to produce methyl 5-(N,N-dimethylsulfamoyl)-2-(((trifluoromethyl)sulfonyl)oxy)benzoate (0.50 g, 1.28 mmol, 92% yield) as a white solid. $^1$H NMR (400 MHz, CDCl$_3$) δ 8.47 (d, J=2.4 Hz, 1H), 8.03 (dd, J=8.6, 2.4 Hz, 1H), 7.49 (d, J=8.6 Hz, 1H), 4.01 (s, 3H), 2.80 (s, 6H).

Methyl 5-(N,N-dimethylsulfamoyl)-2-(pyrrolidin-1-yl)benzoate

To a vial was added methyl 5-(N,N-dimethylsulfamoyl)-2-(((trifluoromethyl) sulfonyl)oxy)benzoate (0.96 g, 2.46 mmol), pyrrolidine (0.61 mL, 7.38 mmol) and acetonitrile. The reaction was heated to 80° C. and stirred for 1 h, at which point the reaction was removed from heat and allowed to cool to rt. The reaction was then concentrated and the residue was re-dissolved in EtOAc (15 mL) and washed with saturated NaHCO$_3$ (15 mL), dried over MgSO$_4$, filtered and concentrated to produce methyl 5-(N,N-dimethylsulfamoyl)-2-(pyrrolidin-1-yl)benzoate (0.73 g, 2.34 mmol, 95% yield) as a light yellow solid. $^1$H NMR (400 MHz, CDCl$_3$) δ 7.97 (d, J=2.4 Hz, 1H), 7.64 (dd, J=9.0, 2.4 Hz, 1H), 6.80 (d, J=9.0 Hz, 1H), 3.90 (s, 3H), 3.34-3.25 (m, 4H), 2.68 (s, 6H), 2.03-1.97 (m, 4H).

5-(N,N-Dimethysulfamoyl)-2-(pyrrolidin-1-yl)benzoic acid

To a vial was added methyl 5-(N,N-dimethylsulfamoyl)-2-(pyrrolidin-1-yl)benzoate (0.73 g, 2.34 mmol), MeOH (4 mL) and 5.0 M NaOH in water (4.69 mL, 23.4 mmol) and the reaction stirred at 90° C. for 1.5 h. The reaction was then allowed to cool to rt and the methanol was evaporated in vacuo. The remaining aqueous layer was acidified with 6.0 M HCl to pH 2-3 and extracted with CH$_2$Cl$_2$ (4×10 mL). The organic layers were combined and dried over MgSO$_4$, filtered and concentrated to produce 5-(N,N-dimethylsulfamoyl)-2-(pyrrolidin-1-yl)benzoic acid (0.61 g, 2.05 mmol, 87% yield) as a white solid. $^1$H NMR (400 MHz, CDCl$_3$) δ 8.38 (d, J=2.4 Hz, 1H), 7.82 (dd, J=8.8, 2.2 Hz, 1H), 7.17 (d, J=8.7 Hz, 1H), 3.37-3.27 (m, 4H), 2.73 (d, J=0.5 Hz, 6H), 2.13-2.03 (m, 4H).

5-(N,N-Dimethylsulfamoyl)-N-(5-methylthiazol-2-yl)-2-(pyrrolidin-1-yl)benzamide NGI-1

To a vial was added 5-(N,N-dimethylsulfamoyl)-2-(pyrrolidin-1-yl)benzoic acid (0.20 g, 0.66 mmol), HBTU (0.37 g, 0.99 mmol), DIPEA (0.29 mL, 1.65 mmol) and DMF (1.0 mL) and the reaction stirred at RT for 15 minutes. Then 5-methyl thiazol-2-amine (0.11 g, 0.99 mmol) was added to the reaction and it was heated to 100° C. and stirred for 3.5 h. The this time the reaction was allowed to cool to it and diluted with water (15 mL) then extracted with CH$_2$Cl$_2$ (2×15 mL). The organic layers were combined and washed with water (4×30 mL), dried over MgSO$_4$, filtered and adsorbed to Celite then purified by reverse-phase flash chromatography (10-100% MeCN:water). The fractions containing the product were then concentrated and adsorbed to silica and purified by flash chromatography (0-5% MeOH:CH$_2$Cl$_2$) to produce 5-(N,N-dimethylsulfamoyl)-N-(5-methylthiazol-2-yl)-2-(pyrrolidin-1-yl)benzamide (0.091 g, 0.23 mmol, 35% yield). $^1$H NMR (400 MHz, CDCl$_3$) δ 12.77 (s, 1H), 7.95 (d, J=2.3 Hz, 1H), 7.73 (dd, J=9.0, 2.3 Hz, 1H), 6.89 (d, J=9.0 Hz, 1H), 6.77 (s, 1H), 3.40-3.28 (m, 4H), 2.71 (s, 6H), 2.40 (d, J=1.3 Hz, 3H), 2.05-1.95 (m, 4H). $^{13}$C NMR (125 MHz, CDCl$_3$) δ 166.30, 157.62, 149.11, 133.89, 130.95, 130.40, 127.40, 121.27, 119.30, 114.16, 50.53, 38.00, 25.75, 11.55. LCMS-UV Purity at 214 nm: 100%. HRMS (ESI): m/z calcd for C$_{17}$H$_{22}$N$_4$O$_3$S$_2$(M+H$^+$) 395.1211, found 395.1211.

The following chemical analogs were prepared according to procedures outlined elsewhere herein, unless otherwise noted.

N-(5-methylthiazol-2-yl)-5-(morpholinosulfonyl)-2-(pyrrolidin-1-yl)benzamide

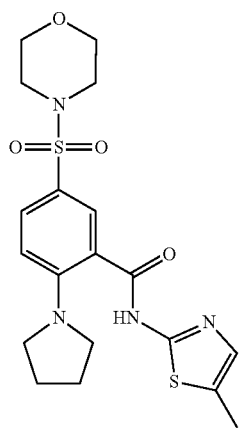 [SMILES: Cc1cnc(NC(=O)c2cc(S(=O)(=O)N3CCOCC3)ccc2N2CCCC2)s1]

Synthesized analogously to NGI-1, (0.031 g, 0.080 mmol, 22% yield). $^1$H NMR (400 MHz, CDCl3 δ 13.09 (s, 1H), 7.80 (d, J=2.3 Hz, 1H), 7.67 (dd, J=9.0, 2.3 Hz, 1H), 6.83 (d, J=9.0 Hz, 1H), 6.27 (d, J=1.3 Hz, 1H), 3.70 (dd, J=5.8, 3.7 Hz, 4H), 3.34 (q, 0.1=4.9, 3.3 Hz, 4H), 2.98-2.89 (m, 4H), 2.31 (d, J=1.3 Hz, 3H), 2.00-1.92 (m, 4H). $^{13}$C NMR (125 MHz, CDCl3 δ 166.45, 157.95, 149.10, 133.63, 130.88, 130.62, 127.47, 120.29, 119.26, 114.03, 66.03, 50.36, 45.97, 25.76, 11.50. LCMS Purity at 214 nm: 100%. HRMS: m/z calcd for C19H24N4O4S2 (M+H+) 437.1310. found 437.1321.

N-(5-methylthiazol-2-yl)-5-(piperidin-1-ylsulfonyl)-2-(pyrrolidin-1-yl)benzamide

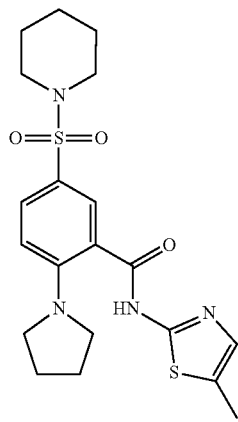 [SMILES: Cc1cnc(NC(=O)c2cc(S(=O)(=O)N3CCCCC3)ccc2N2CCCC2)s1]

Synthesized analogously to NGI-1, (0.006 g, 0.014 mmol, 11% yield). 1H NMR (400 MHz, CDCl3 δ 7.84 (d, J=2.4 Hz, 1H), 7.69 (dd, J=8.6 Hz, 2.4 Hz, 1H), 6.84 (d, J=8.6 Hz, 1H), 6.48 (d, J=1.6 Hz, 1H), 3.36-3.31 (m, 4H), 2.95 (t, J=5.4 Hz, 4H), 2.34 (d, J=1.2 Hz, 3H), 2.00-1.95 (m, 4H), 1.66-1.59 (m, 4H), 1.42-1.36 (m, 2H). 13C NMR (125 MHz. CDCl3 δ 166.3, 157.7, 149.0, 133.5, 131.0, 130.3, 127.4, 122.1, 119.2, 114.1, 50.6, 47.0, 25.8, 25.2, 23.5, 11.6. LCMS Purity at 214 nm: 95.2%. HRMS: m/z calcd for C20H26N4O3S2 (M+H+) 435.1516, found 435.1517.

N-(5-methylthiazol-2-yl)-5-(pyrrolidin-1-ylsulfonyl)-2-(pyrrolidin-1-yl)benzamide

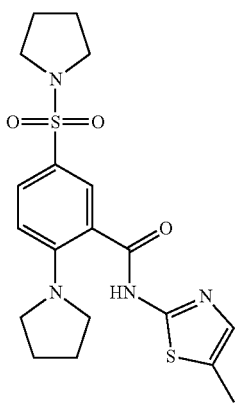 [SMILES: Cc1cnc(NC(=O)c2cc(S(=O)(=O)N3CCCC3)ccc2N2CCCC2)s1]

Synthesized analogously to NGI-1, (0.078 g, 0.19 mmol, 41% yield) as a light yellow solid. 1H NMR (400 MHz. CDCl$_3$) δ 7.94 (d, J=2.3 Hz, 1H), 7.77 (dd, J=8.9, 2.3 Hz, 1H), 6.85 (d, J=9.0 Hz, 1H), 6.47 (d, =1.3 Hz, 1H), 3.40-3.29 (m, 4H), 3.26-3.15 (m, 4H), 2.34 (d, J=1.3 Hz, 3H), 2.03-1.93 (m, 4H), 1.81-1.69 (m, 4H). 13C NMR (125 MHz, CDCl$_3$) δ 166.32, 158.14, 149.10, 132.62, 130.88, 130.33, 127.34, 123.14, 119.08, 114.28, 50.69, 47.93, 25.76, 25.16, 11.58. LCMS Purity at 214 nm: 98.7%. HRMS: m/z calcd for C19H24N4O3S2 (M+H+) 421.1356, found 421.1357.

N-(5-methylthiazol-2-yl)-5-(N-methyl-N-phenylsulfamoyl)-2-(pyrrolidin-1-yl)benzamide

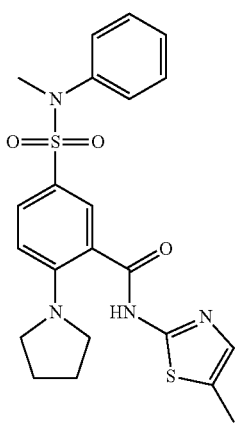 [SMILES: Cc1cnc(NC(=O)c2cc(S(=O)(=O)N(C)c3ccccc3)ccc2N2CCCC2)s1]

Synthesized analogously to NGI-1, (0.016 g, 0.035 mmol, 35% yield) as a light yellow solid. 1H NMR (400 MHz, CDCl$_3$) δ 7.67 (d, J=2.4 Hz, 1H), 7.35 (dd, J=8.6, 2.4 Hz, 1H), 7.31-7.20 (m, 3H), 7.15-7.11 (m, 2H), 6.71 (d, J=8.6 Hz, 1H), 6.30 (d, J=1.6 Hz, 1H), 3.34-3.29 (m, 4H), 3.12 (s, 3H), 2.30 (d, J=1.2 Hz, 3H), 1.98-1.93 (m, 4H). 13C NMR (125 MHz. CDCl$_3$) δ 166.4, 157.8, 148.9, 141.8, 133.8, 130.9, 130.5, 128.8, 127.2, 126.7, 122.0, 118.9, 113.8, 50.4, 38.0, 25.8, 11.5. LCMS Purity at 214 nm: 92.4%. HRMS: m/z calcd for C22H24N4O3S2 (M+H+) 457.1356, found 457.1358.

N-(5-methylthiazol-2-yl)-5-(N,N-dimethylsulfamoyl)-2-(azetidin-1-yl)benzamide

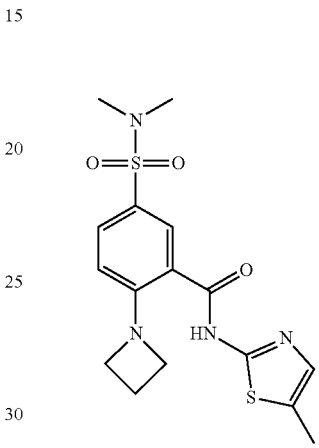

Synthesized analogously to NGI-1, (0.039 g, 0.10 mmol, 31% yield) as a white solid. 1H NMR (400 MHz, CDCl$_3$) δ 12.05 (s, 1H), 7.84 (d, J=2.2 Hz, 1H), 7.71 (dd, J=8.8, 2.2 Hz, 1H), 6.57 (d, J=8.8 Hz, 1H), 6.50 (d, J=1.5 Hz, 1H), 4.03 (t, J=7.5 Hz, 4H), 2.67 (s, 6H), 2.42-2.33 (m, 5H). 13C NMR (125 MHz, CDCl$_3$) δ 164.96, 157.28, 151.49, 134.05, 130.96, 129.86, 128.95, 127.59, 125.25, 122.16, 120.31, 117.74, 112.81, 109.30, 53.43, 38.00, 16.38, 11.55. LCMS Purity at 214 nm: 100%. HRMS: m/z calcd for C$_{16}$H$_{20}$N$_4$O$_3$S$_2$(M+H+) 381.1053, found 381.1053.

Certain analogs were prepared using an alternative coupling method in the last step of the synthetic sequence for NGI-1. In these examples, a PyBOP coupling was employed (Scheme 1).

Scheme 1.

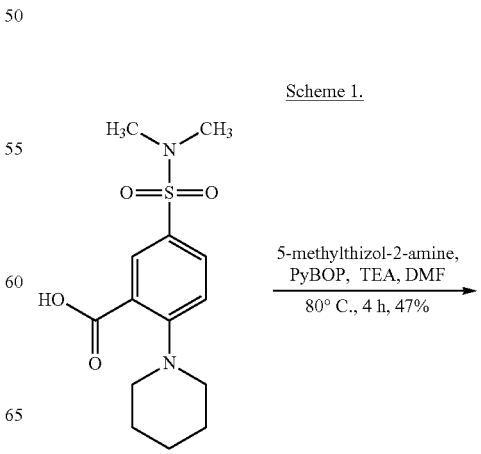

5-methylthizol-2-amine, PyBOP, TEA, DMF
80° C., 4 h, 47%

N-(5-methylthiazol-2-yl)-5-(7N-dimethylsulfamoyl)-2-(piperidin-1-yl)benzamide

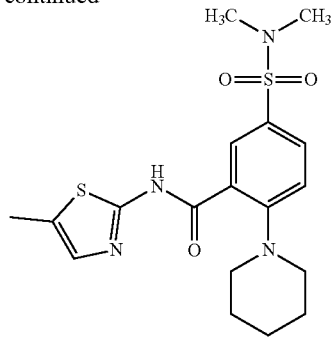

The requisite 5-(N,Ndimethylsulfamoyl)-2-(piperidin-1-yl)benzoic acid was prepared analogously to NGI-1, although the following modification was used for the last coupling step (Scheme 1).

Method B.

To a vial was added the 5-(N,N-dimethylsulfamoyl)-2-(piperidin-1-yl)benzoic acid 7 (0.10 g, 0.32 mmol) and PyBOP (0.25 g, 0.49 mmol) with DMF (3 mL). The reaction stirred at rt for 1 h after which the triethylamine (0.090 mL, 0.65 mmol) and 5-methylthiazol-2-amine (0.11 g, 0.97 mmol) were added and the reaction heated to 80° C. and stirred for 4 h. The reaction was then diluted with saturated NaHCO$_3$ (5 mL) and extracted with CH$_2$Cl$_2$ (2×6 mL). The CH$_2$Cl$_2$ was then washed with water (4×10 mL) and collected then concentrated and purified by RP MPLC (10-100% MeCN:water). The isolated peak was repurified by MPLC (0-50% EtOAc:hex) to produce N-(5-methylthiazol-2-yl)-5-(N,N-dimethylsulfamoyl)-2-(piperidin-1-yl)-benzamide CID24448707 (0.062 g, 0.152 mmol, 47% yield) as a white solid. 1H NMR (400 MHz, CDCl$_3$) δ 13.23 (s, 1H), 8.62 (d, J=2.3 Hz, 1H), 7.91 (dd, J=8.5, 2.4 Hz, 1H), 7.42 (d, J=8.4 Hz, 1H), 7.16 (d, J=1.4 Hz, 1H), 3.11-2.98 (m, 4H), 2.75 (s, 6H), 2.43 (d, J=1.2 Hz, 3H), 1.93 (p, J=5.7 Hz, 4H), 1.69 (q, J=5.9, 4.3 Hz, 2H). 13C NMR (125 MHz, CDCl$_3$) δ 161.76, 156.17, 155.87, 135.23, 132.27, 131.28, 126.22, 121.50, 55.12, 37.92, 25.93, 23.52, 11.63. LCMS Purity at 214 nm: 96.7%. HRMS: m/z calcd for C$_{18}$H$_{24}$N$_4$O$_3$S$_2$(M+H+) 409.1363, found 409.1365.

N-(p-tolyl)-5-(N,N-dimethylsulfamoyl)-2-(pyrrolidin-1-yl)benzamide

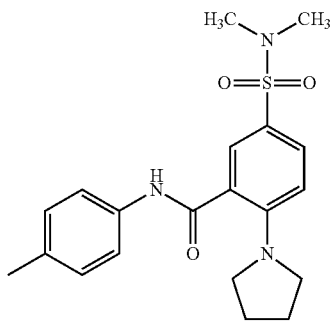 [SMILES: Cc1ccc(NC(=O)c2cc(S(=O)(=O)N(C)C)ccc2N2CCCC2)cc1]

Prepared analogously to NGI-1, although Method B was used for the last coupling step (Scheme 2), (0.048 g, 0.12 mmol, 82% yield) as a white solid. 1H NMR (400 MHz, CDCl$_3$) δ 8.12 (s, 1H), 7.75 (d, J=2.3 Hz, 1H), 7.59-7.46 (m, 3H), 7.16 (dd, J=8.4, 0.9 Hz, 2H), 6.75 (d, J=9.0 Hz, 1H), 3.46-3.31 (m, 4H), 2.64 (s, 6H), 2.34 (s, 3H), 1.99-1.87 (m, 4H). 13C NMR (125 MHz, CDCl$_3$) δ 167.10, 148.87, 135.39, 134.16, 130.22, 129.57, 129.56, 122.05, 120.65, 119.71, 114.07, 50.32, 38.01, 25.68, 20.87. LCMS Purity at 214 nm: 100%. HRMS: m/z calcd for C$_{20}$H$_{25}$N$_3$O$_3$S$_2$ (M+H+) 388.1702, found 388.1703.

N-(thiazol-2-yl)-5-(N,N-dimethylsulfamoyl)-2-(pyrrolidin-1-yl)benzamide

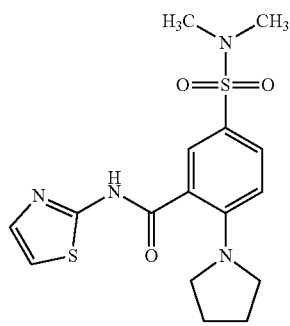 [SMILES: CN(C)S(=O)(=O)c1ccc(N2CCCC2)c(C(=O)Nc2nccs2)c1]

Prepared analogously to NGI-1, although Method B was used for the last coupling step (Scheme 2), (0.016 g, 0.42 mmol, 22% yield) as a white solid. 1H NMR (400 MHz, CDCl$_3$) δ 13.18 (brs, 1H), 7.86 (d, J=2.4 Hz, 1H), 7.71 (dd, J=8.8 Hz, 2.4 Hz, 1H), 6.88 (d, J=3.6 Hz, 1H), 6.84 (d, J=8.8 Hz, 1H), 6.71 (d, J=3.6 Hz, 1H), 3.35-3.30 (m, 4H), 2.65 (s, 6H), 1.97-1.93 (m, 4H). 13C NMR (125 MHz, CDCl$_3$) δ 166.8, 159.6, 149.0, 139.9, 131.0, 130.4, 121.0, 119.1, 114.1, 113.4, 50.4, 40.9, 38.0, 25.7. LCMS Purity at 214 nm: 97.8%. HRMS: m/z calcd for C$_{16}$H$_{20}$N$_4$O$_3$S$_2$(M+H+) 381.1052, found 381.1052.

N-cyclohexyl-5-(N,N-dimethylsulfamoyl)-2-(pyrrolidin-1-yl)benzamide

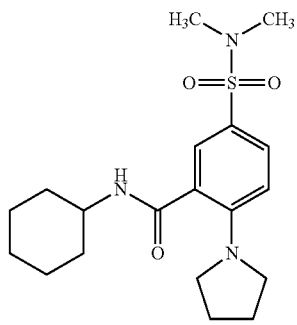 [SMILES: CN(C)S(=O)(=O)c1ccc(N2CCCC2)c(C(=O)NC2CCCCC2)c1]

Prepared analogously to NGI-1, although Method B was used for the last coupling step (Scheme 1), (0.051 g, 0.13 mmol, 89% yield) as a white solid. 1H NMR (400 MHz, CDCl$_3$) δ 7.58 (d, J=2.3 Hz, 1H), 7.51 (dd, J=8.9, 2.3 Hz, 1H), 6.68 (d, J=8.9 Hz, 1H), 5.98 (d, J=8.2 Hz, 1H), 3.98-3.81 (m, 1H), 3.42-3.31 (m, 4H), 2.62 (s, 6H), 2.06-

1.88 (m, 6H), 1.82-1.68 (m, 2H), 1.68-1.57 (m, 1H), 1.49-1.31 (m, 2H), 1.30-1.09 (m, 3H). 13C NMR (125 MHz, CDCl₃) 168.78, 148.47, 129.95, 129.37, 122.03, 120.24, 113.71, 49.84, 48.84, 37.97, 32.84, 25.63, 25.40, 24.84. LCMS Purity at 214 nm: 99.2%. HRMS: m/z calcd for $C_{19}H_{29}N_3O_3S$ (M+H+) 380.2011. found 380.2012.

N-(5-methylthiazol-2-yl)-5-(N,N-dimethylsulfamoyl)-2-(dimethylamino)benzamide

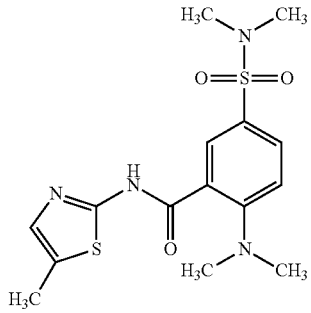 [SMILES: Cc1cnc(NC(=O)c2cc(S(=O)(=O)N(C)C)ccc2N(C)C)s1]

Prepared analogously to NGI-1, although Method B was used for the last coupling step (Scheme 1), (0.032 g, 0.087 mmol, 25% yield) as a white solid. 1H NMR (400 MHz, CDCl₃) δ 2.34 (s, 1H), 8.53 (d, J=2.3 Hz, 1H), 7.90 (dd, J=8.5, 2.4 Hz, 1H), 7.38 (d, J=8.5 Hz, 1H), 7.11 (d, J=1.3 Hz, 1H), 2.92 (s, 6H), 2.75 (s, 6H), 2.44 (d, J=1.3 Hz, 3H). 13C NMR (125 MHz, CDCl₃) δ 162.31, 156.27, 155.69, 134.71, 132.26, 131.43, 131.19, 128.22, 125.33, 120.08, 53.42, 45.03, 37.95, 29.71, 11.66. LCMS Purity at 214 nm: 100%. HRMS: m/z calcd for $C_{23}H_{34}N_4O_3S_2$(M+H+) 479.2149, found 479.2150.

N,N-Dimethyl-3-(morpholine-4-carbonyl)-4-(pyrrolidin-1-yl)benzenesulfonamide

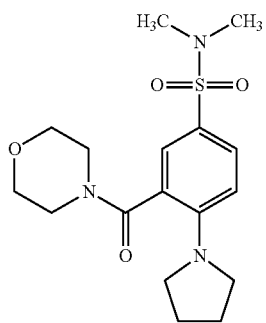 [SMILES: CN(C)S(=O)(=O)c1ccc(N2CCCC2)c(C(=O)N2CCOCC2)c1]

Prepared analogously to NGI-1, although Method B was used for the last coupling step (Scheme 1), (0.048 g, 0.13 mmol, 93% yield) as a white solid. 1H NMR (400 MHz, CDCl₃) δ 7.57 (dd, J=8.9, 2.3 Hz, 1H), 7.47 (d, J=2.3 Hz, 1H), 6.70 (d, J=8.9 Hz, 1H), 3.96-3.86 (m, 1H), 3.79-3.72 (m, 2H), 3.69-3.58 (m, 3H), 3.50-3.43 (m, 2H), 3.43-3.35 (m, 1H), 3.34-3.26 (m, 1H), 3.25-3.15 (m, 2H), 2.65 (s, 6H), 2.05-1.91 (m, 4H). 13C NMR (125 MHz, CDCl₃) δ 169.71, 148.14, 129.81, 129.15, 120.89, 119.11, 113.64, 66.56, 66.19, 49.65, 47.79, 42.06, 38.02, 25.74. LCMS Purity at 214 nm: 95.9%. HRMS: m/z calcd for $C_{17}H_{25}N_3O_4S$ (M+H+) 368.1641, found 368.1642.

N-(Benzo[d]thiazol-2-yl)-5-(N,N-dimethylsulfamoyl)-2-(pyrrolidin-1-yl)benzamide

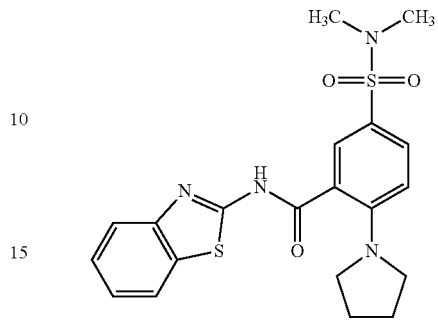

Synthesized analogously to NGI-1, (0.056 g, 0.13 mmol, 26% yield) as a white solid. 1H NMR (400 MHz, CDCl₃) δ 11.57 (s, 1H), 7.94 (d, J=2.3 Hz, 1H), 7.88-7.79 (m, 1H), 7.62 (dd, J=9.0, 2.3 Hz, 1H), 7.35-7.27 (m, 3H), 6.76 (d, J=9.0 Hz, 1H), 3.36-3.24 (m, 4H), 2.53 (s, 6H), 2.03-1.94 (m, 4H). 13C NMR (125 MHz, CDCl₃) δ 166.47, 158.67, 149.71, 147.86, 131.80, 131.54, 130.52, 126.34, 124.14, 122.37, 121.34, 120.46, 118.97, 114.64, 51.14, 37.77, 25.79. LCMS Purity at 214 nm: 96.7%. HRMS: m/z calcd for $C_{20}H_{22}N_4O_3S_2$(M+H+) 431.1209, found 431.1209.

N-(4-Methylthiazol-2-yl)-5-(N,N-dimethylsulfamoyl)-2-(pyrrolidin-1-yl)benzamide

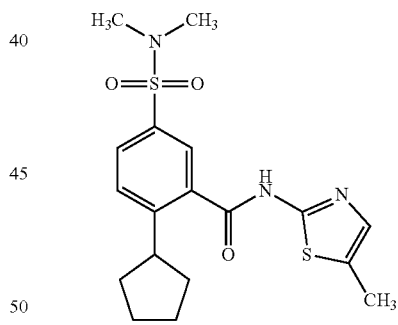

Synthesized analogously to NGI-1, (0.059 g, 0.15 mmol, 29% yield) as a white solid. 1H NMR (400 MHz, CDCl₃) δ 7.98 (d, J=2.5 Hz, 1H), 7.72 (dd, J=9.0, 2.3 Hz, 1H), 6.90 (d, J=9.0 Hz, 1H), 6.58 (d, J=1.5 Hz, 1H), 3.38-3.23 (m, 4H), 2.70 (d, J=1.4 Hz, 6H), 2.30 (s, 3H), 2.09-1.96 (m, 4H). 13C NMR (125 MHz, CDCl₃) δ 166.12, 158.69, 149.46, 146.54, 131.11, 130.50, 121.41, 119.02, 114.07, 108.22, 50.75, 40.84, 37.83, 25.74, 16.25. LCMS Purity at 214 nm: 99.7%. HRMS: m/z calcd for $C_{17}H_{22}N_4O_3S_2$(M+H+) 395.1209, found 395.1210.

Synthesis of certain analogs bearing alkyl derivatives in place of the pyrrolidine moiety required an alternative protocol. As such, a zinc-mediated cross-coupling method was employed (Scheme 2).

Scheme 2.

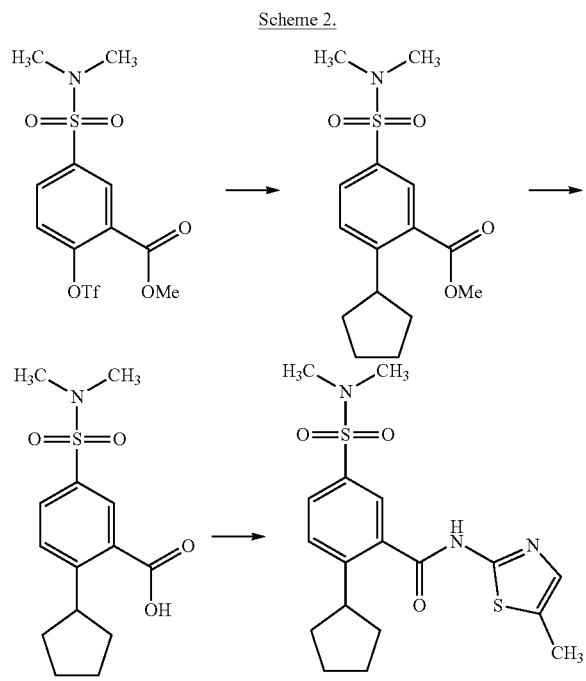

Synthetic protocol for analogs bearing non-amine derived pyrrolidone replacements. Reagents and conditions: a) lithium chloride, Pd(dppf)₂Cl2, cyclopentylzinc bromide, DMF, 0° C. to rt, 18 h, 38%, b) NaOH, MeOH/H2O, 90° C., 1.5 h, 83%; c) HBTU, DIPEA, 5-methylthiazol-2-amine, DMF, rt—100° C., 4 h, 46%.

Preparation of N-(5-methylthiazol-2-yl)-5-(N,N-dimethylsulfamoyl)-2-(cyclopentyl)benzamide

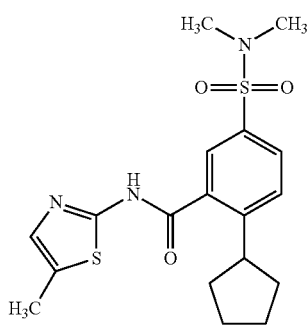 [SMILES: Cc1cnc(NC(=O)c2cc(S(=O)(=O)N(C)C)ccc2C2CCCC2)s1]

Step 1: Methyl 2-cyclopentyl-5-(N,Ndimethylsulfamoyl) benzoate

To an oven dried vial was added the methyl 5-(N,Ndimethylsulfamoyl)-2-(((trifluoromethyl)sulfonyl)oxy)benzoate (0.12 g, 0.32 mmol), lithium chloride (0.081 g, 1.90 mmol) and 1,1'-bis(diphenylphosphino) ferrocenepalladium(II) dichloride complex with toluene (0.014 g, 0.016 mmol) along with activated molecular seives. The vial was evacuated with argon 3 times and then anhydrous DMF (1.5 mL) was added. The reaction was cooled to 0° C. for 10 min and then the 0.5 M cyclopentylzinc bromide (2.85 mL, 1.43 mmol) in toluene was added. The reaction then warmed to rt and stirred for 18 h then was quenched with saturated ammonium chloride (5 mL) and extracted with EtOAc (3×6 mL). The EtOAc layers were combined, dried, filtered and adsorbed to Celite then purified by reverse-phase flash chromatography (10-100% MeCN:water) to produce methyl 2-cyclopentyl-5-(N,Ndimethylsulfamoyl) benzoate (0.037 g, 0.12 mmol, 38% yield) as a clear oil. 1H NMR (400 MHz, CDCl₃) δ 8.10 (d, J=2.0 Hz, 1H), 7.83-7.77 (m, 1H), 7.57 (d, J=8.3 Hz, 1H), 3.93 (s, 3H), 3.79 (ddd, J=17.2, 9.4, 7.6 Hz, 1H), 2.73 (s, 6H), 2.18-2.07 (m, 2H), 1.91-1.68 (m, 6H).

Step 2: 5-(N,N-Dimethylsulfamoyl)-2-(cyclopentyl)benzoic acid

To a vial was added methyl 2-cyclopentyl-5-(N,N-dimethylsulfamoyl)benzoate (0.054 g, 0.17 mmol), MeOH (4 mL) and 5.0 M NaOH (0.17 mL, 1.73 mmol) and the reaction stirred at 90° C. for 1.5 h. The reaction was then allowed to cool to rt and the methanol was evaporated in vacuo. The remaining aqueous layer was acidified with 6.0 M HCl to pH 2-3 and extracted with CH₂Cl₂ (4×10 mL). The organic layers were combined and dried over MgSO4, filtered and concentrated to produce 2-cyclopentyl-5-(N, Ndimethylsulfamoyl) benzoic acid (0.043 g, 0.15 mmol, 83% yield) as a white solid. 1H NMR (400 MHz, CDCl₃) δ 8.28 (d, J=2.1 Hz, 1H), 7.87 (dd, J=8.3, 2.1 Hz, 1H), 7.62 (d, J=8.3 Hz, 1H), 4.01-3.85 (m, 1H), 2.75 (s, 6H), 2.23-2.13 (m, 2H), 1.94-1.68 (m, 4H), 1.68-1.51 (m, 2H).

Step 3: N-(5-methylthiazol-2-yl)-5-(N,N-dimethylsulfamoyl)-2-(cyclopentyl)benzamide Synthesized analogously to NGI-1, except the cyclopentyl unit was introduced via an alternative coupling protocol (Scheme 2), (0.026 g, 0.066 mmol, 46% yield) as a white solid. 1H NMR (400 MHz, CDCl₃) δ 13.27 (s, 1H), 7.90 (dd, J=8.3, 2.0 Hz, 1H), 7.82 (d, J=2.0 Hz, 1H), 7.65 (d, J=8.3 Hz, 1H), 5.66 (d, J=1.3 Hz, 1H), 3.45-3.27 (m, 1H), 2.71 (s, 6H), 2.27 (d, J=1.3 Hz, 3H), 2.17-2.05 (m, 2H), 1.81 (m, J=6.3, 1.9 Hz, 2H), 1.74-1.50 (m, 4H). 13C NMR (125 MHz, CDCl₃) 166.40, 157.74, 150.73, 136.18, 133.56, 132.94, 129.49, 127.74, 127.63, 126.33, 42.22, 37.84, 35.19, 25.88, 11.46. LCMS Purity at 214 nm: 95.6%. HRMS: m/z calcd for $C_{18}H_{23}N_3O_3S_2$(M+H+) 394.1240, found 394.1241.

Example 2: High Throuput Screens for Inhibitors of N-Linked Glycosylation

A high throughput screen of 358,301 compounds from the National Institutes of Health Molecular Libraries Small Molecule Repository (MLSMR) was performed using a gain of function, cell-based assay for N-linked glycan site occupancy (Contessa, et al., Clin Cancer Res 2010, 16, 3205-3214: Bennett, et al., Transl Oncol 2013, 6, 382-391).

The primary screen was developed in the D54 glioma cell line using a modified P. pyralis luciferase gene (ER-LucT) that is ER translated and glycosylated at three N-linked glycosylation consensus sequences. Glycosylation of the reporter inactivates luciferase enzymatic activity providing a robust methodology to detect inhibition of this process. D54 cells expressing a non-ER translated luciferase (LucT) insensitive to inhibition of N-linked glycoysation were used as a secondary screen for false positives. An overview of the HTS strategy including primary, secondary, and tertiary screening is presented in FIG. 1A. The primary screen was performed in duplicate and values were normalized to the average of positive control wells (Tunicamycin) minus averaged neutral vehicle treated wells per run. Compounds with replicate activity greater than three standard deviations above the mean average of control wells were selected for further study. A subset of 1,845 compounds met this criterion, and were advanced to simultaneous retesting in both the primary screen and a secondary (false positive) cell-based screen. A subset of 730 compounds were further advanced after demonstration of a 50% activating concentration ($AC_{50}$) less than 10 µM and no activity in the secondary screen. Compounds were further triaged from consideration by consulting the Pubchem bioassay database and deprioritizing compounds showing a promiscuity rate higher than 5% across assays or by removing PAINS scaffolds (Baell, et al., J Med Chem 2010, 53, 2719-2740). Remaining compounds were assessed by medicinal chemistry review to score synthetic tractability and known issues with instability, poor solubility, or toxicity. This analysis yielded 39 compounds that were tested in a cell-free assay to detect luciferase inhibitors (Auld, et al., Proc Natl Acad Sci USA 2010, 107, 4878-4883) and by western blot analysis to detect gel mobility changes of the luciferase reporter, consistent with inhibition of N-linked glycosylation. This approach identified one aminobenzamidosulfonamide compound that blocked N-linked glycosylation.

Figure 1B:
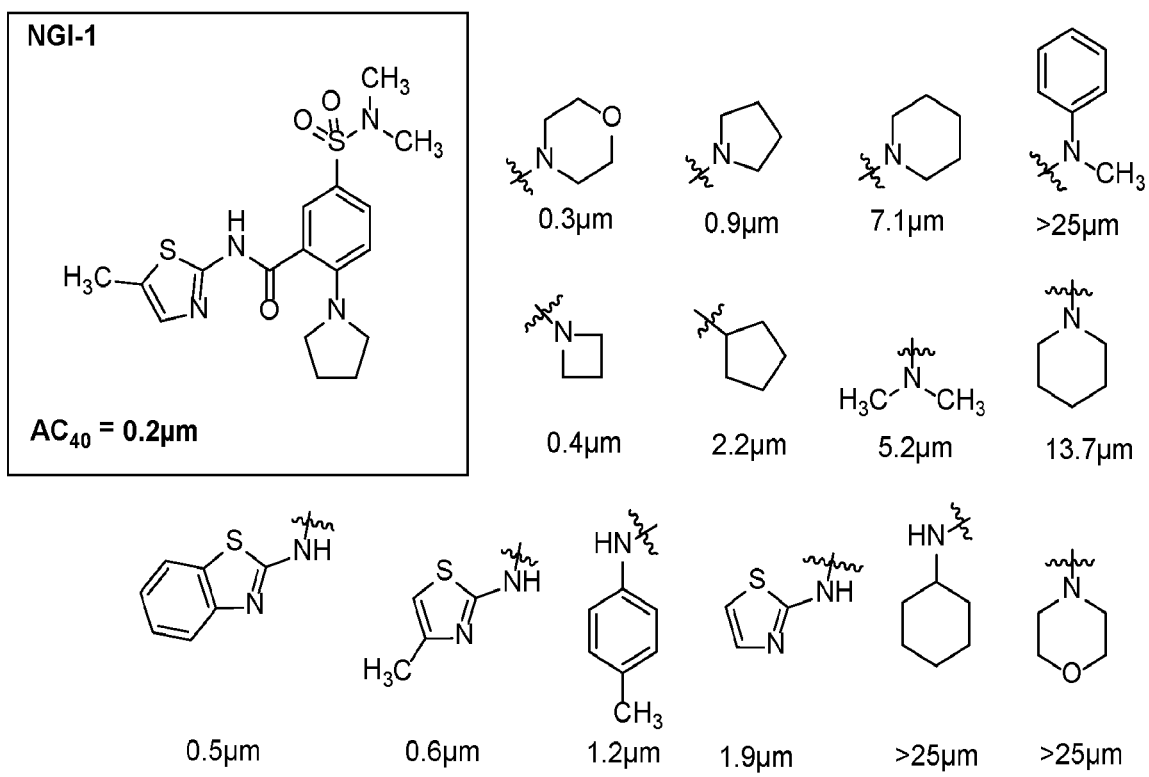

To better understand the connection between structure and activity, analogs were prepared and tested in the D54-ERLucT cell based assay for inhibition of N-linked glycosylation (FIG. 1B). The assay was used to estimate and compare $AC_{40}$ values among analogs and to guide the design of improved compounds that inhibited N-linked glycosylation. This effort generated 36 unique compounds with modifications to the amine component of the sulfonamide functionality (red), the pyrrolidine moiety (blue) or the methylaminothiazole group (green). Generally, incorporation of larger sulfonamides (i.e., larger secondary amines appended to the sulphone) was not well tolerated, resulting in erosion of potency (7 analogs). However, steric interactions could be mitigated by the introduction of a hydrogen bond accepting oxygen in a larger cyclic amine. Thus, morpholine was determined to be an acceptable surrogate for the dimethylamine component of the sulfonamide (FIGS. 1A-1D). The pyrrolidine group (blue) was replaced with various alkyl, cycloalkyl, and amine groups (7 compounds). The aminothiazole moiety was derivatized most extensively of all three regions (green highlighted area, 22 analogs). Elaboration or simplification of the thiazole itself was permitted, though any attempt to replace the thiazole with another heterocycle or substituted phenyl ring was inferior to the parent compound in terms of potency. The activity for all analogs is reported in Table 1, and their corresponding IUPAC names are listed in Table 2. Analogs were also tested for toxicity in HepG2 and HEK293 cells using the Celltiter Glo viability assay after 72 h of compound exposure, and all analogs showed no cell toxicity liability ($EC_{50}$>30 µM: Table 1). Analogs with the highest potency in the luciferase assay were retested with western blot analysis to insure that measurements of luciferase activation corresponded to loss of N-linked glycosylation.

Figure 1C:
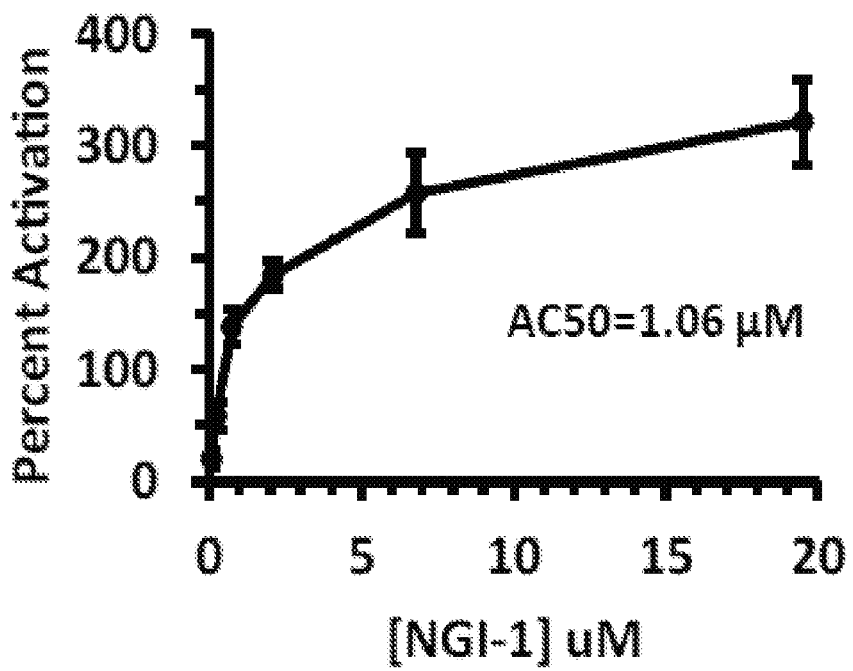

These efforts revealed a small molecule chemical probe, 5-(N,N-Dimethyl sulfamoyl)-N-(5-methylthiazol-2-yl)-2-(pyrrolidin-1-yl)benzamide designated as N-linked Glycosylation Inhibitor-1 (NGI-1), with N-linked glycosylation inhibitory activity that lacked cell toxicity. The $IC_{50}$ of NGI-1 in intact D54 ER-LucT cells in culture was estimated to be 1.06 µM (FIG. 1C). Western blot analysis of NGI-1 treated cell cultures also demonstrated dose response loss of luciferase N-linked glycosylation that directly corresponds to the ~1 µM in vitro $IC_{50}$ (FIG. 1D). Notably, unlike tunicamycin, NGI-1 did not completely abolish all N-linked glycoyslation even at doses that were 25 times the estimated $IC_{50}$. This distinctive inhibitory pattern suggested that NGI-1 has a different mechanism of action and likely a different cellular target from that of tunicamycin.

In summary, this HTS effort has identified a potent and cell permeable chemical probe that inhibits N-linked glycosylation and whose supporting data suggests a distinct mechanism of action than that of tunicamycin.

Example 3: NGI-1 Disrupts Oligosaccharyltransferase Function

Efficient N-linked glycosylation requires a series of coordinated enzymes and accessory proteins because more than 30 gene products involved in N-linked glycosylation. Any of the 30 gene product is a potential candidate for the biologic target of NGI-1. To delimit the potential targets of NGI-1, glycosylation defective CHO Lec15 and Lec35 cells were used. These cells have loss of DPM2 and MPDU1 function, respectively, and synthesize truncated $Man_5GlcNac_2$ LLOs. Stable cell lines expressing the ER-LucT were generated in both Lee 15 and Lec35 to test the effect of NGI-1 and tunicamycin on N-linked glycosylation. DPAGT1, the target of tunicamycin, is present and active in both cell lines and tunicamycin treatment was found to cause marked instability of the luciferase protein (FIG. 2A). Results with NGI-1 treatment were similar, indicating that the target of NGI-1 is also present and active in both cell lines. This data suggested that the biologic target of NGI-1 is required for either synthesis of the $Man_5GlcNac_2$ LLO species or for its transfer to the target protein. To differentiate between these possibilities FACE analysis was performed to determine the effect of NGI-1 on LLO synthesis (FIG. 2B). In these experiments tunicamycin blocked all LLO production, consistent with inhibition of the enzyme that catalyzes the first committed step in LLO synthesis (DPAGT1). In contrast NGI-1 significantly increased levels of the $Glc_3Man_9Glcnac_2$ LLO by 31% (p<0.01), indicating that NGI-1 does not abrogate LLO synthesis but instead reduces consumption of LLOs. The observed increase in mature LLO substrate coupled with decreased protein glycosylation thus suggests that NGI-1 blocks the transfer of LLOs to recipient glycoproteins.

Figure 2C:
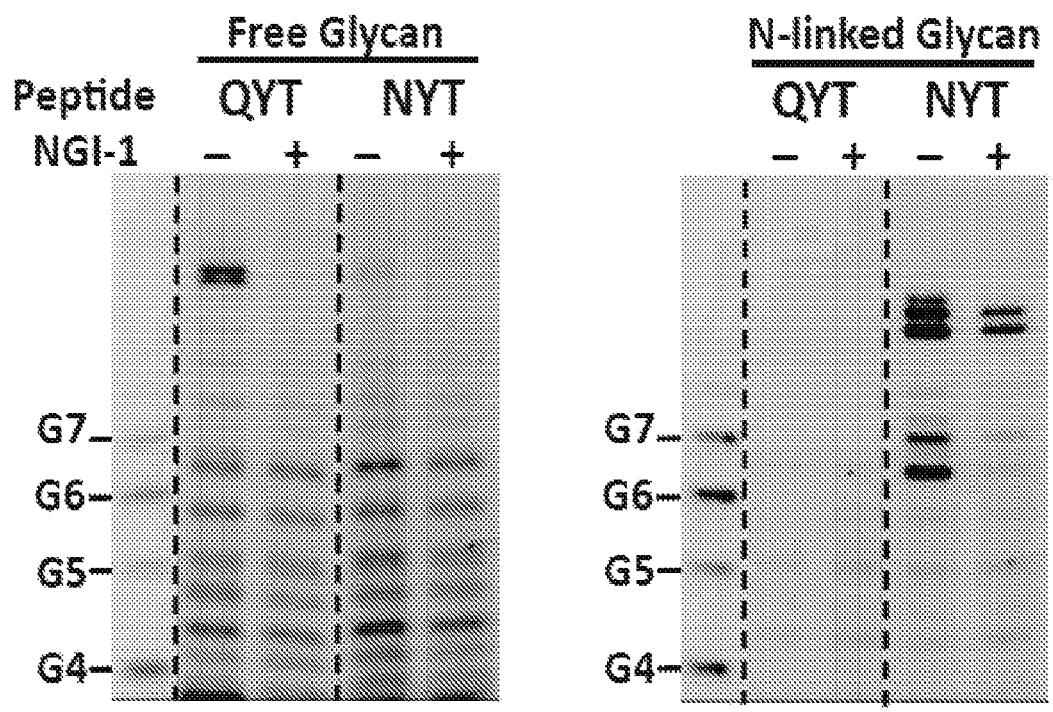
Figure 2D:
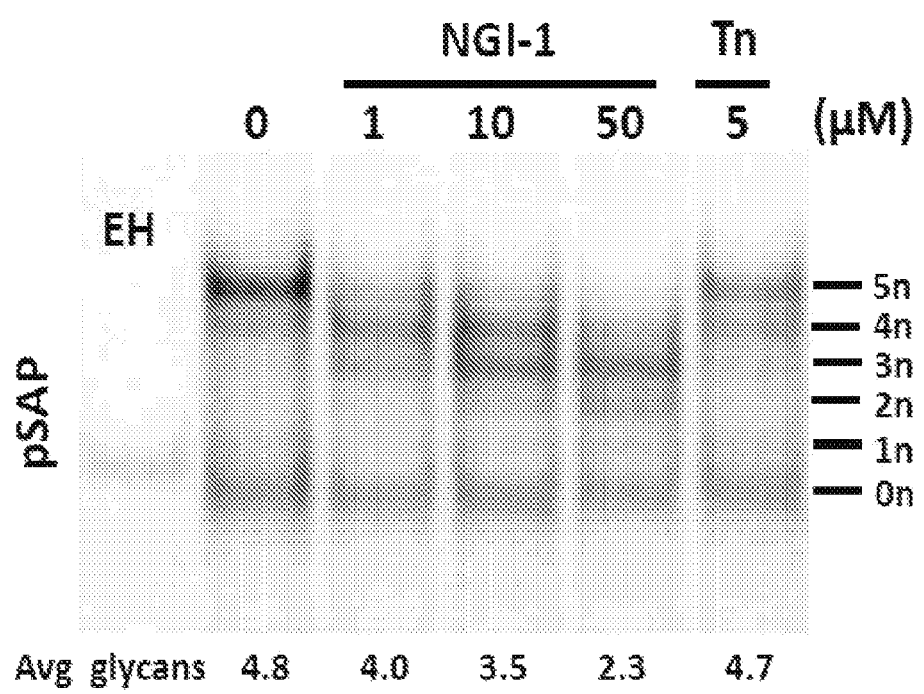

The OST is an ER resident multi-subunit complex that cleaves LLOs and transfers the oligosaccharide to a protein encoded N-linked glycosylation consensus sequence (NXT/S). The OST also cleaves LLOs and releases oligosaccharides as free glycans in the ER lumen. Both enzymatic products of the OST, free glycans and protein glycans, were therefore determined with and without NGI-1 treatment using optimized conditions in streptolysin-O permeabilized CHO cells (FIG. 2C). Addition of a control peptide without the N-linked glycosylation consensus sequence (QYT) led to readily detectable levels of free glycans (left panel), while addition of an acceptor peptide containing the consensus sequence (NYT) followed by PNGase treatment led to detection of cleaved peptide glycans (right panel). NGI-1 substantially reduced the production of both free and cleaved glycans under the respective experimental conditions providing further evidence that OST is the target of NGI-1. To isolate the activity of the OST, canine pancreas microsomes were used with in vitro translation of prosaposin (pSAP) mRNA to provide high concentrations of LLO substrate, OST enzyme, and a glycoprotein acceptor in a cell free system. NGI-1 showed a dose dependent inhibition of pSAP N-linked glycosylation (FIG. 2D), demonstrating independence from de novo synthesis of LLOs, proteins, or other cellular factors. Without wishing to be limited by any theory, this work provides strong evidence that NGI-1 targets the OST to block N-linked glycosylation.

Figure 2E:
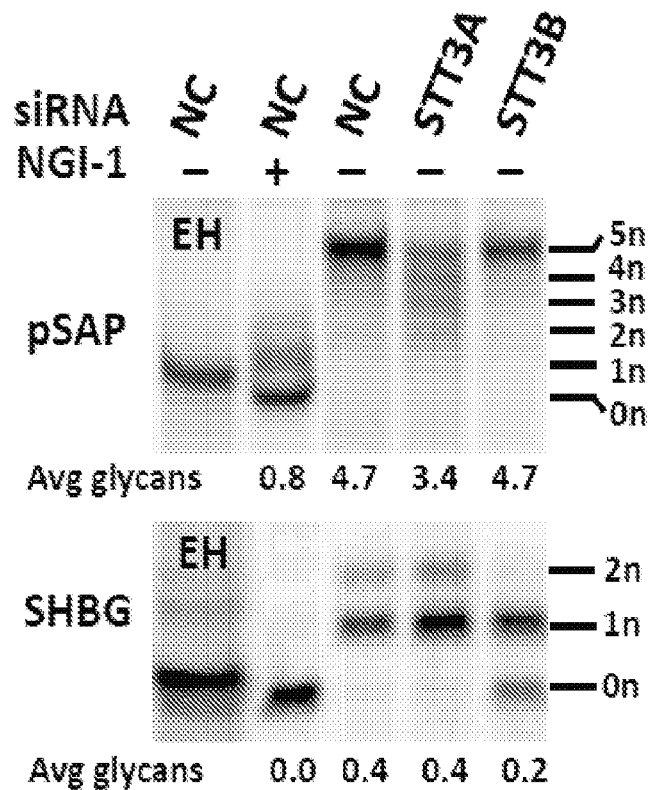
Figure 2F:
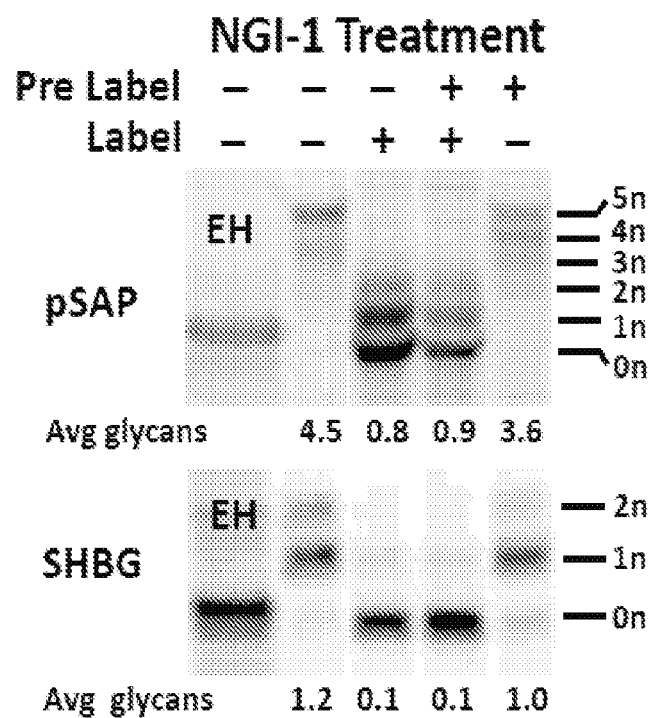
Figure 2G:
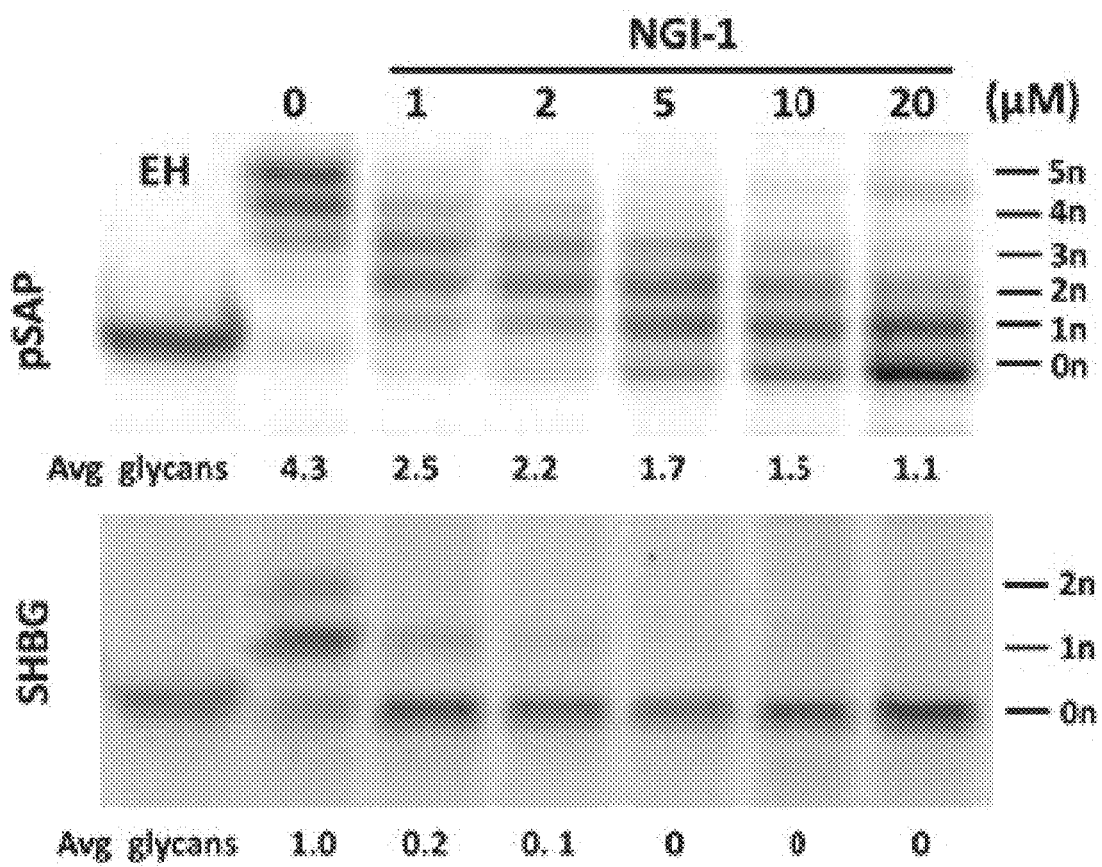
Figure 2H:
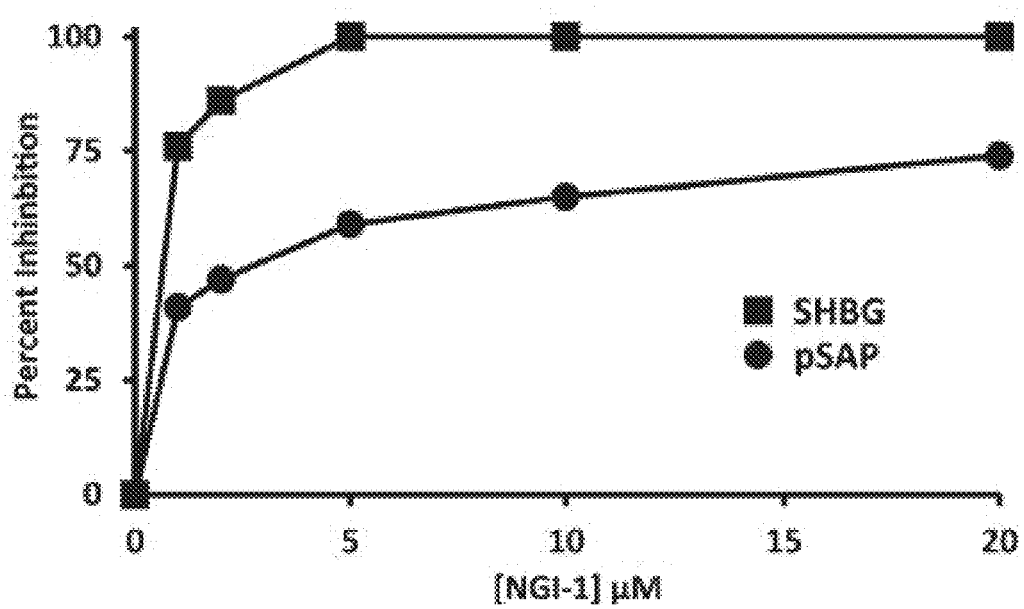
Figure 2I:
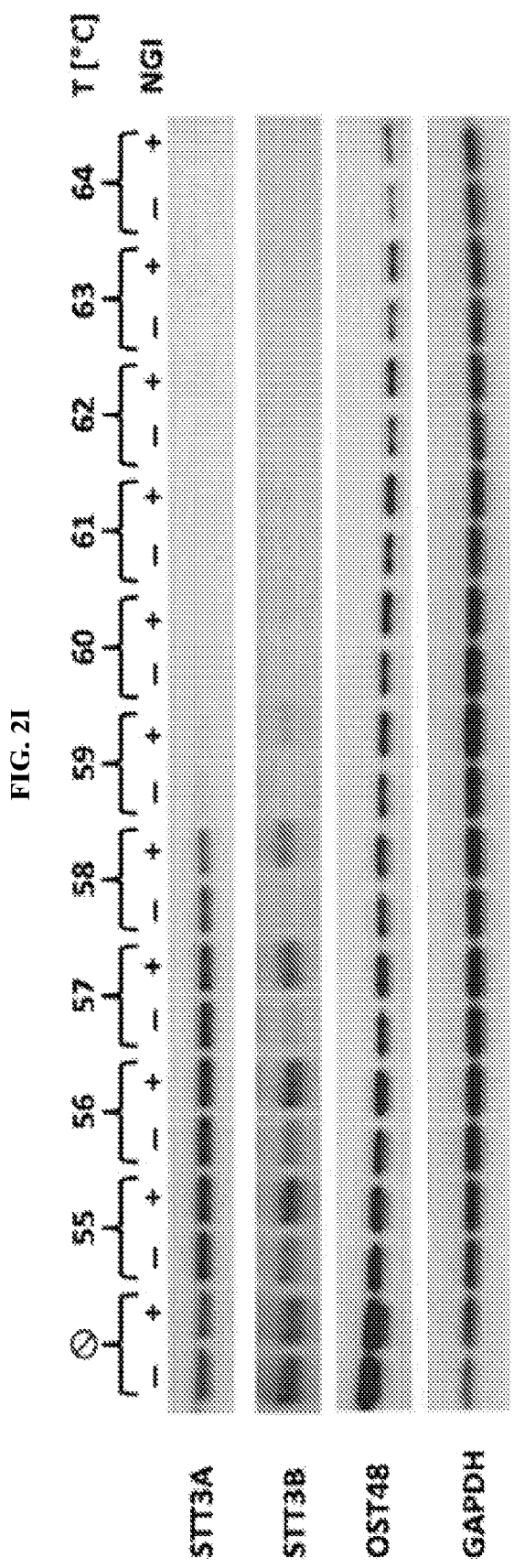

Mammalian cells encode two isoforms of the catalytic subunit of the OST; STT3A and STT3B. Knockdown of each subunit has differential effects on specific protein N-linked glycosylation sites. For example pSAP has five sites that are blocked by STT3A knockdown alone, and steroid hormone binding globulin (SHBG) has one site that is blocked by STT3B knockdown alone. Because of the incomplete effect of NGI-1 on blocking N-linked glycosylation, it was investigated whether the inhibitor was isoform specific (FIG. 2E). NGI-1 treatment for 24 h did not phenocopy knockdown of STT3A or STT3B and instead reduced glycosylation of all sites on pSAP and SHBG. These results suggest that NGI-1 is a not an STT3 isoform specific inhibitor of the OST.

Pulse labeling of pSAP and SHBG in Hela cells was also used to investigate the temporal relationships for OST inhibition. Cells were treated with NGI-1 either 24 h prior to metabolic labeling, during 20 min of labeling only, or for both times. NGI-1 blocked N-linked glycosylation of pSAP and SHBG when introduced during the metabolic labeling pulse alone; however, omission of NGI-1 during this time was sufficient to restore N-linked glycosylation. This result provides direct evidence that NGI-1 is a reversible OST inhibitor.

Example 4: NGI-1 Blocks Glycosylation and Cell Surface Expression of EGFR

The EGFR is a highly glycosylated transmembrane RTK protein with eleven consensus N-linked glycosylation sites in the extracellular domain. This cell surface growth factor receptor is a key driver of proliferation and survival signaling in malignant tumors.

Figure 3A:
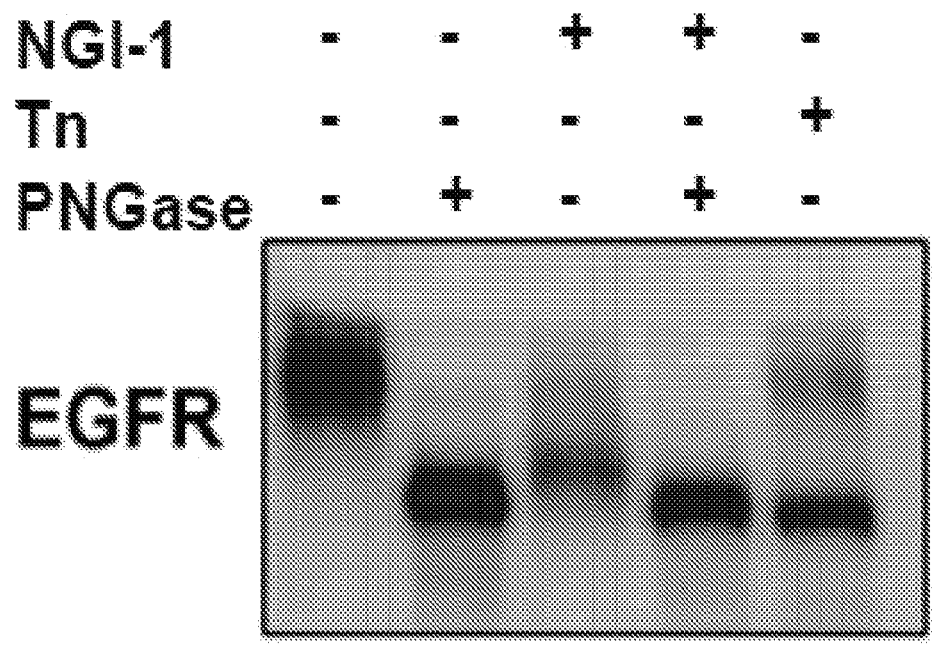
FIGS. 3A-3F illustrate the finding that NGI-1 disrupts EGFR glycosylation and cell surface expression.

The effects of OST inhibition with NGI-1 on EGFR function were investigated. NGI-1 blocked EGFR N-linked glycosylation in lung adenocarcinoma cells as assessed by decreased molecular weight on SDS-PAGE (FIG. 3A). However, a residual amount of glycosylation was also indicated by gel mobility differences from that of PNGase treated controls or from samples where LLO synthesis was blocked with tunicamycin. This mobility difference was abolished by digestion of NGI-1 treated samples with PNGase, confirming that NGI-1 treatment blocks the transfer of most, but not all, N-linked glycans to the EGFR.

Figure 3B:
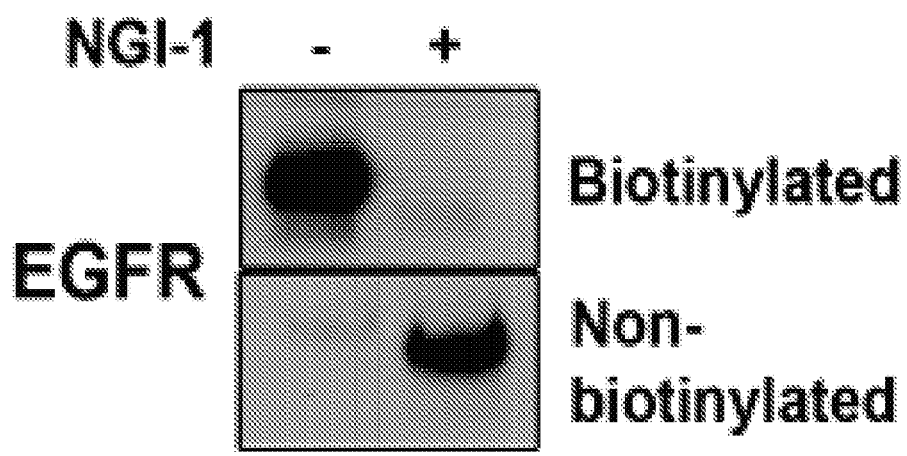
Figure 3C:
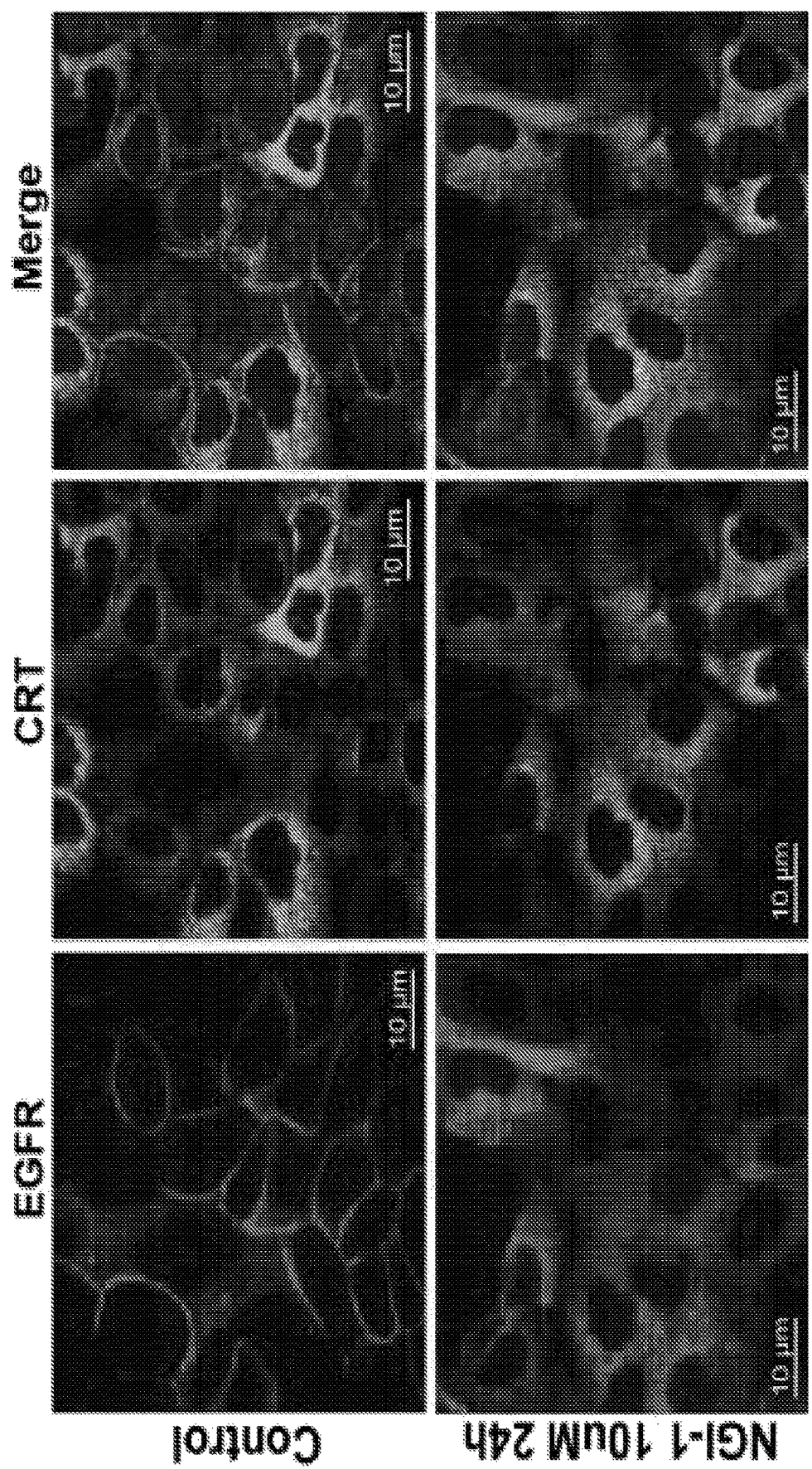
Figure 3D:
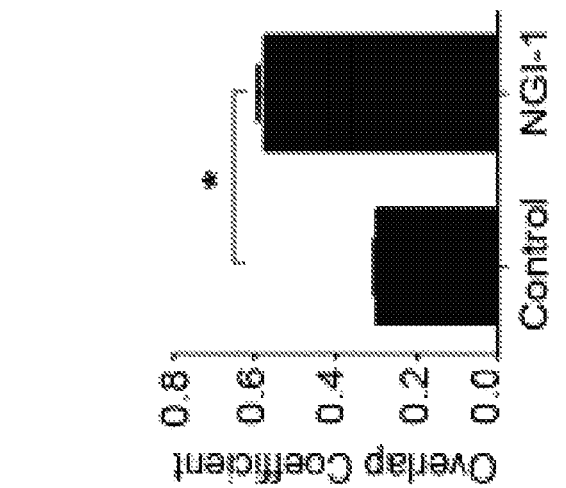
Figure 3D:
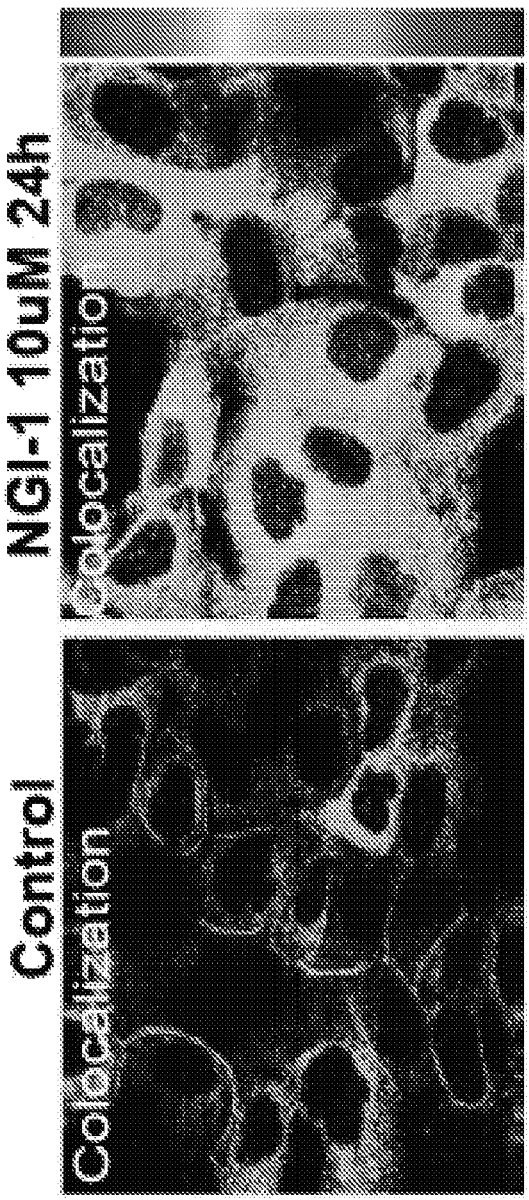
Figure 3E:
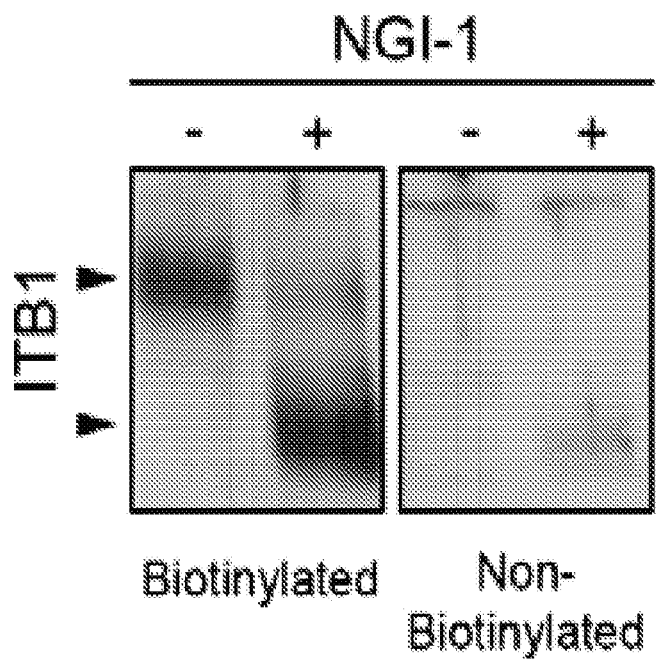
Figure 3F:
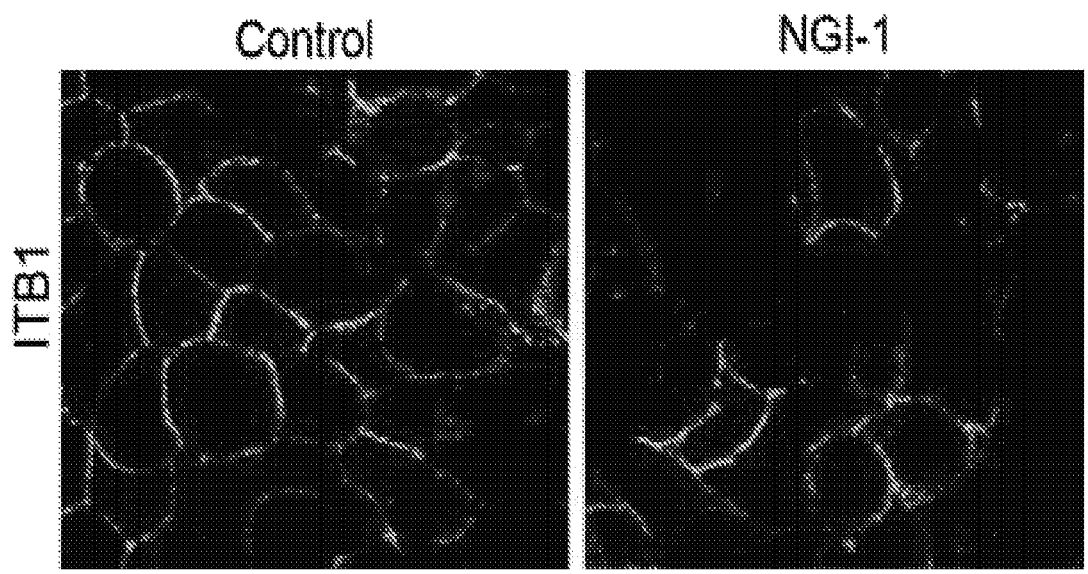
Figure 7A:
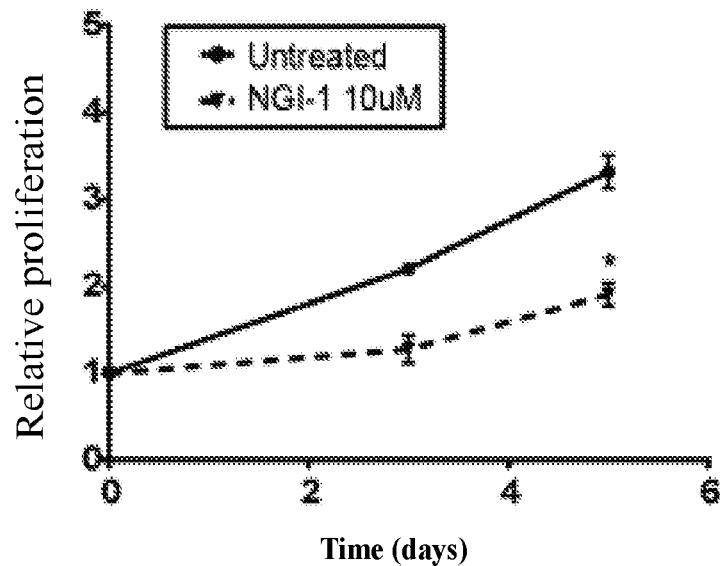
FIGS. 7A-7D illustrate EGFR kinase domain mutant cell lines growth inhibition and cell cycle arrest response to NGI-1.
Figure 7B:
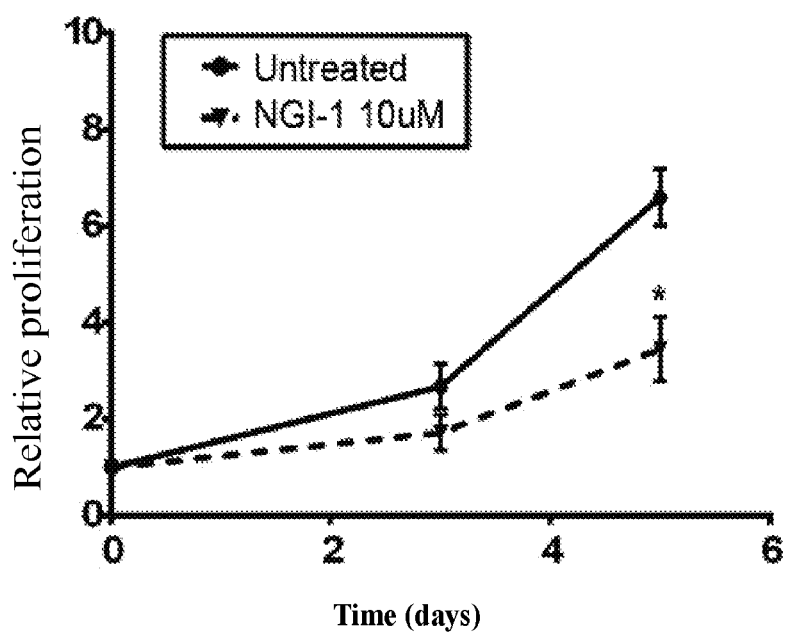
Figure 7C:
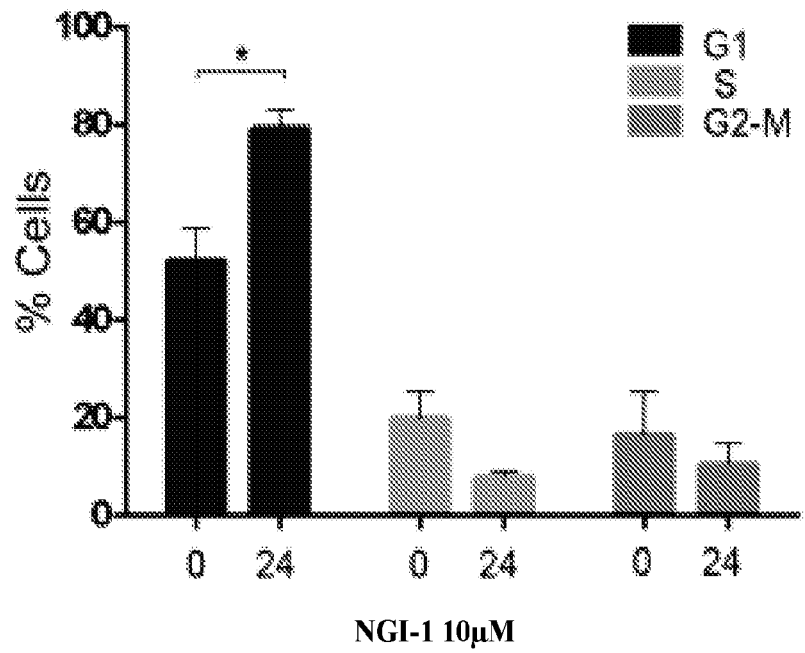
Figure 7D:
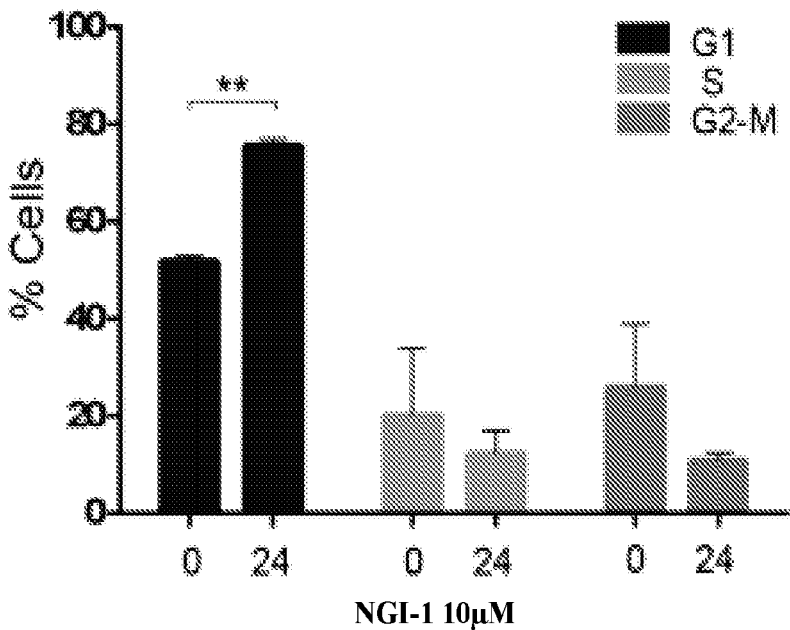

N-linked glycosylation is a critical step for the quality control and trafficking of transmembrane glycoproteins like the EGFR. To determine the effect of NGI-1 on EGFR distribution within the cell, membrane impermeable biotin labeling of intact cells followed by streptavidin precipitation was performed (FIG. 3B). In control samples EGFR was biotinylated, consistent with its plasma membrane expression, however, in NGI-1 treated cells the EGFR was predominantly found in the non-biotinylated intracellular fraction suggesting a change in cellular localization. Confocal microscopy of EGFR (red) and the ER-resident protein calreticulin (CRT; green) was then undertaken in H3255 lung adenocarcinoma cells to define the effect of NGI-1 on EGFR localization (FIG. 3C). In control samples EGFR immunofluorescence was discretely localized to the plasma membrane, however, 24 h of NGI-1 treatment caused a dramatic shift of the EGFR to an intracellular compartment without altering the cellular localization of CRT. Colocalization of EGFR and CRT was then quantified using Image J Colormap Software (FIG. 3D) and showed a significantly increased of positive correlation (p<0.05) for signal association. Identical results were observed for the HCC827 NSCLC line (FIG. 7B). Without wishing to be limited by any theory, these results suggest that OST inhibition with NGI-1 blocks EGFR trafficking to the cell surface and that misglycosylated receptors are retained in the ER and secretory pathway.

Example 5: NGI-1 Blocks Proliferation of EGFR Kinase Domain Mutant NSCLC

Figure 4A:
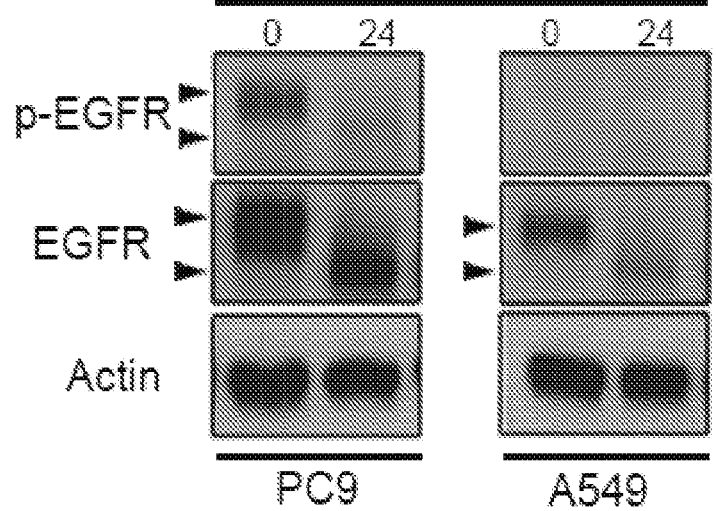
FIGS. 4A-4H illustrate the finding that NGI-1 blocks RTK driven proliferation.
Figure 4B:
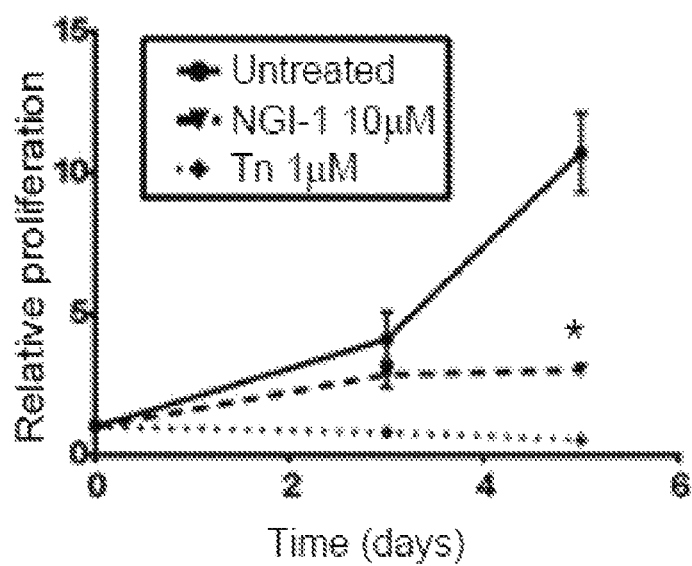
Figure 4C:
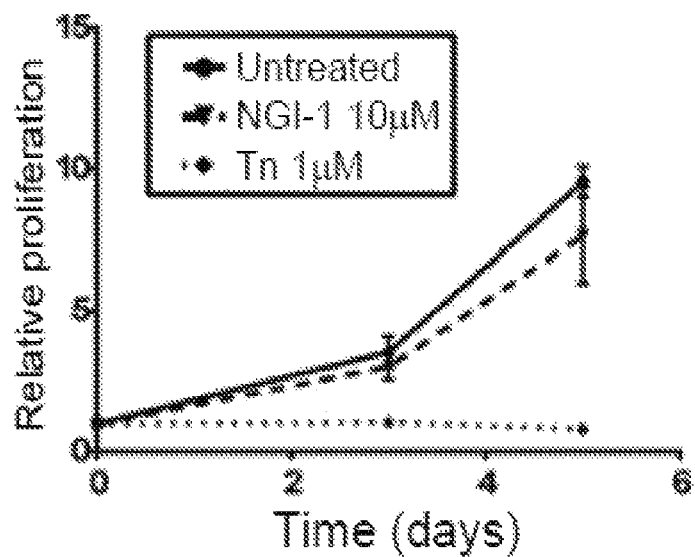
Figure 8:
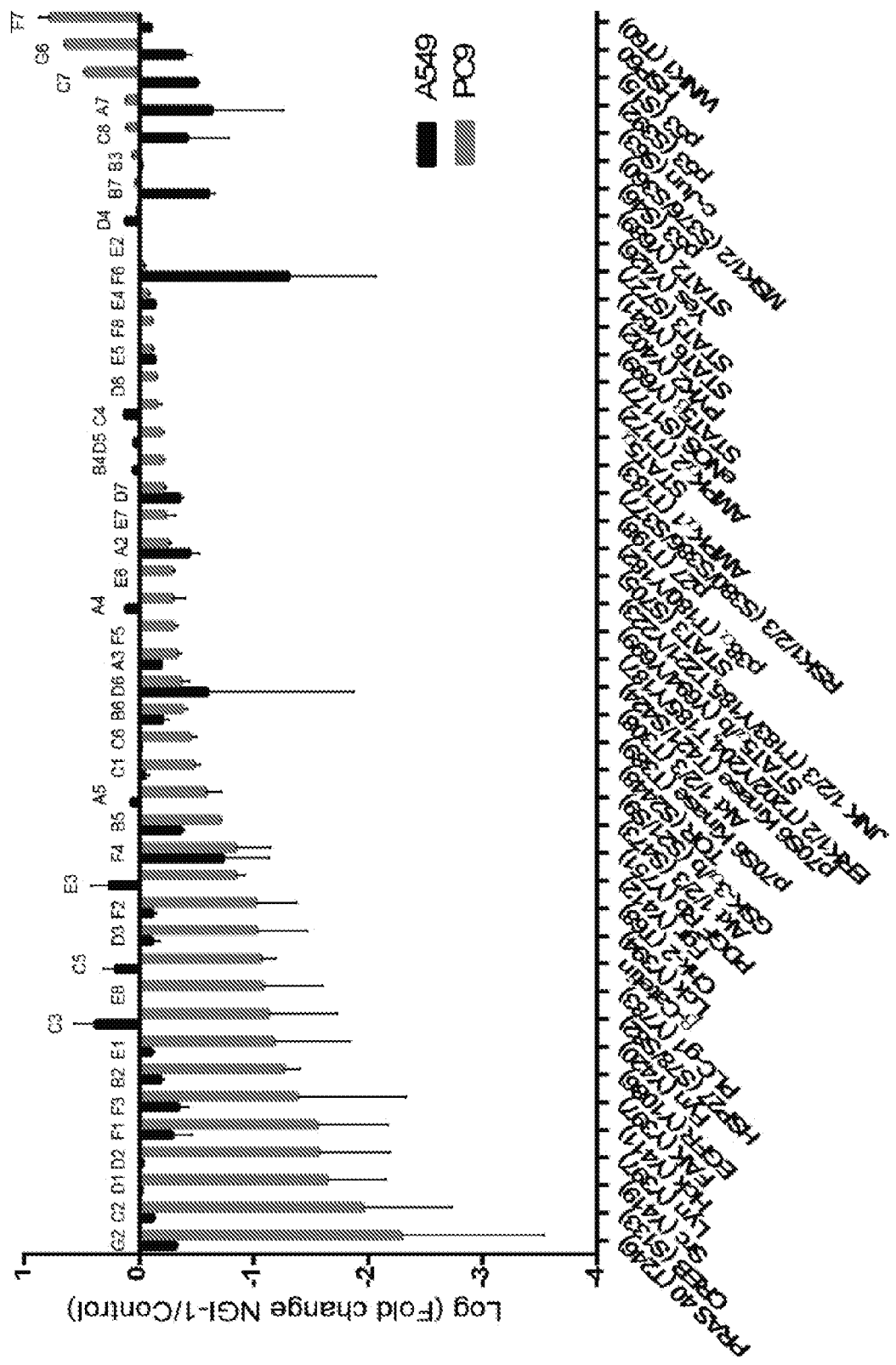
FIG. 8 is a histogram illustrating protein phosphorylation profiles of A549 and PC9 cells analyzed to assess their response to 10 μM NGI-1 for 24 h using a phospho-protein array. The levels of phosphorylated protein were assessed using phospho-specific antibodies and chemiluminescent detection. Histogram profiles of normalized pixel densities obtained by the chemiluminescent detection for each protein under the different condition assayed. A dramatically decrease in phosphospecific signaling proteins was evident in PC9 treated cells with respect to control cells and in comparison with A549.

Mutation of the EGFR kinase domain (KD) is present in approximately 10% of lung adenocarcinomas in western populations, and these tumors are dependent on EGFR RTK signaling for proliferation. Because NGI-1 affects EGFR glycosylation and localization, the effects of this inhibitor on EGFR-dependent signaling were also examined. NGI-1 blocked phosphorylation of KD mutant EGFR in PC9 cells after treatment for 1 day (FIG. 4A), and after 3 days reduced subsequent cell proliferation by more than 90% in MTT assays (p<0.001; FIG. 4B). In contrast, the A549 cell line, which harbors a downstream activating KRAS mutation (G12S), continued to proliferate after NGI-1 exposure (FIG. 4C) despite effective blockade of EGFR glycosylation. H3255 and HCC827, two additional cell lines with EGFR KD mutations, were also found to be sensitive to NGI-1 treatment (FIG. 8), demonstrating the sensitivity of this genotype to NGI-1 treatment. The results with NGI-1 are in contrast to those obtained with tunicamycin which immediately blocks proliferation in both cell lines (FIGS. 4B-4C).

Figure 4D:
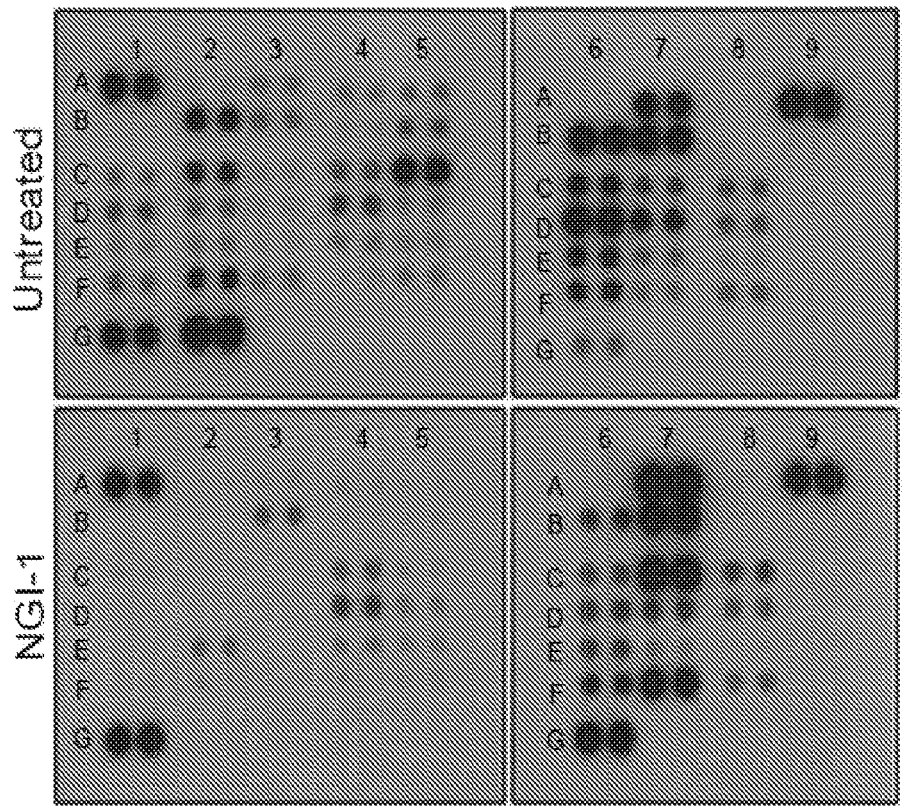
Figure 4E:
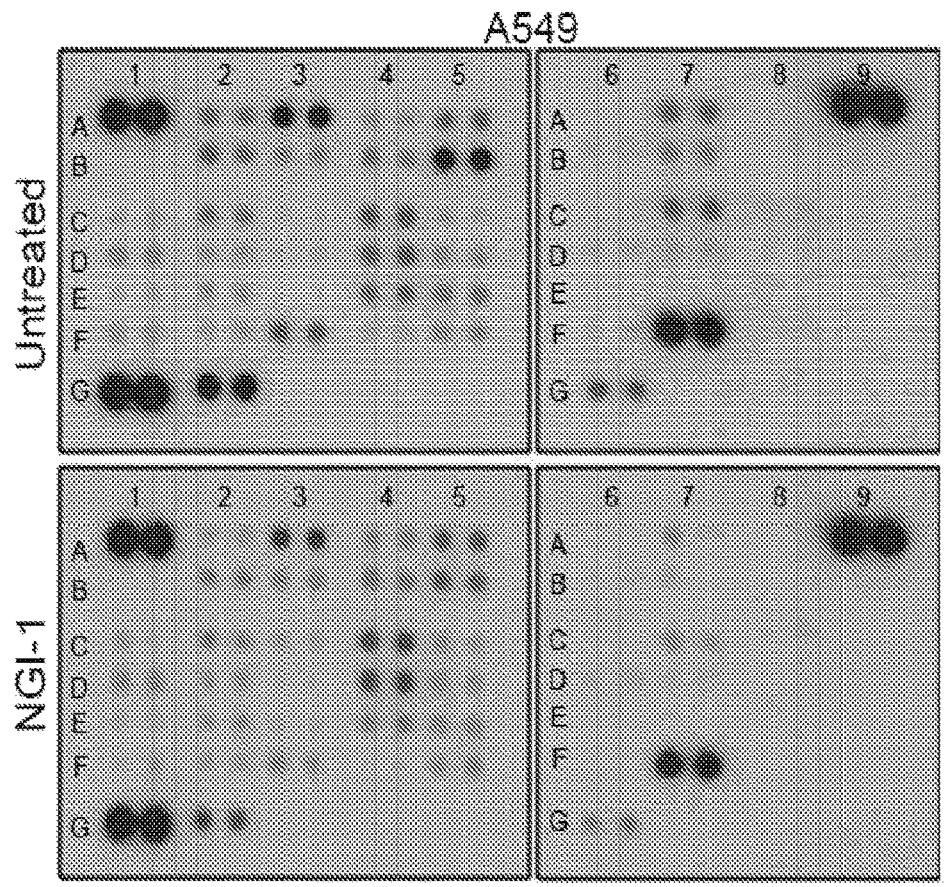
Figure 9A:
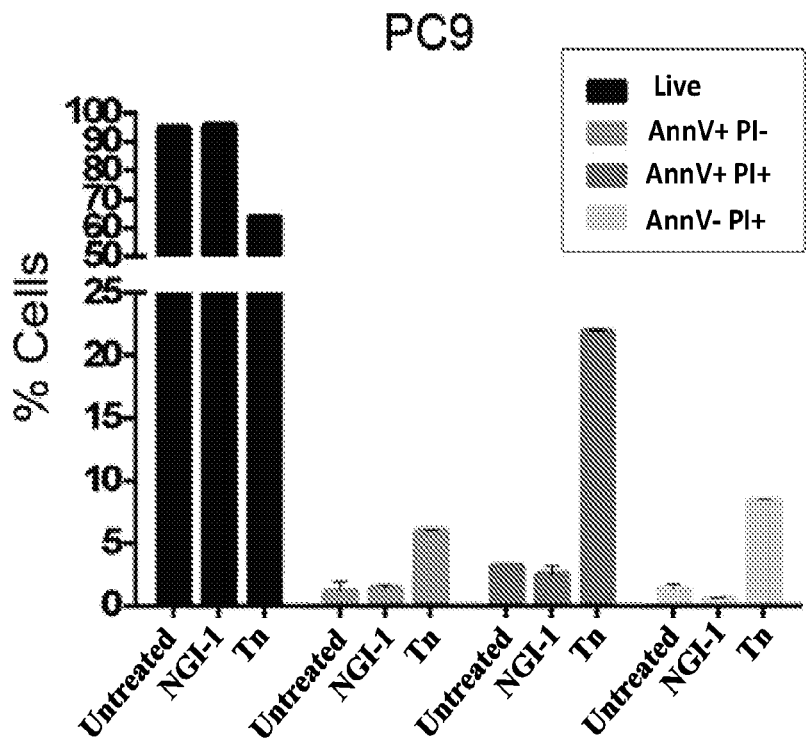
FIG. 9A illustrates the finding that NGI-1 does not induce apoptosis in PC9 cells.
Figure 9B:
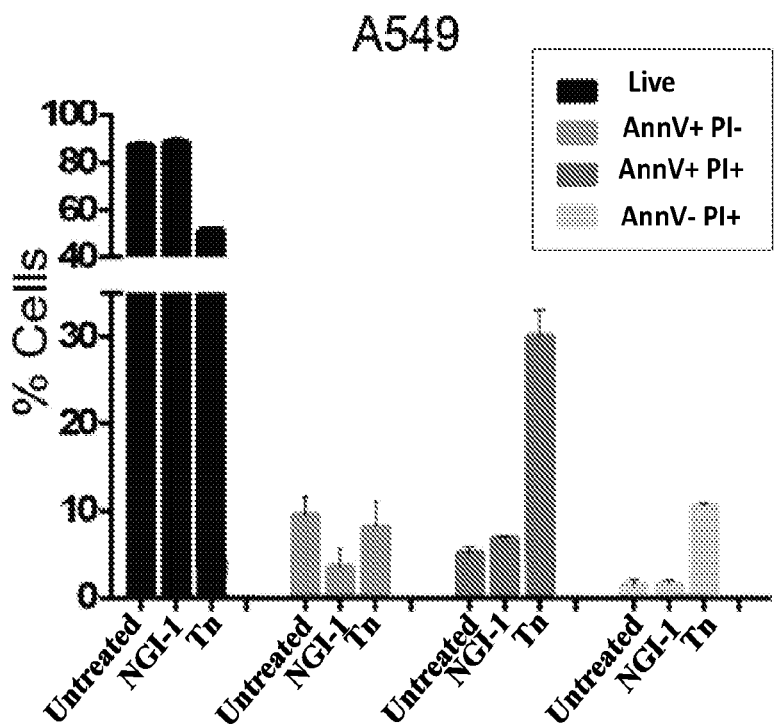
FIG. 9B illustrates the finding that NGI-1 does not induce apoptosis in A549 cells. Analysis of apoptosis susceptibility in A549 and PC9 NSCLC cell lines followed treatment with NGI-1 10 μM or Tn 1 μM for 2 days was done by flow cytometry after staining the cells with Annexin-V (early apoptosis) and 7-AAD (viability dye). Representative of fluorescence data of each condition are displayed as bar graphs using the Flojo software, 100% values correspond to 50,000 cells and the data are the means of two independent experiments.
Figure 9C:
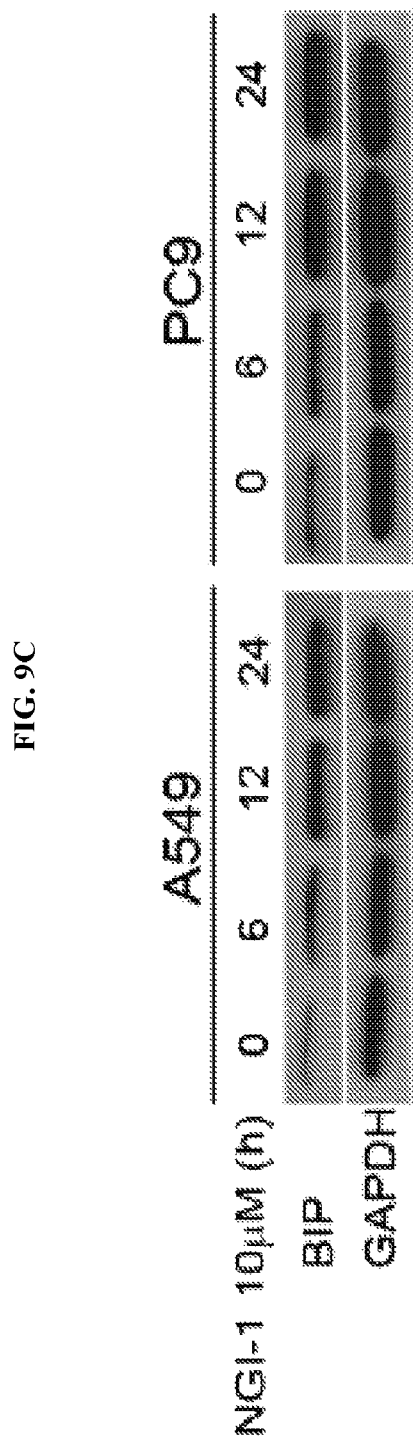
FIG. 9C: Western blot of BIP protein for A549 and PC9 cells after treatment with 10 μM NGI-1 for 6, 12 or 24 h. The expression of GAPDH was used as a loading control.
Figure 10:
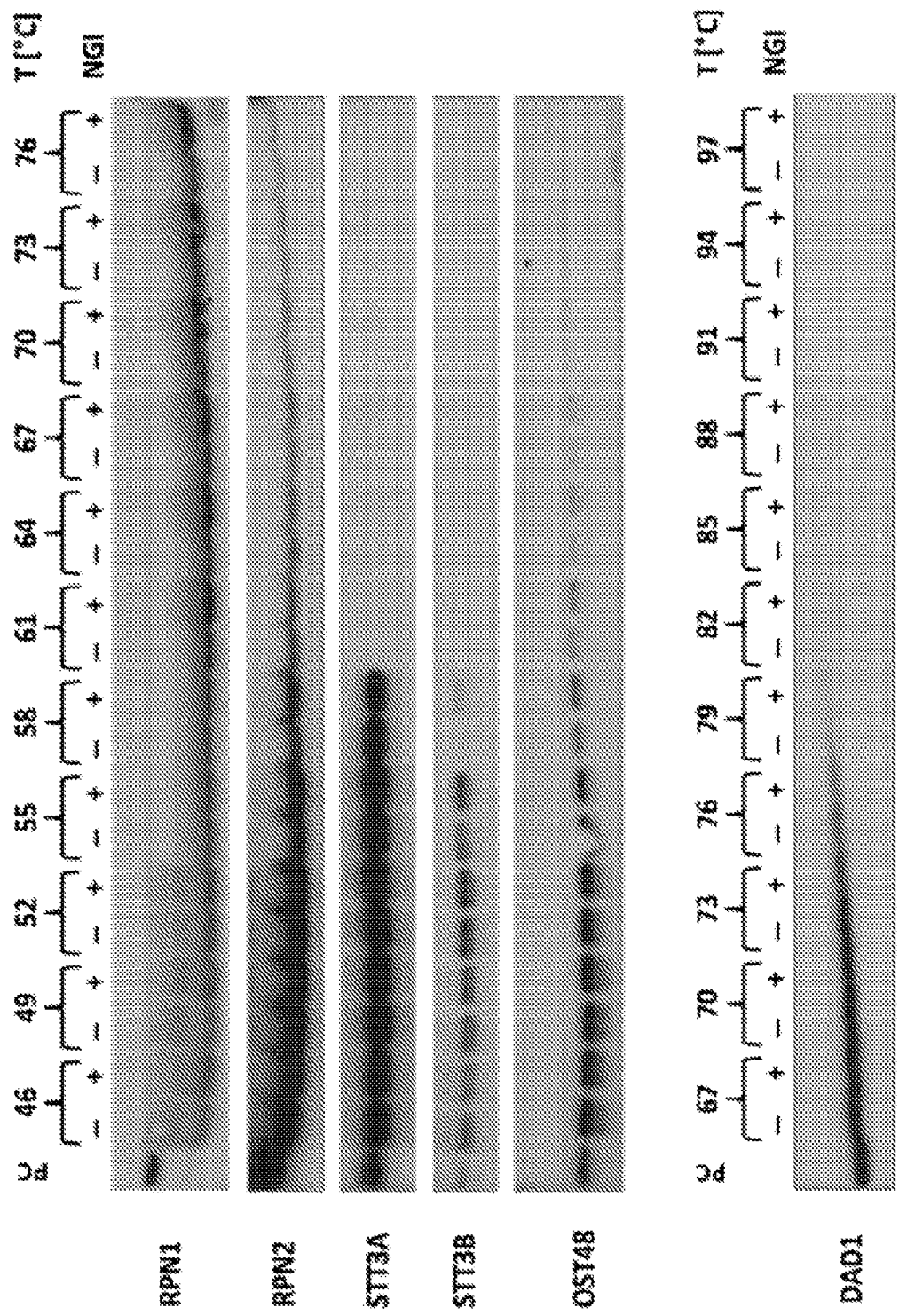
FIG. 10 illustrates cellular thermal shift assay (CETSA). CETSA of the five core OST subunits and two catalytic OST subunits in 293T cells after treatment with DMSO (PC) or 100 μM NGI-1 for 30 min. The 0 denotes no thermal treatment.

To assess the effects of NGI-1 on cellular signaling, phospho-protein levels of 43 signaling proteins were determined on arrays (FIGS. 4D-4E). Inhibition of EGFR activation by NGI-1 globally reduced phosphorylation of both kinases and effectors of downstream proliferative signaling in PC9 cells, however, only subtle quantitative effects on these phospho-proteins were observed in A549 cells (FIGS. 9A-9B). Significant reductions in phosphorylation of EGFR (Y1068; B2), Akt (T308; B6), p70 S6K (T421/424; D6), Src (Y419; D1), and CREB (S133; C2) suggests that NGI-1 effectively blocks oncogenic signaling from this transmembrane glycoprotein, but has only a minor effect on oncogenic signaling in other cell contexts such as the A549 cells.

Figure 4F:
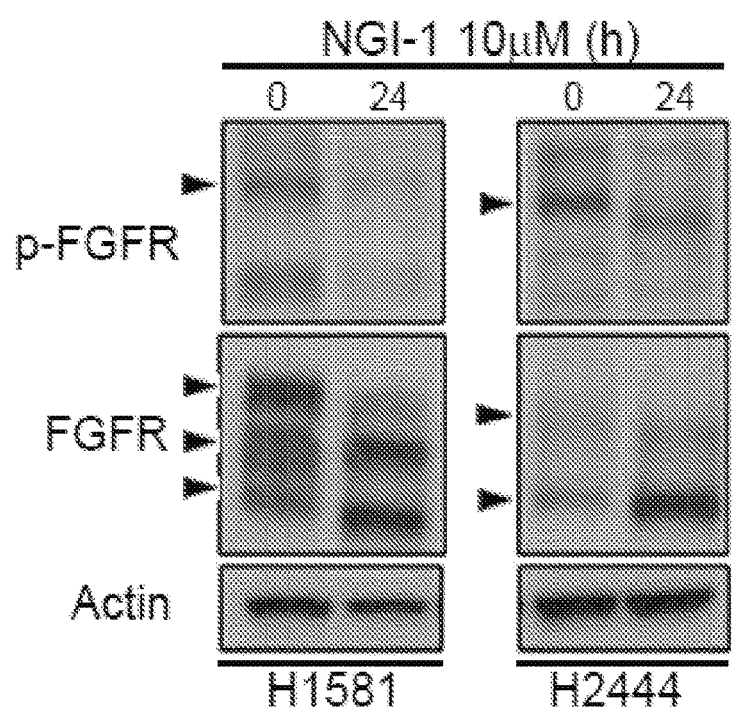
Figure 4G:
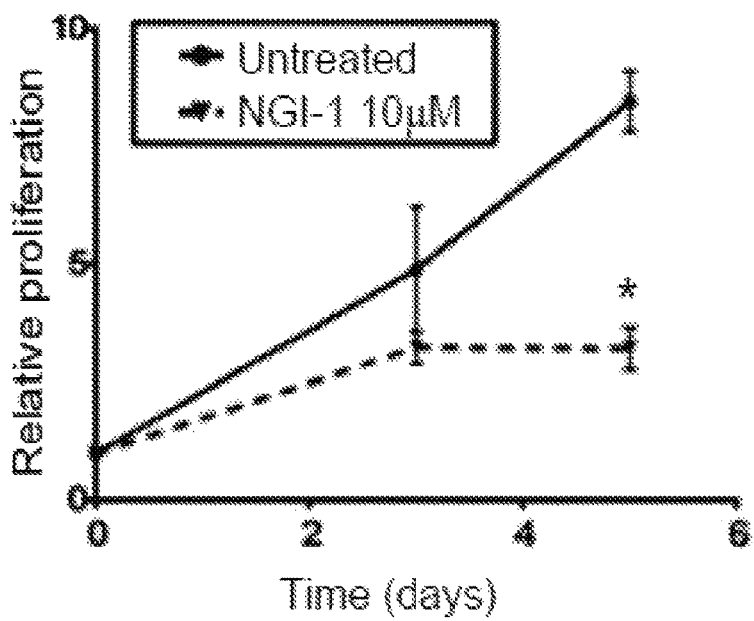
Figure 4H:
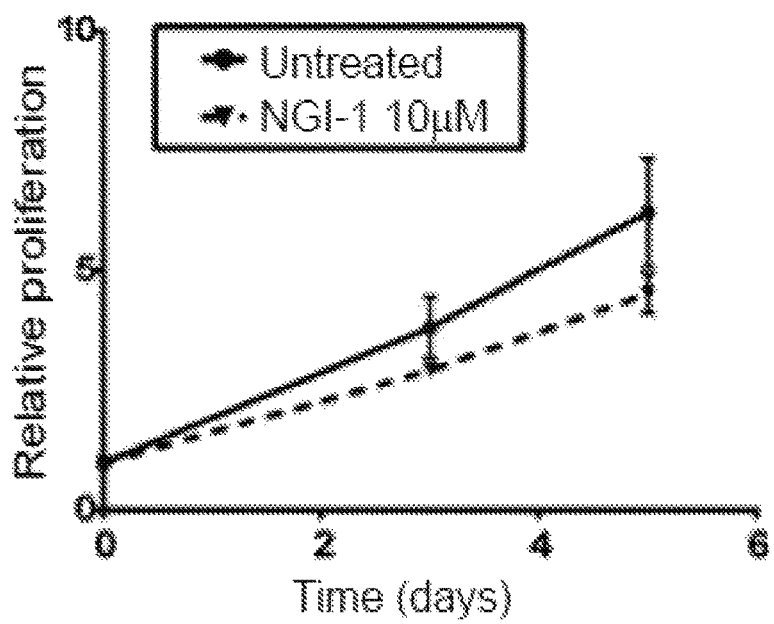

The effects of NGI-1 were then compared in two additional lung cancer cell lines; H1581 and H2444. Both of these cell lines are characterized by FGFR amplification, but only H1581 are dependent on FGFR1 signaling and are sensitive to inhibition with FGFR specific tyrosine kinase inhibitors. NGI-1 treatment enhanced FGFR mobility on PAGE, consistent with inhibition of N-linked glycosylation, and also blocked FGFR1 phosphorylation (FIG. 4F). Consistent with dependence on FGFR signaling, NGI-1 blocked proliferation of the H1581 cell line but not that of H2444 cells (FIGS. 4G-4H). Together, these results show that NGI-1 has potent inhibitory effects on cell types where proliferative signaling is driven by RTK glycoproteins.

Example 6: NGI-1 Induces G1 Arrest and Senescence in RTK Dependent Lung Cancer

Figure 5A:
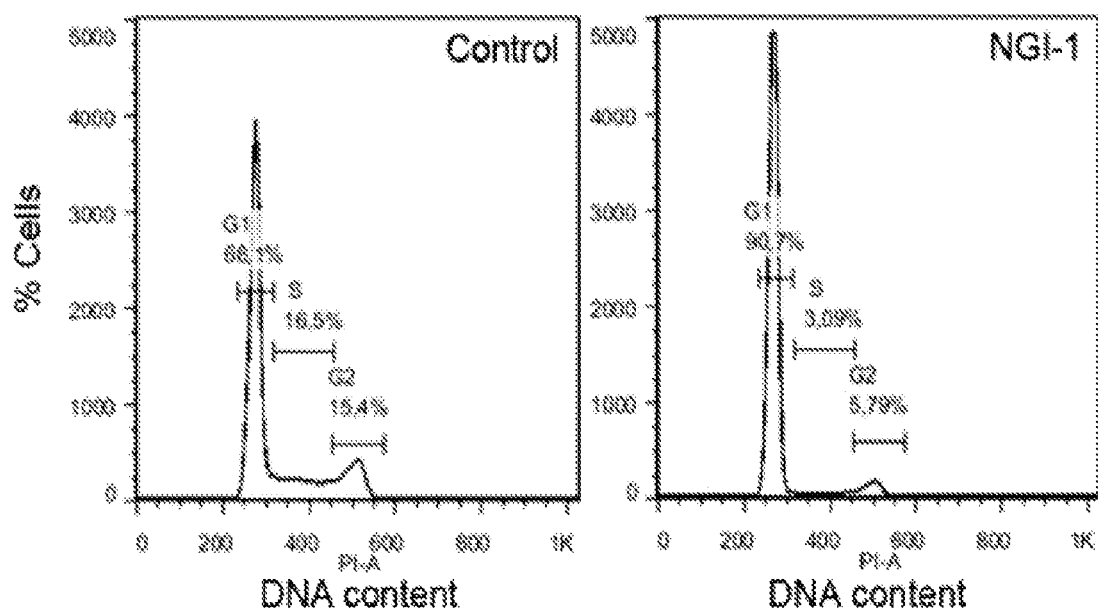
FIGS. 5A-5G illustrate NGI-1 induces G1 arrest and senescence in EGFR addicted tumor cells.
Figure 5A:
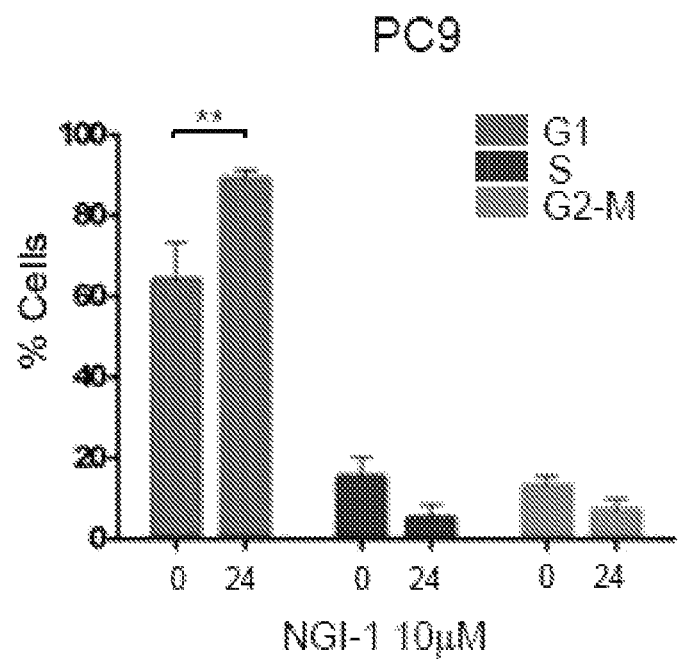
Figure 5B:
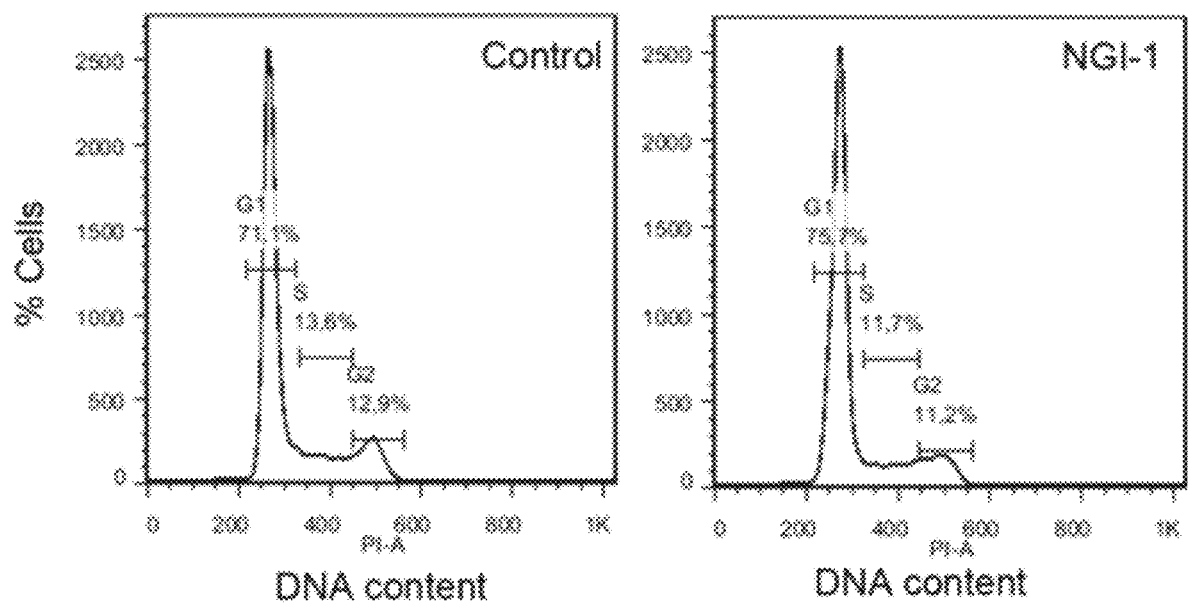
Figure 5B:
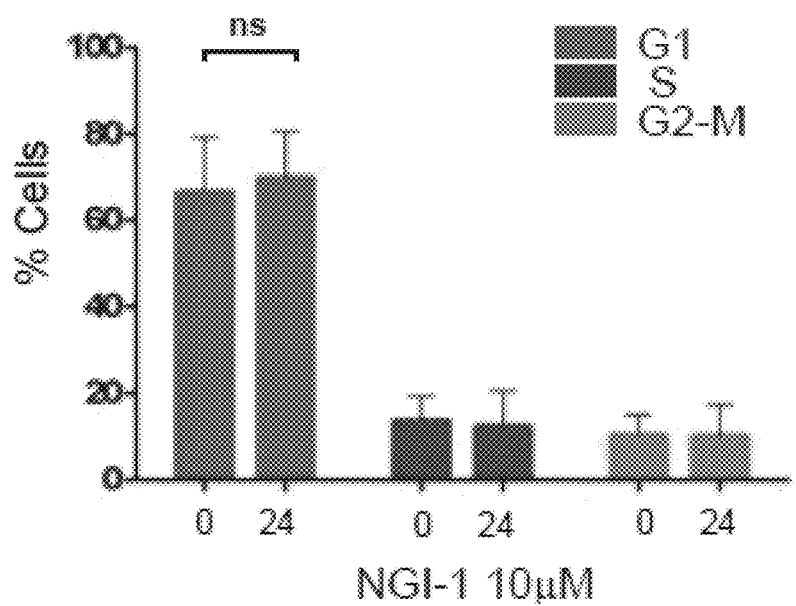
Figure 5C:
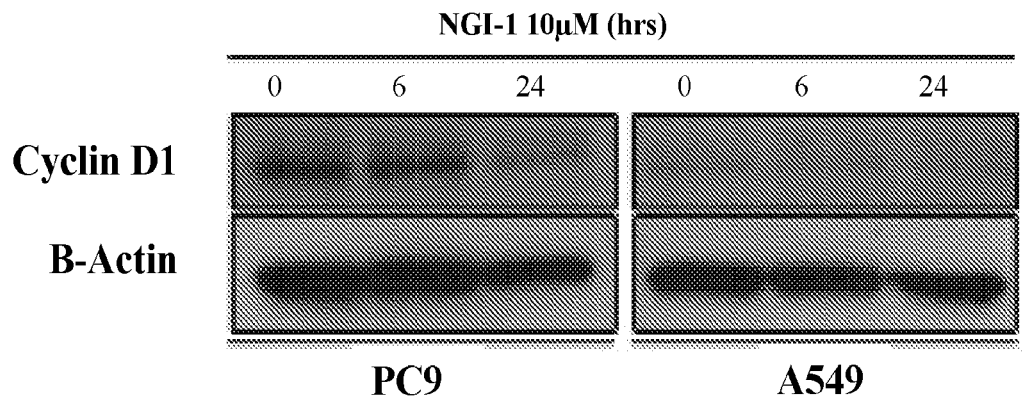
Figure 5D:
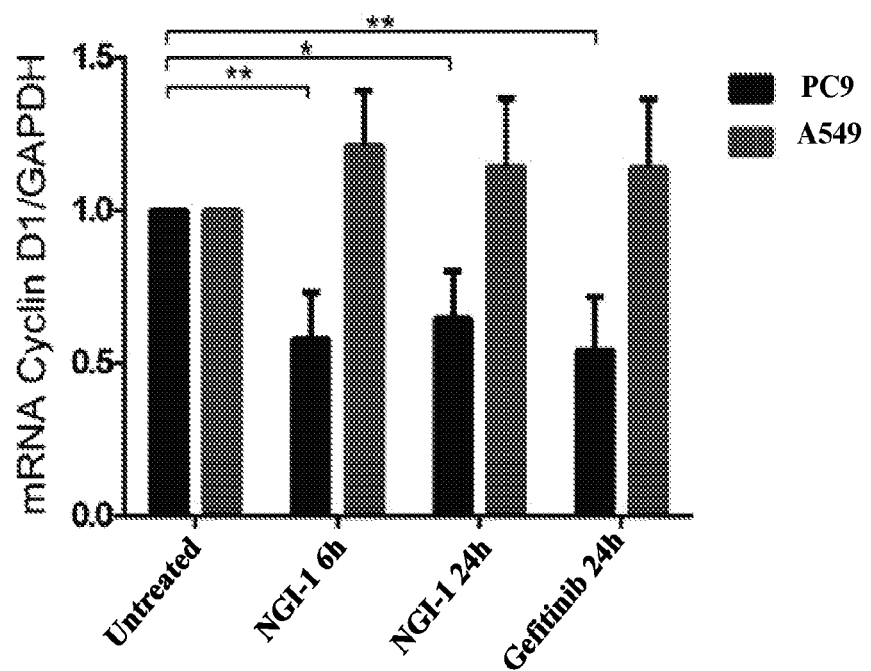

To determine the underlying mechanism for the proliferative changes in RTK driven lung cancer cells after inhibition of N-linked glycosylation with NGI-1, cell cycle and apoptosis were assessed in the PC9 and A549 cell lines. Treatment of both NSCLC cell lines with NGI-1 for 2 or 5 days did not induce apoptosis, though apoptosis was activated by tunicamycin treatment in both cell lines (FIG. 9A-9B). Analysis of cell cycle distribution by flow cytometry demonstrated a significant increase in G1 for NGI-1 treated PC9 cells after 24 h (65% vs 90% p<0.01), but did not significantly change the cell cycle distribution of A549 cells (FIGS. 5A-5B). Additionally a sub-G1 peak, which can be observed with induction of apoptosis, was not present in NGI-1 treated PC9 cells, providing further evidence that these cells do not undergo apoptosis. Consistent with the observed G1 cell cycle arrest in PC9 cells, cyclin D1 was significantly reduced at both the mRNA (40%±15%, p<0.01) and protein levels (40%) in PC9 cells, but not significantly affected in A549 cells (FIGS. 5C-SD).

Figure 5E:
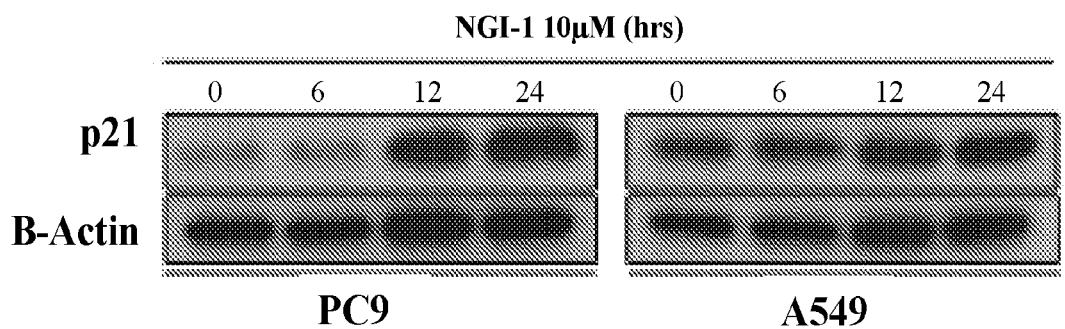
Figure 5F:
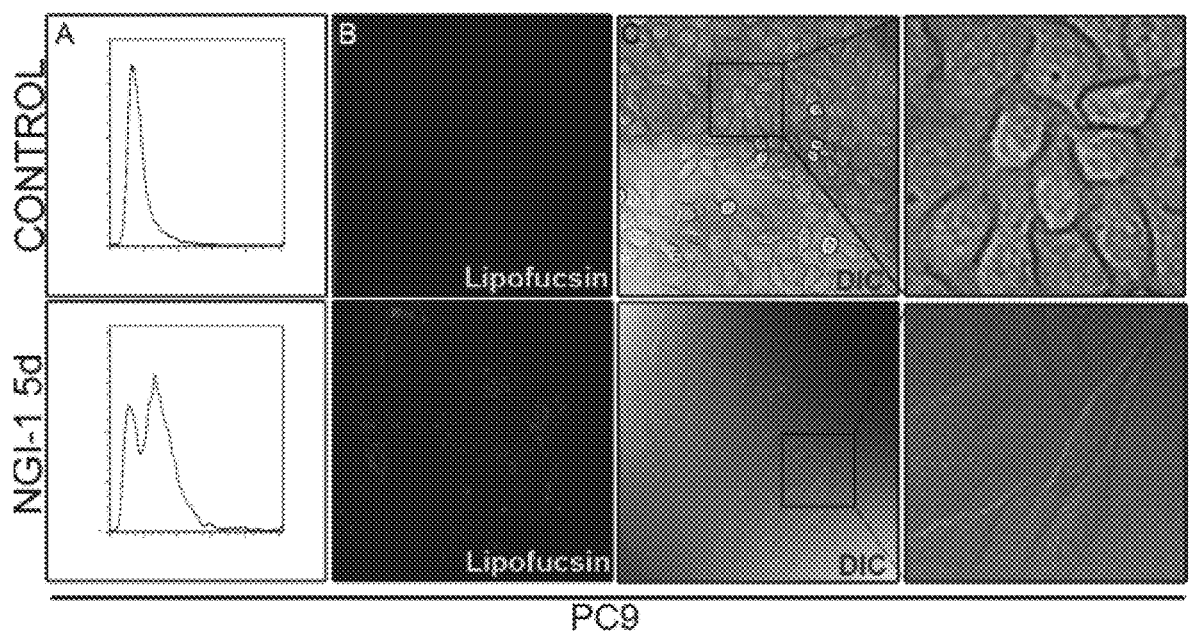
Figure 5G:
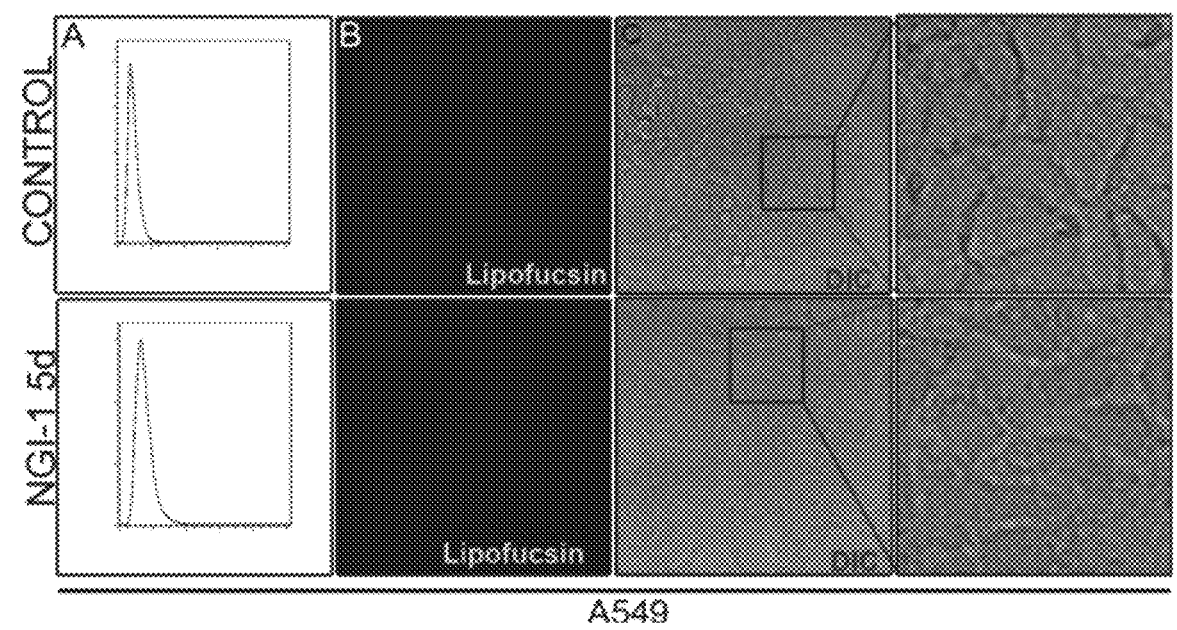
Figure 6A:
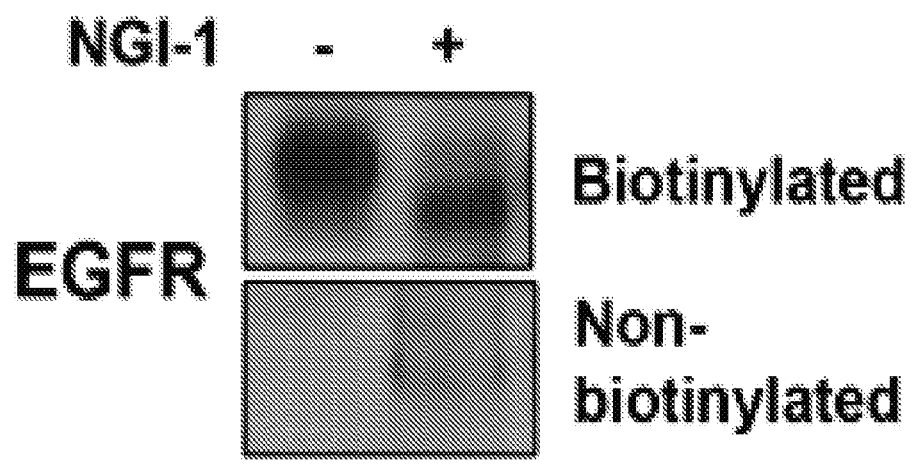
Figure 6C:
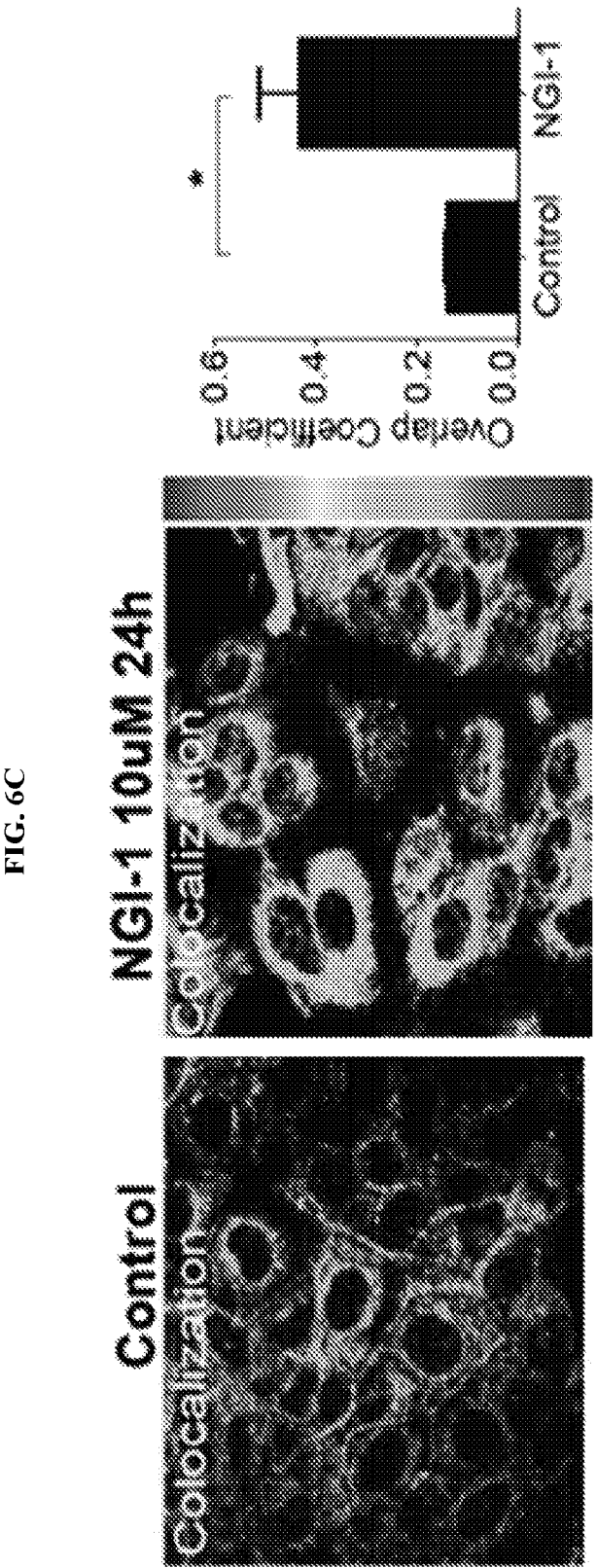

Protein levels of p21 were also analysed in PC9 cells and found to increase within 24 h after NGI-1 treatment (FIG. 5E). This protein is a cell cycle regulator and marker for senescence, raising the possibility that inhibition of N-linked glycosylation with NGI-1 could preferentially induce senescence. It was therefore assessed for additional hallmarks of senescence in PC9 and A549 NSCLC cells following control or NGI-1 treatment for 5 days (FIGS. 5F-4G). PC9 cells were found to increase autofluorescence by flow cytometry (<60%), fluorescent aggregates consistent with lipofuscin accumulation by microscopy, and cell morphology changes characterized by enlarged and flattened cells (FIG. 5F). In comparison none of these changes were detected in A549 cells (FIG. 5G). Together these results provide strong evidence that inhibition of N-linked glycosylation induces cell cycle arrest and senescence in tumor cells with RTK driven oncogenic signalling.

Example 7

The screen was successful in identifying a novel compound that inhibits N-linked glycan site occupancy, and subsequent SAR studies define an aminobenzamidosulfonamide chemical series that blocks N-linked glycosylation in mammalian cells. NGI-1, the lead compound from this series, does not disrupt synthesis of lipid linked oligosaccharides. Instead NG-1 alters the enzymatic reaction of glycosylation per se, and causes both accumulation of mature LLOs and a marked reduction of N-linked glycosylated proteins. Without wishing to be limited to any theory, these findings strongly suggest that the biologic target of NGI-1 is the OST, a hypothesis that is further supported by inhibition of glycosylation in microsomes. NGI-1 uniformly reduces receptor glycosylation, and function and alters receptor trafficking in NSCLC cell lines that express RTK glycoproteins (EGFR and FGFR), but is selective for inducing G1 arrest and senescence in only those cell lines that are RTK dependent.

NGI-1 is a cell permeable small molecule inhibitor of N-linked glycosylation and joins tunicamycin, a nucleoside antibiotic isolated from *Streptomyces* bacteria. NGI-1 has a distinctive biological effect on tumor cells in comparison to tunicamycin; it selectively induces senescence while tunicamycin indiscriminately causes apoptosis and cell death. Without wishing to be limited to any theory, this difference can be explained by the mechanisms of action for each inhibitor. First, tunicamycin eliminates the synthesis of all N-linked glycan precursors and indirectly blocks N-linked glycosylation. In contrast NGI-1 directly blocks the transfer of glycan precursors and has no effect on LLO biosynthesis. Second, while tunicamycin completely blocks the activity of a single enzymatic protein (DPAGT1). NGI-1 targets the multisubunit OST complex and incompletely blocks its activity. In mammalian cells the OST exists in multiple isoforms and contains one of two encoded catalytic subunits (STT3A or STT3B). Catalytic subunit dependent glycosylation of specific protein consensus sequences has been defined; however, NGI-1 treatment does not reproduce this specificity, suggesting that NGI-1 is not specific for one catalytic subunit. The incomplete inhibition of LLO transfer is therefore most likely to be caused by partial inhibition of a site common to OST holoenzyme isoforms instead of discrete inhibition of a specific catalytic subunit. Considering NGI-1's novel mechanism of action as well as the cell-based screening approach, which itself selects for cell viability, it is not surprising that this inhibitor blocks N-linked glycosylation with reduced cellular toxicity.

RTK extracellular domains are highly modified with N-linked glycans which contribute to stable conformations that facilitate ligand binding and regulate downstream signal transduction. The EGFR and FGFR1, for example, have eleven and eight consensus glycosylation sites respectively, whereas the average number of N-linked sites per glycoprotein is estimated to be only 1.9. Without being limited to any theory, it is therefore hypothesized that RTKs represent a protein class that is particularly sensitive to inhibition of N-linked glycosylation. Moreover, with the discovery of NGI-1, small molecule inhibition of the OST would have greater effects on cell types that are dependent on RTKs for proliferation. To this end, it was evaluated that the consequences of OST inhibition in NSCLC cell lines where proliferative signaling is driven by either EGFR kinase domain mutation or FGFR1 amplification. It was found that proliferation was blocked in NSCLC tumor cells that are dependent on RTKs (PC-9, HCC-827, H3255, H1581), but that other NSCLC cells (A549, H2444) are insensitive to NGI-1. It was also found that although RTK glycosylation was altered in all cell lines, effects on downstream signaling proteins that regulate proliferation were observed only in RTK dependent lines. NGI-1 treatment also induced a G1 arrest in only the RTK dependent cell lines, however, this arrest did not lead to apoptosis. Instead, markers of G1 arrest such as loss of cyclin D1 expression were accompanied by hallmarks of senescence; induction of p21, increased autofluorescence consistent with lipofuscin accumulation, and changes in cellular morphology.

Together this data provides both a molecular and cellular rationale for the selective effects of NGI-1 on RTK dependent NSCLC cell proliferation, and further suggests that strategies to target N-linked glycosylation could prove useful as therapeutic approaches for treating RTK driven malignancies.

In certain embodiments, NGI-1 has a unique biologic activity: it blocks the transfer of mature glycan precursors to recipient proteins; and displays reduced toxicity compared to tunicamycin.

TABLE 1

SAR Summary

| Entry | R¹ | NLG Inhibition ASSAY Potency Mean (μM) | | | Cytotoxicity Assay Mean (μM) | | | Selectivity |
|---|---|---|---|---|---|---|---|---|
| | | n | $AC_{40}$ μM) | max act, % | n | cell line | $EC_{50}$ μM | ($EC_{50}/AC_{40}$) |
| 1 | 5-CH₃-aminothiazole | 29 | 0.17 | 321.4 | 6 | HEPG2 | >30 | >172 |
| | | | | | 6 | HEK293 | >30 | >172 |
| 2 | 4-CH₃-aminothaizole | 11 | 0.57 | 300.8 | 6 | HEPG2 | >30 | >52.6 |
| | | | | | 6 | HEK293 | >30 | >52.6 |
| 3 | 2-aminothaizole | 11 | 1.9 | 238.9 | 6 | HEPG2 | >30 | >15.7 |
| | | | | | 6 | HEK293 | >30 | >15.7 |
| 4 | 5-CH₃-aminothiadiazole | 4 | 4.6 | 84.6 | 2 | HEPG2 | >30 | >6.6 |
| | | | | | 2 | HEK293 | >30 | >6.6 |
| 5 | 5-CH₃-aminotriazole | 4 | NA | 22.8 | 2 | HEPG2 | >30 | NA |
| | | | | | 2 | HEK293 | >30 | NA |
| 6 | 2-aminobenzothiazole | 11 | 0.47 | 310.2 | 6 | HEPG2 | >30 | >63.8 |
| | | | | | 6 | HEK293 | >30 | >63.8 |
| 7 | 4-CH₃O-beizothiazoic | 7 | NA | 23.5 | 4 | HEPG2 | >30 | NA |
| | | | | | 4 | HEK293 | >30 | NA |
| 8 | 5-CH₃O-benzothiazole | 7 | ND | 31.3 | 4 | HEPG2 | >30 | NA |
| | | | | | 4 | HEK293 | >30 | NA |
| 9 | 6-CH₃O-benzothiazole | 7 | 13.1 | 85.7 | 6 | HEPG2 | >30 | >2.3 |
| | | | | | 6 | HEK293 | >30 | >2.3 |
| 10 | 3-aminopyridyl | 4 | NA | 48.4 | 2 | HEPG2 | >30 | NA |
| | | | | | 2 | HEK293 | >30 | NA |
| 11 | 4-aminopyridyl | 4 | NA | 25 | 2 | HEPG2 | >30 | NA |
| | | | | | 2 | HEK293 | >30 | NA |
| 12 | aniline | 11 | 1.1 | 183.0 | 6 | HEPG2 | >30 | >27.8 |
| | | | | | 6 | HEK293 | >30 | >27.8 |
| 13 | 2-CH₃-aniline | 4 | NA | 10.7 | 2 | HEPG2 | >30 | NA |
| | | | | | 2 | HEK293 | >30 | NA |
| 14 | 4-CH₃-aniline | 11 | 1.2 | 305.0 | 6 | HEPG2 | >30 | >25.0 |
| | | | | | 6 | HEK293 | >30 | >25.0 |
| 15 | 2-MeO-aniline | 4 | NA | 30.1 | 2 | HEPG2 | >30 | NA |
| | | | | | 2 | HEK293 | >30 | NA |
| 16 | 4-MeO-aniline | 4 | 10.3 | 79.9 | 2 | HEPG2 | >30 | >2.9 |
| | | | | | 2 | HEK293 | >30 | >2.9 |
| 17 | 2-F-aniline | 4 | NA | NA | 2 | HEPG2 | >30 | NA |
| | | | | | 2 | HEK293 | >30 | NA |
| 18 | 3-F-aniline | 8 | 2.6 | 107.7 | 6 | HEPG2 | >30 | >11.5 |
| | | | | | 6 | HEK293 | >30 | >11.5 |
| 19 | 2-Cl-aniline | 4 | NA | 24.7 | 2 | HEPG2 | >30 | NA |
| | | | | | 2 | HEK293 | >30 | NA |
| 20 | 4-Br-aniline | 4 | NA | 32 | 2 | HEPG2 | >30 | NA |
| | | | | | 2 | HEK293 | >30 | NA |
| 21 | N-morpholine | 4 | NA | 23.6 | 2 | HEPG2 | >30 | NA |
| | | | | | 2 | HEK293 | >30 | NA |
| 22 | cyclohexylamine | 4 | NA | NA | 2 | HEPG2 | >30 | NA |
| | | | | | 2 | HEK293 | >30 | NA |
| 23 | dimentylamine | 4 | NA | 32.1 | 2 | HEPG2 | >30 | NA |
| | | | | | 2 | HEK2 3 | >30 | NA |

TABLE 1-continued

SAR Summary

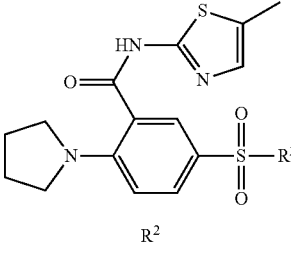

| Entry | R² | n | AC₄₀ (µM) | max act, % | n | cell line | EC₅₀ µM | Selectivity (EC₅₀/AC₄₀) |
|---|---|---|---|---|---|---|---|---|
| | | | NLG Inhibition ASSAY Potency Mean (µM) | | | Cytotoxicity Assay Mean (µM) | | |
| 1 | N(CH₃)₂ | 29 | 0.17 | 321.4 | 6 | HEK293 | >30 | >172 |
| | | | | | 6 | HEPG2 | >30 | >172 |
| 2 | N(CH₂CH₃)₂ | 4 | 11.9 | 80.2 | 2 | HEK293 | >30 | >2.5 |
| | | | | | 2 | HEPG2 | >30 | >2.5 |
| 3 | N-pyrrolidine | 11 | 0.93 | 210.3 | 6 | HEK293 | >30 | >32.3 |
| | | | | | 6 | HEPG2 | >30 | >32.3 |
| 4 | N-piperidine | 11 | 7.1 | 68.8 | 6 | HEK293 | >30 | >4.2 |
| | | | | | 6 | HEPG2 | >30 | >4.2 |
| 5 | N-morpholine | 11 | 0.31 | 302.0 | 6 | HEK293 | >30 | >96.8 |
| | | | | | 6 | HEPG2 | >30 | >96.8 |
| 6 | N-piperazine | 4 | NA | 74 1 | 2 | HEK293 | >30 | >3.2 |
| | | | | | 2 | HEPG2 | >30 | >3.2 |
| 7 | CH₃Ph | 4 | NA | 10.9 | 2 | HEK293 | >30 | NA |
| | | | | | 2 | HEK293 | >30 | NA |
| 8 | NHCH₂Ph | 4 | 19.5 | 81.6 | 2 | HEPG2 | >30 | >1.5 |
| | | | | | 2 | HEK293 | >30 | >1.5 |

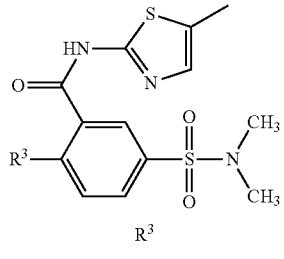

| Entry | R³ | n | AC₄₀ (µM) | max act, % | n | cell line | EC₅₀ µM | Selectivity (EC₅₀/AC₄₀) |
|---|---|---|---|---|---|---|---|---|
| | | | NLG Inhibition ASSAY Potency Mean (µM) | | | Cytotoxicity Assay Mean (µM) | | |
| 1 | N-pyrrolidine | 29 | 0.17 | 321.4 | 6 | HEK293 | >30 | >172 |
| | | | | | 6 | HEPG2 | >30 | >172 |
| 2 | N-piperidine | 4 | 11.9 | 52.9 | 2 | HEK293 | >30 | >2.2 |
| | | | | | 2 | HEPG2 | >30 | >2.2 |
| 3 | N-azetidine | 11 | 0.93 | 340.1 | 6 | HEK293 | >30 | >83.3 |
| | | | | | 6 | HEPG2 | >30 | >83.3 |
| 4 | N-piperazine | 11 | 7.1 | 29.1 | 2 | HEK293 | >30 | NA |
| | | | | | 2 | HEPG2 | >30 | NA |
| 5 | N(CH₃)₂ | 11 | 0.31 | 113.1 | 6 | HEK293 | >30 | >5.8 |
| | | | | | 6 | HEPG2 | >30 | >5.8 |
| 6 | N(Et)₂ | 4 | NA | 126.8 | 6 | HEK293 | >30 | >9.4 |
| | | | | | 6 | HEPG2 | >30 | >9.4 |
| 7 | cyclopentyl | 4 | NA | 137.2 | 6 | HEK293 | >30 | >13.6 |
| | | | | | 6 | HEK293 | >30 | >13.6 |
| 8 | H | 4 | 19.5 | 16.9 | 2 | HEPG2 | >30 | NA |
| | | | | | 2 | HEK293 | >30 | NA |

TABLE 2

IUPAC Names of Compound Listed in Table 1

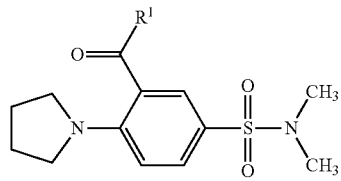

| R¹ | IUPAC Name |
|---|---|
| 5-CH₃-aminothiazole | 5-(N,N-Dimethylsulfamoyl)-N-(5-methylthiazol-2-yl)-2-(pyrrolidin-1-yl)benzamide |
| 4-CH₃-aminothaizole | 5-(dimethylsuifamoyl)-N-(4-methyl-1,3-thiazol-2-yl)-2-pyrrolidin-1-ylbenzamide |
| 2-aminothiazole | 5-(dimethylsulfamoyl)-2-pyrrolidin-1-yl-N-(1,3-thiazol-2-yl)benzamide |
| 5-CH₃-aminothiadiazole | 5-(dimethylsulfamoyl)-N-(5-methyl-1,3,4-thiadiazol-2-yl)-2-pyrrolidin-1-ylbenzamide |
| 5-CH₃-aminotriazole | 5-(dimethylsulfamoyl)-N-(5-methyl-1H-1,2,4-triazol-3-yl)-2-pyrrolidin-1-ylbenzamide |
| 2-aminobenzothiazole | N-(1,3-benzothiazol-2-yl)-5-(dimethylsulfamoyl)-2-pyrrolidin-1-ylbenzamide |
| 4-CH₃O-benzothiazole | 5-(dimethylsulfamoyl)-N-(4-methoxy-1,3-benzothiazol-2-yl)-2-pyrrolidin-1-ylbenzamide |
| 5-CH₃O-benzothiazole | 5-(dimethylsulfamoyl)-N-(5-methoxy-1,3-benzothiazol-2-yl)-2-pyrrolidin-1-ylbenzamide |
| 6-CH₃O-benzothiazole | 5-(dimethylsulfamoyl)-N-(6-methoxy-1,3-benzothiazol-2-yl)-2-pyrrolidin-1-ylbenzamide |
| 3-aminopyridyl | 5-(dimethylsulfamoyl)-N-pyridin-3-yl-2-pyrrolidin-1-ylbenzamide |
| 4-aminopyridyl | 5-(dimethylsulfamoyl)-N-pyridin-4-yl-2-pyrrolidin-1-ylbenzamide |
| aniline | 5-(dimethylsulfamoyl)-N-phenyl-2-pyrrolidin-1-ylbenzamide |
| 2-CH₃-aniline | 5-(dimethylsulfamoyl)-N-(2-methylphenyl)-2-pyrrolidin-1-ylbenzamide |
| 4-CH₃-aniline | 5-(dimethylsulfamoyl)-N-(4-methylphenyl)-2-pyrrolidin-1-ylbenzamide |
| 2-MeO-aniline | 5-(dimethylsulfamoyl)-N-(2-methoxyphenyl)-2-pyrrolidin-1-ylbenamide |
| 4-MeO-aniline | 5-(dimethylsulfamoyl)-N-(4-methoxyphenyl)-2-pyrrolidin-1-ylbenzamide |
| 2-F-aniline | 5-(dimethylsulfamoyl)-N-(2-fluorophenyl)-2-pyrrolidin-1-ylbenzamide |
| 3-F-aniline | 5-(dimethylsulfamoyl)-N-(3-fluorophenyl)-2-pyrrolidin-1-ylbenzamide |
| 2-Cl-aniline | 5-(dimethylsulfamoyl)-N-(2-chlorophenyl)-2-pyrrolidin-1-ylbenzamide |
| 4-Br-aniline | 5-(dimethylsulfamoyl)-N-(4-bromophenyl)-2-pyrrolidin-1-ylbenzamide |
| N-morpholine | N,N-dimethyl-3-(morpholine-4-cabrbonyl)-4-pyrrolidin-1-ylbenzenesulfonamide |
| cyclohexylamine | N-cyclohexyl-5-(dimethylsulfamoyl)-2-pyrrolidin-1-ylbenzamide |
| dimentylamine | 5-(dimethylsulfamoyl)-N,N-dimethyl-2-pyrrolidin-1ylbenzamide |

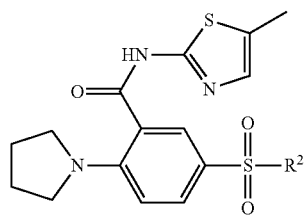

| R² | IUPAC Name |
|---|---|
| N(CH₃)₂ | 5-(dimethylsulfamoyl)-N-(5-methyl-1,3-thiazol-2-yl)-2-pyrrolidin-1-ylbenzamide |
| N(CH₂CH₃)₂ | 5-(diethylsulfamoyl)-N-(5-methyl-1,3-thiazol-2-yl)-2-pyrrolidin-1-ylbenzamide |
| N-pyrrolidine | N-(5-methyl-1,3-thiazol-2-yl)-2-pyrrolidin-1-yl-5-pyrrolidin-1-ylsulfonlbenzamide |
| N-piperidine | N-(5-methyl-1,3-thiazol-2-yl)-2-piperidine-1-yl-5-pyrrolidin-1-ylsulfonylbenzamide |
| N-morpholine | N-(5-methyl-1,3-thiazol-2-yl)-2-morpholin-1-yl-5-pyrrolidin-1-ylsulfonylbenazmide |
| N-piperazine | N-(5-methyl-1,3-thiazol-2-yl)-2-piperazin-1-yl-5-pyrrolidin-1-ylsulfonylbenzamide |

TABLE 2-continued

| IUPAC Names of Compound Listed in Table 1 | |
|---|---|
| CH₃Ph | 5-[methyl(phenyl)sulfamoyl]-N-(5-methyl-1,3-thiazol-2-yl)-2-pyrrolidin-1-ylbenzamide |
| NHCH₂Ph | 5-(benzylsulfamoyl)-N-(5-methyl-1,3-thiazol-2-yl)-2-pyrrolidin-1-ylbenzamide |

| $R^3$ | IUPAC Name |
|---|---|
| N-pyrrolidine | 5-(dimethylsulfamoyl)-N-(5-methyl-1,3-thiazol-2-yl)-2-pyrrolidin-1-ylbenzamide |
| N-piperidine | 5-(dimethylsulfamoyl)-N-(5-methyl-1,3-thiazol-2-yl)-2-piperidin-1-ylbenzamide |
| N-azetidine | 2-(acetidin-1-yl)-5-(dimethylsulfamoyl)-N-(5-methyl-1,3-thiazol-2-yl)benzamide |
| N-piperazine | 5-dimethylsulfamoyl-N-(5-methyl-1,3-thiazol-2-yl)-2-piperazin-1-ylbenzamide |
| N(CH₃)₂ | 2-(dimethylamino)-5-(dimethylsulfamoyl)-N-(5-methyl-1,3-thiazol-2-yl)benzamide |
| N(Et)₂ | 2-(diethylamino)-5-(dimethylsulfamoyl)-N-(5-methyl-1,3-thiazol-2-yl)benzamide |
| cyclopentyl | 2-cyclopentyl-5-(dimethylsulfamoyl)-N-(5-methyl-1,3-thiazol-2-yl)benzamide |
| H | 3-(dimethylsulfamoyl)-N-(5-methyl-1,3-thiazol-2-yl)benzamide |

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inhibiting or disrupting N-linked glycosylation in a cell, the method comprising contacting the cell with an effective amount of a compound of formula (I):

(I)

wherein:

$R^1$ is selected from the group consisting of m=1 or 2;

$R^2$ is selected from the group consisting of and $-N(R^4)_2$;

$R^3$ is selected from the group consisting of each occurrence of $R^4$ is independently selected from the group consisting of H, -($C_1$-$C_6$)alkyl, -($C_3$-$C_6$)cycloalkyl, -(C$_1$-C$_6$)haloalkyl, -(C$_1$-C$_6$)alkoxy, -(C$_3$-C$_{10}$)heterocyclyl, -(C$_1$-C$_6$)heteroalkyl, —F, —Cl, —Br, —I, —CN, —NO$_2$, —OR$^5$, —SR$^5$, —S(=O)R$^5$, —S(=O)$_2$R$^5$, —C(=O)R$^5$, —OC(=O)R$^5$, —C(=O)OR$^5$, aryl, —CH$_2$-aryl, and -(C$_5$-C$_{10}$)heteroaryl, wherein the alkyl, heteroalkyl, cycloalkyl, heterocyclyl, aryl, or heteroaryl group is optionally substituted; and, each occurrence of R$^5$ is independently selected from the group consisting of H, -(C$_1$-C$_6$) alkyl, -(C$_1$-C$_6$) heteroalkyl, -(C$_3$-C$_6$) cycloalkyl, -(C$_3$-C$_{10}$) heterocyclyl, aryl, and -(C$_5$-C$_{10}$) heteroaryl, wherein the alkyl, heteroalkyl, cycloalkyl, heterocyclyl, aryl, or heteroaryl group is optionally substituted;

or a salt or N-oxide thereof.

2. The method of claim 1, wherein the cell is a receptor tyrosine kinase-dependent cancer cell.

3. The method of claim 2, wherein the receptor tyrosine kinase-dependent cancer is selected from the group consisting of non-small cell lung cancer, small cell lung cancer, head and neck squamous cell carcinoma, breast cancer, gastric cancer, cervical cancer, bladder cancer, ovarian cancer, colon cancer, rectal cancer, colorectal cancer, glioblastoma, and glioma.

4. The method of claim 1, wherein the cell is in vivo in a mammal and wherein the compound is administered to the mammal.

5. A method of treating or ameliorating a receptor tyrosine kinase-dependent cancer in a subject in need thereof,
wherein the receptor tyrosine kinase-dependent cancer comprises non-small cell lung cancer, small cell lung cancer, head and neck squamous cell carcinoma, breast cancer, gastric cancer, cervical cancer, bladder cancer, ovarian cancer, colon cancer, rectal cancer, colorectal cancer, glioblastoma, or glioma,
the method comprising administering to the subject a therapeutically effective amount of a compound of formula (I):

(I)

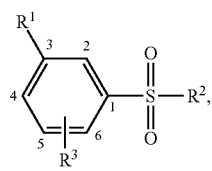

wherein:
R$^1$ is selected from the group consisting of

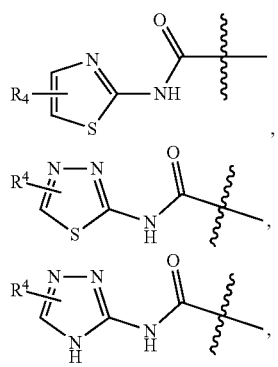

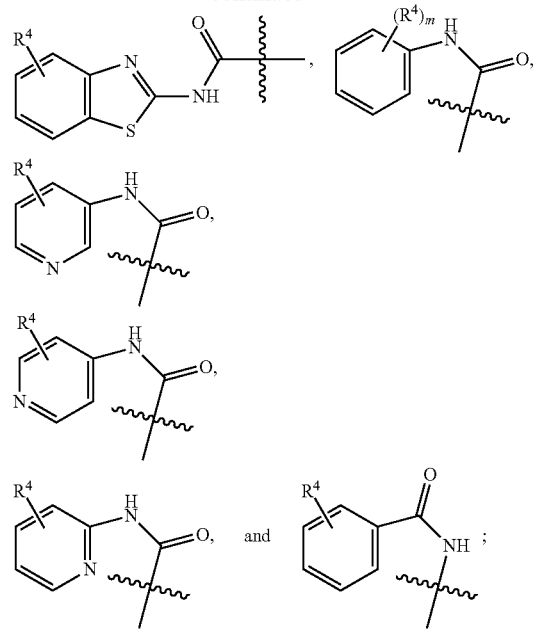

m=1 or 2;
R$^2$ is selected from the group consisting of

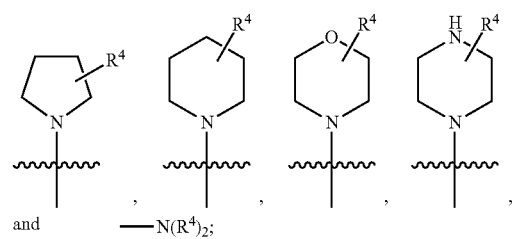

R$^3$ is selected from the group consisting of

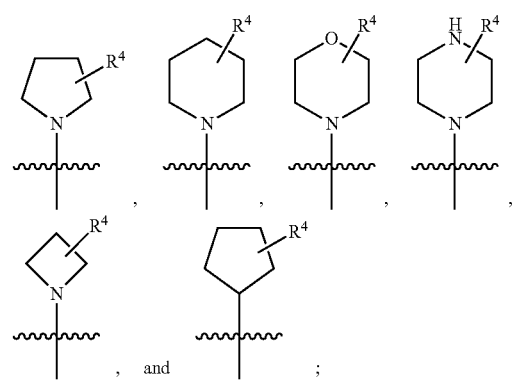

each occurrence of R$^4$ is independently selected from the group consisting of H, -(C$_1$-C$_6$)alkyl, -(C$_3$-C$_6$)cycloalkyl, -(C$_1$-C$_6$)haloalkyl, -(C$_1$-C$_6$)alkoxy, -(C$_3$-C$_{10}$)heterocyclyl, -(C$_1$-C$_6$)heteroalkyl, —F, —Cl, —Br, —I, —CN, —NO$_2$, —OR$^5$, —SR$^5$, —S(=O)R$^5$, —S(=O)$_2$R$^5$, —C(=O)R$^5$, —OC(=O)R$^5$, —C(=O)OR$^5$, aryl, —CH$_2$-aryl, and -(C$_5$-C$_{10}$)heteroaryl, wherein the alkyl, heteroalkyl, cycloalkyl, heterocyclyl, aryl, or heteroaryl group is optionally substituted; and, each occurrence of $R^5$ is independently selected from the group consisting of H, -($C_1$-$C_6$) alkyl, -($C_1$-$C_6$) heteroalkyl, -($C_3$-$C_6$) cycloalkyl, -($C_3$-$C_{10}$) heterocyclyl, aryl, and -($C_5$-$C_{10}$) heteroaryl, wherein the alkyl, heteroalkyl, cycloalkyl, heterocyclyl, aryl, or heteroaryl group is optionally substituted;

or a salt or N-oxide thereof.

6. A method of treating or ameliorating a receptor tyrosine kinase-dependent cancer in a subject in need thereof, wherein the receptor tyrosine kinase-dependent cancer comprises non-small cell lung cancer, small cell lung cancer, head and neck squamous cell carcinoma, breast cancer, gastric cancer, cervical cancer, bladder cancer, ovarian cancer, colon cancer, rectal cancer, colorectal cancer, glioblastoma, or glioma, the method comprising administering to the subject a therapeutically effective amount of at least one compound selected from the group consisting of: 5-(N,N-Dimethylsulfamoyl)-N-(5-methyl-1,3-thiazol-2-yl)-2-(pyrrolidin-1-yl)benzamide, 5-(dimethylsulfamoyl)-N-(4-methyl-1,3-thiazol-2-yl)-2-pyrrolidin-1-ylbenzamide, 5-(dimethylsulfamoyl)-2-pyrrolidin-1-yl-N-(1,3-thiazol-2-yl)benzamide, 5-(dimethylsulfamoyl)-N-(5-methyl-1,3,4-thiadiazol-2-yl)-2-pyrrolidin-1-ylbenzamide, 5-(dimethylsulfamoyl)-N-(5-methyl-1H-1,2,4-triazol-3-yl)-2-pyrrolidin-1-ylbenzamide, N-(1,3-benzothiazol-2-yl)-5-(dimethylsulfamoyl)-2-pyrrolidin-1-ylbenzamide, 5-(dimethylsulfamoyl)-N-(4-methoxy-1,3-benzothiazol-2-yl)-2-pyrrolidin-1-ylbenzamide, 5-(dimethylsulfamoyl)-N-(5-methoxy-1,3-benzothiazol-2-yl)-2-pyrrolidin-1-ylbenzamide, 5-(dimethylsulfamoyl)-N-(6-methoxy-1,3-benzothiazol-2-yl)-2-pyrrolidin-1-ylbenzamide, 5-(dimethylsulfamoyl)-N-pyridin-3-yl-2-pyrrolidin-1-ylbenzamide, 5-(dimethylsulfamoyl)-N-pyridin-4-yl-2-pyrrolidin-1-ylbenzamide, 5-(dimethylsulfamoyl)-N-phenyl-2-pyrrolidin-1-ylbenzamide, 5-(dimethylsulfamoyl)-N-(2-methylphenyl)-2-pyrrolidin-1-ylbenzamide, 5-(dimethylsulfamoyl)-N-(4-methylphenyl)-2-pyrrolidin-1-ylbenzamide, 5-(dimethylsulfamoyl)-N-(2-methoxyphenyl)-2-pyrrolidin-1-ylbenzamide, 5-(dimethylsulfamoyl)-N-(4-methoxyphenyl)-2-pyrrolidin-1-ylbenzamide, 5-(dimethylsulfamoyl)-N-(2-fluorophenyl)-2-pyrrolidin-1-ylbenzamide, 5-(dimethylsulfamoyl)-N-(3-fluorophenyl)-2-pyrrolidin-1-ylbenzamide, 5-(dimethylsulfamoyl)-N-(2-chlorophenyl)-2-pyrrolidin-1-ylbenzamide, 5-(dimethylsulfamoyl)-N-(4-bromophenyl)-2-pyrrolidin-1-ylbenzamide, 5-(dimethylsulfamoyl)-N-(5-methyl-1,3-thiazol-2-yl)-2-pyrrolidin-1-ylbenzamide, 5-(diethylsulfamoyl)-N-(5-methyl-1,3-thiazol-2-yl)-2-pyrrolidin-1-ylbenzamide, N-(5-methyl-1,3-thiazol-2-yl)-2-pyrrolidin-1-yl-5-pyrrolidin-1-ylsulfonyl benzamide, N-(5-methyl-1,3-thiazol-2-yl)-5-piperidin-1-ylsulfonyl-2-pyrrolidin-1-ylbenzamide, N-(5-methyl-1,3-thiazol-2-yl)-5-morpholin-4-ylsulfonyl-2-pyrrolidin-1-ylbenzamide, N-(5-methyl-1,3-thiazol-2-yl)-5-piperazin-1-ylsulfonyl-2-pyrrolidin-1-ylbenzamide, 5-[methyl(phenyl)sulfamoyl]-N-(5-methyl-1,3-thiazol-2-yl)-2-pyrrolidin-1-ylbenzamide, 5-(benzylsulfamoyl)-N-(5-methyl-1,3-thiazol-2-yl)-2-pyrrolidin-1-ylbenzamide, 5-(dimethylsulfamoyl)-N-(5-methyl-1,3-thiazol-2-yl)-2-piperidin-1-ylbenzamide, 5-(dimethylsulfamoyl)-N-(5-methyl-1,3-thiazol-2-yl)-2-piperazin-1-ylbenzamide, 2-(dimethylamino)-5-(dimethylsulfamoyl)-N-(5-methyl-1,3-thiazol-2-yl)benzamide, 2-(diethylamino)-5-(dimethylsulfamoyl)-N-(5-methyl-1,3-thiazol-2-yl) benzamide, 2-cyclopentyl-5-(dimethylsulfamoyl)-N-(5-methyl-1,3-thiazol-2-yl)benzamide, and 3-(dimethylsulfamoyl)-N-(5-methyl-1,3-thiazol-2-yl) benzamide;

or a salt or N-oxide thereof.

7. The method of claim 6, wherein the compound blocks or inhibits cell surface expression of the receptor tyrosine kinase in a cell from the cancer.

8. The method of claim 5, further comprising administering to the subject at least one additional therapeutic agent that treats or ameliorates the receptor tyrosine kinase-dependent cancer.

9. The method of claim 8, wherein the compound and the at least one additional therapeutic agent are co-administered to the subject.

10. The method of claim 9, wherein the compound and the at least one additional therapeutic agent are coformulated.

11. The method of claim 5, wherein the cancer comprises non-small cell lung cancer, small cell lung cancer, head and neck squamous cell carcinoma, breast cancer, gastric cancer, cervical cancer, colon cancer, or glioma.

12. The method of claim 5, wherein the compound is administered to the subject by at least one route selected from the group consisting of nasal, inhalational, topical, oral, buccal, rectal, pleural, peritoneal, vaginal, intramuscular, subcutaneous, transdermal, epidural, intrathecal and intravenous routes.

* * * * *

```
                        SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Synthetic primer

<400> SEQUENCE: 1
acctgaggag ccccaacaa                                                19

<210> SEQ ID NO 2
<211> LENGTH: 17
<212> TYPE: DNA
<213> ORGANISM: Artificial Sequence
<220> FEATURE:
<223> OTHER INFORMATION: Synthetic primer

<400> SEQUENCE: 2
tctgctcctg gcaggcc                                                  17

<210> SEQ ID NO 3
<211> LENGTH: 20
<212> TYPE: DNA
<213> ORGANISM: Artificial Sequence
<220> FEATURE:
```

```
<223> OTHER INFORMATION: Synthetic primer

<400> SEQUENCE: 3
gctctctgct cctcctgttc                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
acgaccaaat ccgttgactc                                              20
```